(12) United States Patent
Li et al.

(10) Patent No.: US 10,436,871 B2
(45) Date of Patent: Oct. 8, 2019

(54) LOW-RANK TENSOR IMAGING FOR MULTIDIMENSIONAL CARDIOVASCULAR MRI

(71) Applicant: Cedars-Sinai Medical Center, Los Angeles, CA (US)

(72) Inventors: Debiao Li, South Pasadena, CA (US); Anthony G. Christodoulou, Los Angeles, CA (US); Jaime Shaw, Los Angeles, CA (US); Yibin Xie, Studio City, CA (US); Christopher Nguyen, Hollywood, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/495,588

(22) Filed: Apr. 24, 2017

(65) Prior Publication Data
US 2018/0306882 A1    Oct. 25, 2018

(51) Int. Cl.
| | |
|---|---|
| *G01R 33/56* | (2006.01) |
| *A61B 5/055* | (2006.01) |
| *G06K 9/36* | (2006.01) |
| *G01R 33/561* | (2006.01) |
| *G06K 9/32* | (2006.01) |
| *G06K 9/62* | (2006.01) |
| *G06T 3/00* | (2006.01) |

(Continued)

(52) U.S. Cl.
CPC .............. *G01R 33/56* (2013.01); *A61B 5/055* (2013.01); *G01R 33/561* (2013.01); *G06K 9/3233* (2013.01); *G06K 9/36* (2013.01); *G06K 9/6249* (2013.01); *G06K 9/6256* (2013.01); *G01N 2800/32* (2013.01); *G01R 33/50* (2013.01); *G01R 33/5602* (2013.01); *G01R 33/5613* (2013.01); *G01V 3/00* (2013.01); *G06K 2209/051* (2013.01); *G06T 3/00* (2013.01)

(58) Field of Classification Search
CPC .......... G01R 33/56; G06K 9/36; A61B 5/055; G01V 3/00; G06T 3/00; G01N 2800/32
USPC ........................................................ 382/320
See application file for complete search history.

(56) References Cited

U.S. PATENT DOCUMENTS

| | | | |
|---|---|---|---|
| 6,560,353 B1 * | 5/2003 | Haacke ................ | G01R 33/561 |
| | | | 382/128 |
| 2010/0142781 A1 * | 6/2010 | Walker ................ | G01S 7/52026 |
| | | | 382/131 |

(Continued)

OTHER PUBLICATIONS

Tucker, L., "Some mathematical notes on three-mode factor analysis," Psychometrika—vol. 31, No., pp. 279-311 (Sep. 1, 1966).

(Continued)

*Primary Examiner* — Amandeep Saini
(74) *Attorney, Agent, or Firm* — Nixon Peabody LLP

(57) ABSTRACT

A new low rank tensor (LRT) imaging strategy/methodology, specifically for quantitative cardiovascular magnetic resonance (CMR) multitasking, includes performing a low-rank tensor image model exploiting image correlation along multiple physiological and physical time dimensions, a non-ECG data acquisition strategy featuring minimal gaps in acquisition and frequent collection of auxiliary subspace training data, and a factored tensor reconstruction approach which enforces the LRT model.

25 Claims, 48 Drawing Sheets

=  ×

(51) Int. Cl.
G01V 3/00 (2006.01)
G01R 33/50 (2006.01)

(56) References Cited

U.S. PATENT DOCUMENTS

2016/0232175 A1* 8/2016 Zhou .................. G06T 1/20
2018/0032128 A1* 2/2018 Baranyi ............... G06F 3/012

OTHER PUBLICATIONS

De Lathauwer, L. et al., "A multilinear singular value decomposition," Siam J. Matrix Anal. Appl., vol. 21, No. 4, pp. 1253-1278 (Apr. 18, 2000).
Stanisz, G. et al., "T1, T2 relaxation and magnetization transfer in tissue at 3T," Magnetic Resonance in Medicine 54:507-512 (Aug. 5, 2005).
Kellman, P. et al, "Multicontrast delayed enhancement provides improved contrast between myocardial infarction and blood pool," Journal of Magnetic Resonance Imaging 22:605-613 (Oct. 7, 2005).
Liang, Z., "Spatiotemporal imaging with partially separable functions," Department of Electrical and Computer Engineering, and Beckman Institute for Advance Science and Technology, University of Illinois at Urbana-Champaign, pp. 988-991 (Apr. 12, 2007).
Adluru, G. et al., "Acquisition and reconstruction of undersampled radial data for myocardial perfusion MRI," J. Magn Reson Imaging, 29(2): 466-473. doi:10,1002/jmri.21585 (Jan. 22, 2009).
Blume, U. et al., "Interleaved T1 and T2 relaxation time mapping for cardiac applications," Journal of Magnetic Resonance Imaging 29:480-487 (Jan. 22, 2009).
Pedersen, H. et al., "Temporally constrained k-t BLAST reconstruction using principal component analysis," Magnetic Resonance in Medicine 62:706-716 (Jul. 7, 2009).
Kolda, T. et al., "Tensor decompositions and applications," SIAM Review, vol. 51, No. 3, pp. 455-500 (Aug. 5, 2009).
Giri, S. et al., "T2 quantification for improved detection of myocardial edema," Journal of Cardiovascular Magnetic Resonance, pp. 1-13 (Dec. 30, 2009).
Liu, J. et al., "Respiratory and cardiac self-gated free-breathing cardiac CINE imaging with multiecho 3D hybrid radial SSFP acquisition," Magn Reson Med. May 2010; 63(5): 1230-1237 (Apr. 23, 2010).
Huang, C. et al., "T2 mapping from highly undersampled data by reconstruction of principal component coefficient maps using compressed sensing," Magn Reson Med. May 2010; 67(5): 1355-1366 (Aug. 16, 2011).
DiBella, E. et al., "Myocardial perfusion acquisition without magnetization preparation or gating," Magnetic Resonance in Medicine 67:609-613 (Dec. 21, 2011).
Liu, J. et al., "Tensor completion for estimating missing values in visual data," Arizona State University, VRVis Research Center, 8 pages (Jan. 24, 2012).
Xue, H. et al., "Phase-sensitive inversion recovery for myocardial T1 mapping with motion correction and parametric fitting," Magnetic Resonance in Medicine 69:1408-1420 (Jun. 26, 2012).
Trzasko, J. et al., "A unified tensor regression framework for calibrationless dynamic, multi-channel MRI reconstruction," Mayo Clinic, Rochester, MN, United States, Proc. Intl. Soc. Mag. Reson. Med. 21, 1 page (Jan. 1, 2013).
Von Knobelsdorff-Brenkenhoff et al., "Myocardial T1 and T2 mapping at 3T: reference values, influencing factors and implications," Journal of Cariovascular Magnetic Resonance 2013, 15:53, 11 pages (Jun. 18, 2013).
Christodoulou, A. et al., "High-resolution cardiovascular MRI by integrating parallel imaging with low-rank and sparse modeling," Ieee Trans Biomed Eng. Nov. 2013; 60(11): 3083-3092, 29 pages (Nov. 1, 2013).
Muehling, O. et al., "Regional heterogeneity of myocardial perfusion in healthy human myocardium: assessment with magnetic resonance perfusion imaging," Journal of Cardiovascular Magnetic Resonance, vol. 6, No. 2, pp. 499-5074 (Jan. 1, 2014).
Sharif, B. et al., "Non-ECG-gated myocardial perfusion MRI using continuous magnetization-driven radial sampling," Magnetic Resonance in Medicine 72:1620-1628 (Jan. 7, 2014).
Lam, F. et al., "A subspace approach to high-resolution spectroscopic imaging," Magnetic Resonance in Medicine 71:1349-1357 (Feb. 4, 2014).
Yu, Y. et al. al., "Multidimensional compressed sensing MRI using tensor decomposition-based sparsifying transform," PLOS One, www.plosone.org, Jun. 2014, vol. 9, Issue 6, e98441 (Jun. 5, 2014).
Fu, M. et al., "High-resolution dynamic speech imaging with joint low-rank and sparsity constraints," Magnetic Resonance in Medicine 73:1820-1832 (Jun. 9, 2014).
Pang, J. et al., "ECG and navigator-free four-dimensional whole-heart coronary MRA for simultaneous visualization of cardiac anatomy and function," Magnetic Resonance in Medicine 72:1208-1217 (Sep. 12, 2014).
Chen, D. et al., "Quantification of myocardial blood flow using non-ECG-triggered MR imaging," Magnetic Resonance in Medicine 74:765-771 (Sep. 16, 2014).
Kvernby, S. et al., "Simultaneous three-dimensional myocardial T1 and T2 mapping in one breath hold with 3D-QALAS," Journal of Cardiovascular Magnetic Resonance 2014, 16:102, 14 pages (Dec. 20, 2014).
Christodoulou, A. et al., "3D dynamic T1 mapping of the myocardium using a time-varying subspace," Proc. Intl. Soc. Mag. Reson. Med. 23, 1 page (Jan. 1, 2015).
Feng, L. et al., "XD—GRASP—Golden-angle radial MRI with reconstruction of extra motion-state dimensions using compressed sensing," Magnetic Resonance in Medicine 75:775-788 (Mar. 25, 2015).
Coolen, B. et al., "Three-dimensional quantitative T1 and T2 mapping of the carotid artery: Sequence design and in vivo feasibility," Magnetic Resonance in Medicine 75:1008-1017 (Apr. 28, 2015).
Akçakaya, M. et al., "Joint myocardial T1 and T2 mapping using a combination of saturation recovery and T2-preparation," Magnetic Resonance in Medicine 76:888-896 (Sep. 29, 2015).
Ma, C. et al., "High-resolution dynamic 31P-MRSI using high-order partially separable functions," Proc. Intl. Soc. Mag. Reson. Med. 24, 3 pages (Jan. 1, 2016).
Tamir, J. et al., "T2 shuffling: Sharp, multicontrast, volumetric fast spin-echo imaging," Magnetic Resonance in Medicine 77:180-195 (Jan. 20, 2016).
Hamilton, J. et al., "MR fingerprinting for rapid quantification of myocardial T1, T2, and proton spin density." Magnetic Resonance in Medicine 77:1446-1458 (Apr. 1, 2016).
He, J. et al., "Accelerated high-dimensional MR imaging with sparse sampling using low-rank tensors," IEEE Trans Med Imaging, Sep. 2016; 35(9): 2119-2129, 31 pages (Apr. 12, 2016).
Christodoulou, A. et al., "Fast dynamic electron paramagnetic resonance (EPR) oxygen imaging using low-rank tensors," Journal of Magnetic Resonance 270 (2016) 176-182 (Sep. 1, 2016).

* cited by examiner

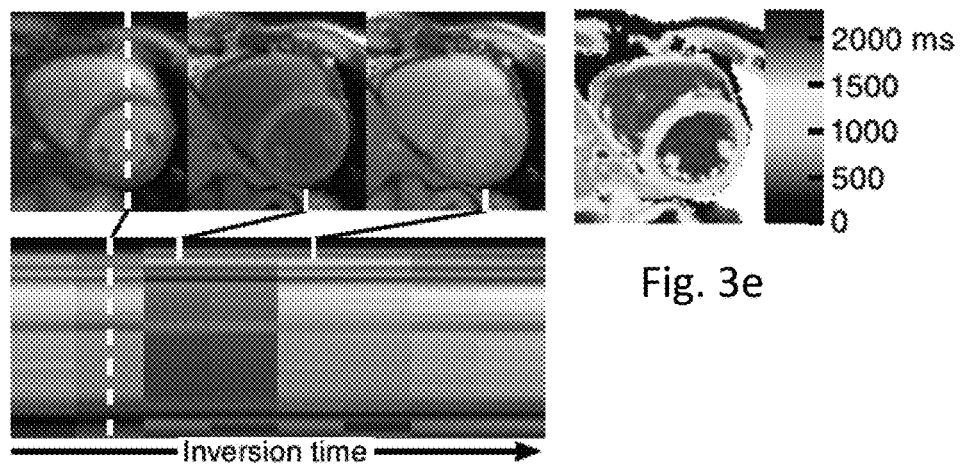
Fig. 3e
Fig. 3d
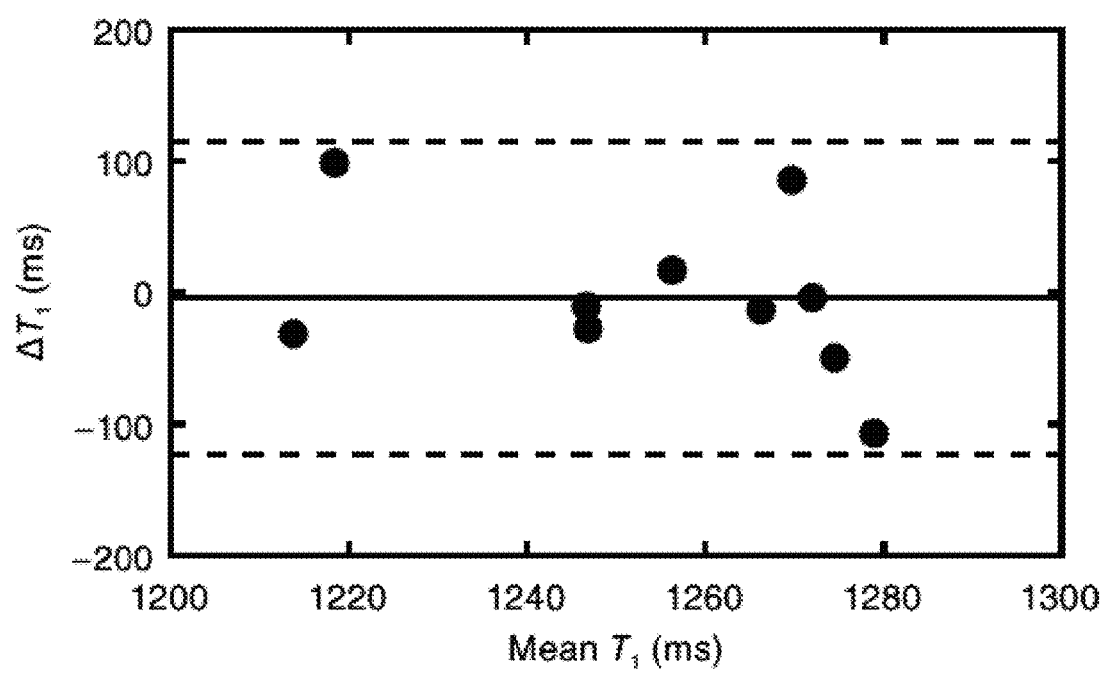
Fig. 3f

Fig. 5b  Fig. 5c
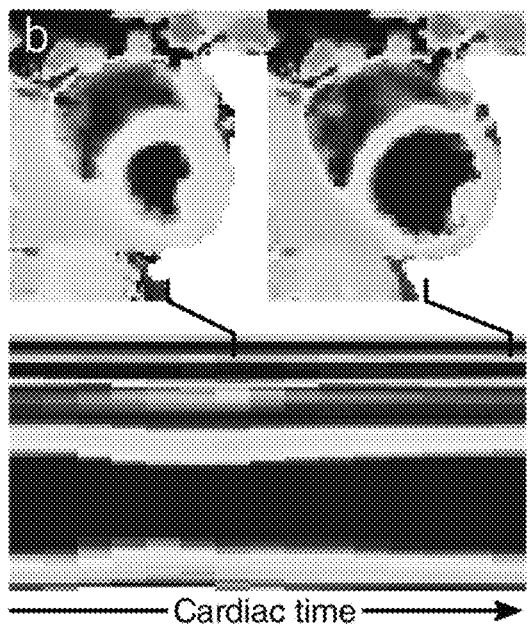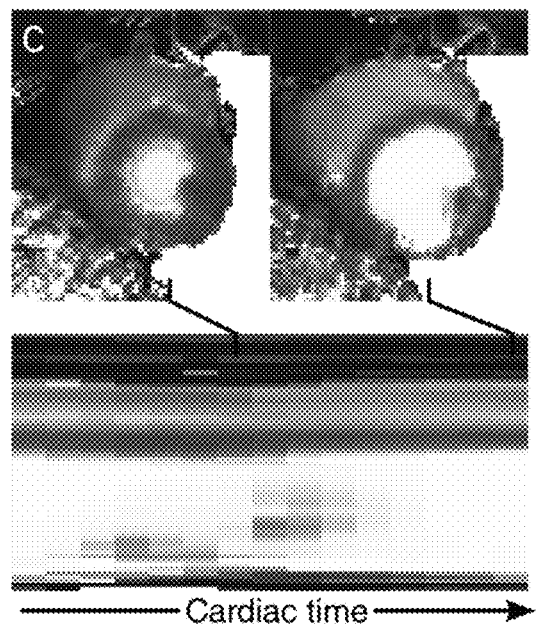
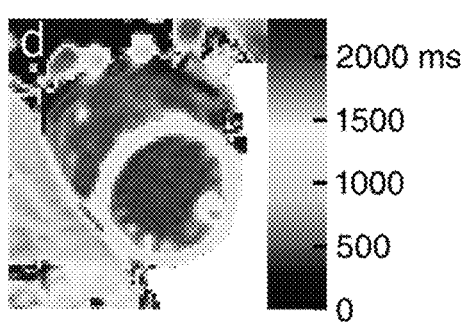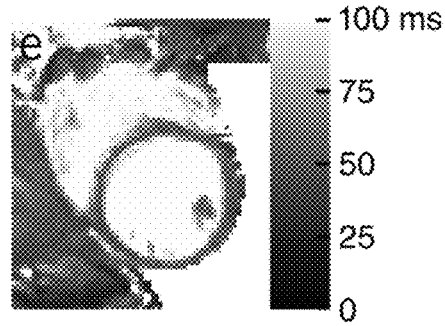
Fig. 5d  Fig. 5e

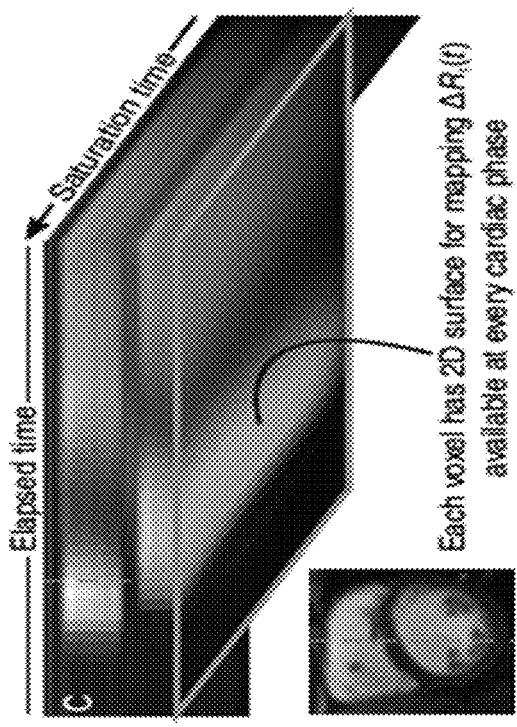
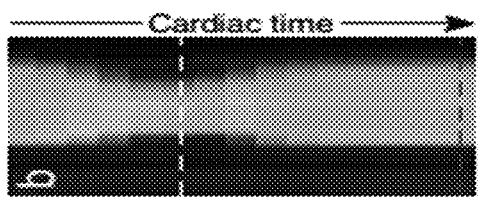
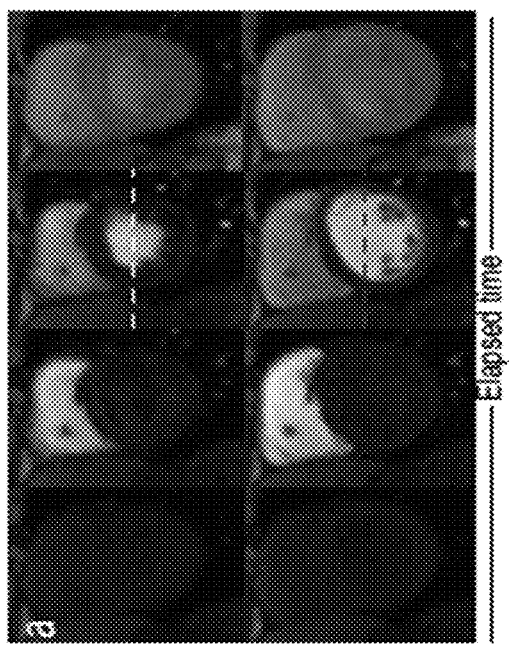
Fig. 7c
Fig. 7b
Fig. 7a

| | Subject 1 | Subject 2 |
|---|---|---|
| Age, gender | 26, Female | 53, Male |
| Application | Native T1 Mapping | First-Pass T1 Mapping |
| Sequence | Inversion recovery FLASH | Saturation recovery FLASH |
| Flip angle ($\alpha$) | 5° | 12° |
| Segments (# of $\alpha$'s between prep pulses) | 690 | 142 |
| $T_R/T_E$ | 3.56/1.64 ms | 3.33/1.58 ms |
| Recovery period | 2525 ms | 498 ms |
| Field of view | 270 mm × 270 mm | |
| Spatial matrix size | 160 × 160 | |
| Spatial resolution | 1.7 mm × 1.7 mm | |
| Slice thickness | 8 mm | |
| Tensor size | $160^2$ voxels × 345 inversion times × 15 cardiac phases × 5 respiratory phases | $160^2$ voxels × 71 recovery times × 10 cardiac phases × 77 heartbeats |
| Radial Nyquist scan time | 6.6 hours | 13 hours |
| Radial Nyquist scan time (if reduced to 8 recovery times) | 9.2 minutes | 1.5 hours |
| Actual scan time | 1 minute | 1 minute |

Fig. 10

|  | | MOLLI | | Proposed | |
|---|---|---|---|---|---|
|  |  | Myocardium | Blood | Myocardium | Blood |
| Subject 1 | Diastole | 1320.8 ± 37.5 | 1925.2 ± 87.2 | 1240.4 ± 70.7 | 2130.2 ± 36.4 |
|  | Systole | 1244.1 ± 51.1 | 1860.4 ± 56.9 | 1204.7 ± 38.5 | 1915.2 ± 71.9 |
| Subject 2 | Diastole | 1270.9 ± 58.5 | 1792.2 ± 97.9 | 1296.1 ± 56.5 | 1814.6 ± 101 |
|  | Systole | 1254.5 ± 34.9 | 1793.3 ± 44.9 | 1222.9 ± 49.5 | 1595.4 ± 59.2 |

Fig. 15

| Method | Measurement | Values | Within-subject standard deviation | Coeff. of variation |
|---|---|---|---|---|
| LRT CMR Multitasking | Mean myocardial T1 (ms) | 1054 ± 61 | 5.7 | 5.4% |
| | Mean myocardial T2 (ms) | 50 ± 7.3 | 3.5 | 6.9% |
| MOLLI | Mean myocardial T1 (ms) | 1252 ± 47 | 7.9 | 0.6% |
| T2prep-SSFP | Mean myocardial T2 (ms) | 51 ± 3.0 | 1.7 | 3.3% |

Fig. 21

| Bolus | AMBF values (mL/g/min) | Significance of difference | Within-segment standard deviation | Coeff. of variation |
|---|---|---|---|---|
| First | 1.18 ± 0.35 | p = 0.40 (NS) | 0.30 mL/g/min | 25% |
| Second | 1.23 ± 0.32 | | | |

Fig. 24

| Source | Sum of squares | Degrees of freedom | Mean squares | F | p |
|---|---|---|---|---|---|
| Segments | 0.527 | 5 | 0.105 | 0.92 | 0.47 |
| Repetition | 0.065 | 1 | 0.065 | 0.57 | 0.44 |
| Error | 10.229 | 89 | 0.115 | | |
| Total | 10.821 | 95 | | | |

| Repetition | MBF (mL/g/min) | Within-segment SD | Coef. of variation |
|---|---|---|---|
| First | 1.18 ± 0.35 | 0.30 | 25% |
| Second | 1.23 ± 0.32 | | |

| Mean±Std | qMATCH T1 | MOLLI T1 | AT1 | qMATCH T2 | T2prepSSFP | ΔT2 |
|---|---|---|---|---|---|---|
| Muscle | 1041.4±21.2 | 1142.2±20.7 | -100.8 | 30.0±0.8 | 36.8±0.7 | -6.8 |
| Blood | 1473.4±95.7 | 1792.6±173.1 | -319.2 | 95.7±7.5 | 102.0±24.2 | -6.3 |
| Vessel Wall | 1181.7±18.3 | N/A | N/A | 58.4±9.6 | N/A | N/A |

Fig. 39

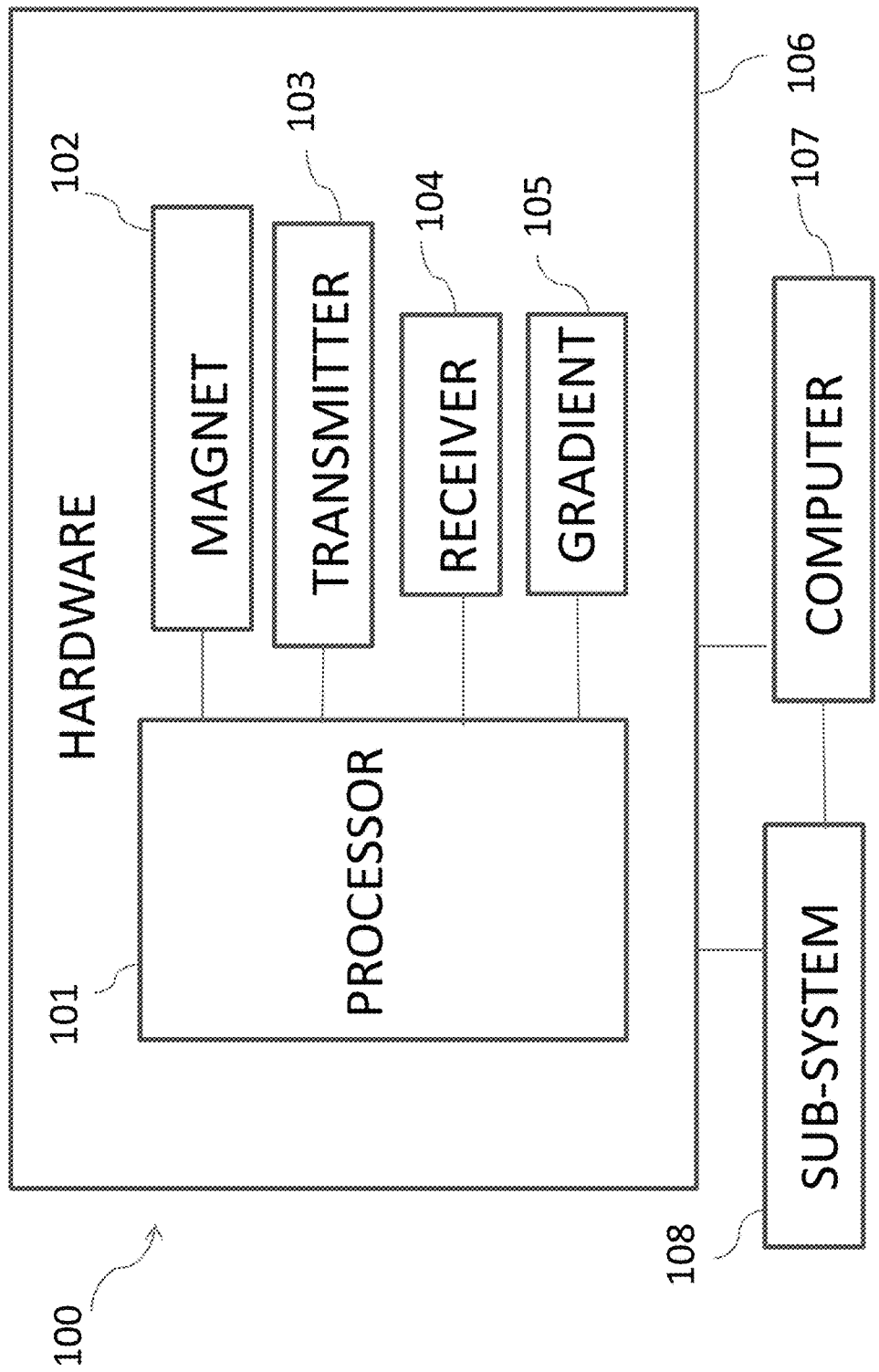

_US 10,436,871 B2_

LOW-RANK TENSOR IMAGING FOR MULTIDIMENSIONAL CARDIOVASCULAR MRI

STATEMENT REGARDING FEDERALLY SPONSORED RESEARCH OR DEVELOPMENT

This invention was made with government support under Grant Nos. HL116273 and HL124649 awarded by the National Institutes of Health. The government has certain rights in the invention.

FIELD OF THE INVENTION

The present invention relates to cardiovascular magnetic resonance imaging (MRI), and more specifically to apparatus and methods for low-rank tensor imaging in multidimensional cardiovascular MRI.

BACKGROUND

Quantitative cardiovascular MR (CMR) imaging has the potential to perform a wide range of diagnostic measurements in the heart, providing reproducible, accurate assessments of heart function and anatomy for diagnosis and monitoring of cardiovascular diseases in humans and in animal models. For example, quantification of the NMR relaxation constants $T_1$ and $T_2$ is promising for cardiovascular tissue characterization, revealing fibrosis, edema, inflammation, and more. Further, quantification of myocardial blood flow (MBF) through myocardial perfusion imaging is promising for diagnosing ischemia and coronary artery disease. However, imaging in the presence of various overlapping dynamics—both physiological (e.g., cardiac and respiratory motion) and physical (e.g., $T_1$ and $T_2$ relaxation)—is a major technical challenge which has prevented widespread adoption of quantitative CMR.

The conventional strategy to handle the overlapping dynamics involved in cardiovascular imaging has been to apply a complicated mixture of ECG control, breath holding, and/or short acquisition bursts to "freeze" as many dynamics as possible during data acquisition. This typically means choosing one dynamic at a time, forgoing useful information about the remaining dynamics and requiring pauses in between acquisition bursts. As a result, the standard cardiac exam consists of a prolonged, inefficient sequence of scans, each of which applies a different combination of freezing mechanisms targeting different dynamics. Furthermore, these freezing mechanisms can be unreliable (e.g., ECG triggering) or uncomfortable (e.g., breath holds), and the use of multiple breath holds results in misalignment between scans, complicating image fusion for comprehensive analysis. More importantly, this overall strategy does not work properly for particularly unhealthy subjects who have cardiac arrhythmias or difficulty holding their breath. Accordingly, there is a need for addressing the overlapping dynamics in cardiovascular imaging so as to make quantitative CMR feasible.

SUMMARY

The various embodiments are directed to systems and methods for cardiovascular MRI imaging using a low-rank tensor methodology.

In a first embodiment, a method for performing magnetic resonance imaging (MRI) on a subject is provided. The method includes obtaining a temporal factor tensor for a region of interest in the subject, acquiring sparsely sampled imaging data for the region of interest, estimating a spatial factor matrix for the region of interest based on the sparsely sampled imaging data and the temporal factor tensor, and reconstructing a complete image for the region of interest by combining the spatial factor matrix and the temporal factor tensor.

In the method, the obtaining can include acquiring data at a subset of the spatial encodings for the region of interest (i.e., with partial spatial encoding), calculating a training tensor representing the complete imaging data for the subset of spatial encodings; and extracting the temporal factor tensor from the training tensor. The extracting can include decomposing the training tensor into a partially-encoded spatial factor matrix, a full core tensor, and temporal basis matrices, followed by calculation of the temporal factor tensor as the product of the core tensor and the temporal basis matrices.

In the method, the estimating can include fitting the temporal factor tensor to the sparsely sampled imaging data to obtain the spatial factor matrix.

In the method, the temporal factor tensor can be calculated as the product of a core tensor and one or more temporal basis matrices, each of the temporal basis matrices corresponding to a different time dimension. Each time dimension can be one of cardiac phase, respiratory phase, elapsed time, imaging sequence parameters, or timing parameters.

In the method, the k-space locations for the training data correspond to k-space locations for identifying at least one of cardiac phases or respiratory phases for the subject. The subject can be a mammal. Also, the subject can be a human.

In second embodiment, there is provided a magnetic resonance imaging (MRI) system. The MRI system includes a magnet operable to provide a magnetic field, a transmitter operable to transmit to a region within the magnetic field, a receiver operable to receive a magnetic resonance signal from the region, and a processor operable to control the transmitter and the receiver. The processor is configured to direct the transmitter and receiver to execute a sequence. The sequence includes obtaining a temporal factor tensor for a region of interest in a subject, acquiring sparsely sampled imaging data for the region of interest, estimating a spatial factor matrix for the region of interest based on the sparsely sampled imaging data and the temporal factor tensor, and reconstructing a complete image for the region of interest by combining the spatial factor matrix and the temporal factor tensor.

In the MRI system, the obtaining includes repeatedly acquiring data at a subset of the spatial encodings for the region of interest, calculating a training tensor representing the complete imaging data at this subset of spatial encodings, and extracting the temporal factor tensor from the full training tensor. The extracting can include comprises decomposing the training tensor into a partially-encoded spatial factor matrix, a full core tensor, and full temporal basis matrices, followed by calculation of the temporal factor tensor as the product of the core tensor and temporal basis matrices.

In the MRI system, the estimating includes fitting the temporal factor tensor to the sparsely sampled imaging data to obtain the spatial factor matrix. The temporal factor tensor can be calculated as the product of a core tensor and one or more temporal basis matrices, each of the temporal basis matrices corresponding to a different time dimension. Each time dimension can be one of cardiac phase, respiratory phase, elapsed time, imaging sequence parameters, or timing parameters.

In the MRI system, the k-space locations for the training data can correspond to k-space locations for identifying at least one of cardiac phases or respiratory phases for the subject. The subject can be a mammal. Further, the subject can be a human.

In a third embodiment, there is provided a non-transitory machine-readable medium having machine executable instructions for causing one or more processors of a magnetic resonance imaging (MRI) machine to execute the imaging method of the first embodiment.

BRIEF DESCRIPTION OF THE DRAWINGS

FIGS. 3a, 3b, 3c, 3d, 3e, and 3f show results for CMR multitasking for non-ECG, free-breathing native myocardial $T_1$ mapping.

FIGS. 5a, 5b, 5c, 5d, 5e, and 5f show CMR multitasking for non-ECG, free-breathing joint $T_1$-$T_2$ mapping in the myocardium.

FIGS. 7a, 7b, 7c, and 7d show CMR multitasking for non-ECG, first-pass myocardial perfusion $T_1$ mapping.

FIG. 10 shows a set of parameters for a radial sequence.

FIG. 15 shows $T_1$ values for the septal myocardium from an ungated, free-breathing method according to an embodiment and MOLLI 5(3)3 from two healthy subjects.

FIG. 21 shows a table that summarizes statistical findings from the three methods used for FIG. 20.

FIG. 24 shows a table listing measurement statistics aggregated over segments.

FIG. 29a shows the two-way ANOVA table indicating a nonsignificant difference (p=0.44) between repetitions as well as a nonsignificant difference (p=0.47) between segments.

FIG. 29b lists repeatability statistics aggregated over segments.

FIG. 39 shows a table for comparison between the in vivo T1 and T2 mapping results from qMATCH and 2D reference methods (MOLLI and T2prep SSFP).

FIG. 40 depicts a system in accordance with various embodiments of the invention.

DETAILED DESCRIPTION

Figure 1:
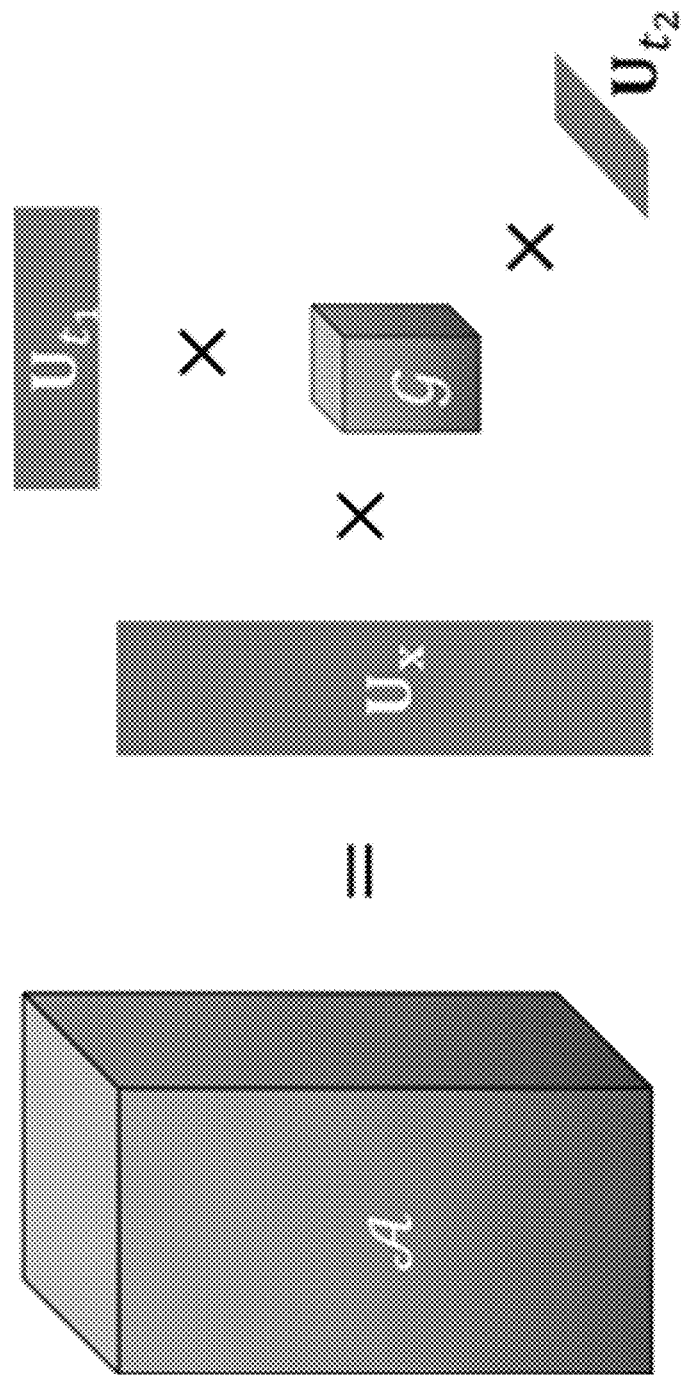
FIG. 1 shows a conceptual illustration of Tucker factorization of a low-rank 3-way tensor.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Quantitative cardiovascular magnetic resonance (CMR) imaging is desirable for reproducible characterization of fibrosis, edema, ischemia, inflammation, and more. However, the dominant strategy for performing CMR typically involves a complicated mixture of ECG and respiratory control, limiting the practicality and applicability of CMR. In view of such limitations, the present disclosure contemplates a new framework, CMR multitasking, for conceptualizing different sources of motion and other image dynamics as different time dimensions and for resolving the multiple time dimensions (or "tasks") through the application of low-rank tensor imaging. By capturing—rather than avoiding—motion, relaxation, and other dynamics, CMR multitasking can efficiently perform quantitative CMR without the use of ECG triggering, breath holds, etc. Such CMR multitasking enables several of new capabilities: non-ECG, free-breathing T1 mapping; non-ECG, free-breathing T1-T2 mapping; and non-ECG, time-resolved T1 mapping for myocardial perfusion and dynamic contrast enhancement imaging.

As noted above, the goal of CMR multitasking is to simultaneously resolve the many overlapping dynamics involved in cardiovascular imaging. As described in greater detail below, CMR multitasking conceptualizes different sources of image dynamics as different time dimensions. In the various embodiments, these multiple time dimensions (or "tasks") are resolved through a low-rank tensor (LRT) imaging method specifically designed to address the unique challenges of cardiovascular imaging. By using the CMR multitasking methodology described herein, one can capture (rather than avoid) motion, relaxation, and other dynamics. As a result, it becomes possible to perform quantitative CMR without the use of ECG triggering, breath holds, etc. Such a methodology therefore provides a more efficient, reliable, and comfortable imaging framework solves several long-standing problems in CMR. Moreover, the CMR multitasking methodology described herein is applicable even to those patients who would have difficulty receiving a conventional CMR exam.

As described above, the present disclosure contemplates that CMR multitasking can be achieved in the various embodiments via the use of low rank tensor (LRT) imaging.

The power of LRT imaging lies in the exceptional scalability of low-rank tensors: the degrees of freedom (and therefore the required scan times) scale linearly with the number of dimensions rather than exponentially[1]. As a result, multidimensional imaging with at least four time dimensions can be achieved. Earlier cardiovascular imaging methods based on other models (e.g., temporal smoothness models[2], deformable respiratory motion models[3], and sparse temporal finite-difference models[4,5]) have been demonstrated for two time dimensions (typically cardiac and respiratory motion). However, these are typically too few for non-ECG free-breathing quantitative CMR.

Although low-rankness has been previously for some MRI applications, such imaging has involved only one time dimension[6-11] and there has so far been only limited exploration of low-rank tensors for higher dimensional MRI[12-17]. However, CMR multitasking provides unique challenges that prevent direct application of previous multidimensional LRT imaging approaches. One issue with previous approaches is that physiological time dimensions cannot be precisely sampled without ECG and respiratory control—precluding approaches requiring specific sampling patterns[14-17]. Another issue with previous approaches is that large tensor sizes prevent unfactored tensor recovery[12,13].

In view of the forgoing, the present disclosure describes a new LRT imaging strategy/methodology, specifically for CMR multitasking. This methodology includes performing:

1) a low-rank tensor image model exploiting image correlation along multiple physiological and physical time dimensions;
2) a non-ECG data acquisition strategy featuring minimal gaps in acquisition and frequent collection of auxiliary subspace training data; and
3) a factored tensor reconstruction approach which enforces the LRT model in two efficient steps: (a) determine the temporal factors of the model and (b) determine the spatial factors.

The new capabilities enabled by CMR multitasking include, but are not limited to: non-ECG, free-breathing $T_1$ mapping in the myocardium; non-ECG, free-breathing joint $T_1$-$T_2$ mapping in the myocardium and the carotid arteries; and non-ECG, time-resolved $T_1$ mapping during dynamic contrast enhancement (DCE), covering first-pass myocardial perfusion $T_1$ mapping as well as DCE $T_1$ mapping in the carotids.

Imaging Framework

CMR multitasking represents a set of cardiovascular images as a multidimensional tensor (or array) with one dimension indexing voxel location (i.e., combining the spatial dimensions) and the others indexing N different time dimensions, each corresponding to a different "task" or dynamic to be imaged (e.g., $T_1$ recovery, $T_2$ decay, cardiac motion, respiratory motion, and/or contrast agent dynamics). Correlation between images is described and exploited by modeling this tensor as low-rank[6], reducing the images to the product of a small core tensor and N+1 factor matrices[1] (See, e.g., FIG. 1). These model components have far fewer elements than the total number of elements in the images, reducing data acquisition requirements and allowing highly accelerated scans. Data can be acquired by interleaving sparsely sampled image data with auxiliary subspace training data that frequently samples a subset of k-space. A novel memory- and time-efficient factored approach can then be used for image reconstruction, wherein the core tensor and N temporal basis matrices are estimated from the subspace training data. The spatial factor matrix can then be recovered by fitting the core tensor and temporal basis matrices to the remainder of the measured data.

Image Model

CMR multitasking represents a cardiovascular image as a multidimensional function $I(x, t_1, t_2, \ldots, t_N)$ of spatial location x and of N time dimensions $t_1, t_2, \ldots, t_N$. Each time dimension corresponds to a different "task" or dynamic to be resolved; example time dimensions correspond to cardiac motion, respiratory motion, sequence timing parameters (useful for encoding $T_1$ and $T_2$), and time elapsed since the start of imaging (useful for depicting the passage of contrast agent through tissue). The image I can be represented in discretized form as an (N+1)-way tensor (or array) $\mathcal{A}$ with elements $A_{jkl\ldots q}=I(x_j, t_{1,k}, t_{2,l}, \ldots, t_{N,q})$, where the first tensor dimension indexes the set of J voxel locations $\{x_j\}_{j=1}^{J}$ and each other tensor dimension indexes one of the time dimensions (e.g., if $t_1$ corresponds to cardiac motion, then $\{t_{1,k}\}_{k=1}^{K}$ indexes K cardiac phases). Recovery of the entire tensor $\mathcal{A}$ at the Nyquist sampling rate would be subject to the curse of dimensionality, wherein the number of samples required increases exponentially with the number of dimensions being imaged, leading to impractical scan times. However, scan time can be heavily reduced by exploiting the spatiotemporal correlation across the image function[6], specifically by modeling the tensor $\mathcal{A}$ as low-rank, such that the degrees of freedom in $\mathcal{A}$ increase linearly rather than exponentially[1]. One can employ the Tucker form[18] of the low-rank tensor decomposition, which reduces $\mathcal{A}$ to the product of a core tensor and N+1 basis matrices, $$\mathcal{A} = G \times_1 U_x \times_2 U_{t_1} \times_3 U_{t_2} \times_4 \ldots \times_{(N+1)} U_{t_N}, \quad (1)$$

where the $\times_i$ operator denotes the ith mode product[1], the factor matrix $U_x \in \mathbb{C}^{J \times L_0}$ contains $L_0$ spatial basis functions (or basis images) with J voxels each, each factor matrix $U_{t_i}$ contains $L_i$ basis functions for the ith time dimension $t_i$ (e.g., $U_{t_1} \in \mathbb{C}^{K \times L_1}$ contains $L_1$ temporal basis functions of length K), and where $g \in \mathbb{C}^{L_0 \times L_1 \times \ldots \times L_N}$ is the core tensor governing the interaction between factor matrices (See FIG. 1). The factor matrices and core tensor have far fewer elements than the total number of elements in $\mathcal{A}$, reducing sampling requirements and allowing highly accelerated scanning.

Outline of Sampling and Reconstruction

Based on the foregoing, a general methodology for sampling and reconstruction of the image tensor $\mathcal{A}$, thus the image, is as follows:

(a) Acquire training data. That is, acquire a subset of imaging data from a portion of k-space (i.e., with only partial spatial encoding). For example, a repeated scan of one or more lines, spirals, cones, or other portion of k-space. The temporal characteristics of this subset (e.g., a temporal sampling rate high enough to resolve the motions of interest) are more important than its spatial encoding characteristics (i.e., it does not have to satisfy spatial Nyquist or resolution requirements).

(b) Calculate the training tensor from the training subset of the imaging data. In the event the training data do not contain measurements from every combination of time points, the assembled training tensor is considered incomplete (e.g., unfilled slots remain when the data in the tensor is slotted) tensor completion methods can then be applied to generate any missing portions of the tensor. As the subset represents a limited set of data, the computational requirements for completing the tensor are relatively low and the training tensor can be reconstructed with a relatively low computing cost.

(c) Extract the temporal factor tensor. As noted herein, an image can be expressed as a tensor consisting of the product of a spatial factor matrix, a core tensor, and temporal basis matrices. The training tensor from a partial subset of k-space is decomposed into a partially-encoded spatial factor matrix, the core tensor, and the temporal basis matrices. The product of the core tensor and temporal basis matrices is retained as the temporal factor tensor.

(d) Obtain sparsely sampled image data for the region of interest. The spatial encoding characteristics of these data are more important than their temporal characteristics: generally, it should cover k-space in a manner appropriate for the desired spatial coverage and spatial resolution but need not do so quickly enough to resolve the temporal dynamics of interest. The training data and the sparsely sampled image data can be acquired concurrently. Further, both can be collected continuously without physiological triggering.

(e) Estimate the spatial factor matrix. Using the sparsely sampled image data and the temporal factor tensor, the spatial factor matrix is reconstructed. For example, this can be done by fitting the temporal factor tensor to the sparsely sampled imaging data. This step is not limited to direct least-squares fitting: e.g., regularization penalties can be incorporated in order to enforce complementary image models.

(f) Generate an image for the region of interest by assembling the image tensor. The image tensor for the region of interest can reconstructed by taking the product of the estimated spatial factor matrix and the temporal factor tensor. If only certain time points are of interest, the image tensor can be generated using only subsets of the temporal factor tensor to save memory.

Detailed Sampling and Reconstruction

It is useful to express Eq. (1) in matrix form as $$A_{(1)} = U_x G_{(1)} (U_{t_N} \otimes U_{t_{N-1}} \otimes \ldots \otimes U_{t_1})^T, \quad (2)$$

where subscript (n) denotes mode-n unfolding or flattening of the tensor into a matrix[1] and the $\otimes$ operator denotes the Kronecker product. With this form, the multichannel MR signal d from tensor $\mathcal{A}$ is expressed as $d = \Omega(FSA_{(1)})$, where S applies coil sensitivity maps to $A_{(1)}$, where F applies the appropriate spatial encoding operator (most commonly the Fourier encoding operator that transforms x-space to k-space), and where $\Omega(\cdot)$ is the sampling operator corresponding to samples acquired and collected in the vector d. The image tensor $\mathcal{A}$ can then be reconstructed by low-rank tensor completion[19], for example, $$\hat{\mathcal{A}} = \underset{\mathcal{A}}{\arg\min} \|d - \Omega(FSA_{(1)})\|_2^2 + \lambda \sum_{n=1}^{N+1} \|A_{(n)}\|_* + R(\mathcal{A}), \quad (3)$$

where $\lambda$ is the rank regularization parameter, $\|\cdot\|_*$ denotes the matrix nuclear norm, and where $R(\cdot)$ is an optional additional regularization functional.

Practical considerations can prevent image reconstruction per Eq. (3), especially when $\mathcal{A}$ contains many dimensions. Although the low-rank tensor model frees sampling requirements from the curse of dimensionality, the size of $\mathcal{A}$ is still subject to exponential growth. As a result, the memory requirements of storing $\mathcal{A}$ in uncompressed form alongside the N+1 identically-sized auxiliary variables potentially involved in solving Eq. (3) via singular value decomposition (SVD) thresholding are prohibitive. Furthermore, each iteration of the image reconstruction algorithm could involve operations on every column of $A_{(1)}$—which can number in the hundreds of thousands—as well as N+1 SVDs of large matrices, all at significant computational expense.

For these reasons, one can propose to instead reconstruct A in factored form using an explicit tensor subspace constraint[14]:

$$\hat{U}_x = \underset{U_x}{\arg\min} \|d - \Omega([FSU_x]\Phi)\|_2^2 + R(U_x), \quad (4)$$

where $\Phi = G_{(1)}(U_{t_N} \otimes U_{t_{N-1}} \otimes \ldots \otimes U_1)^T$. Eq. (4) allows compressed storage of $A_{(1)}$, requires application of FS only to the $L_0$ columns of $U_x$, and avoids SVDs of large matrices. This does, however, require pre-knowledge of $\Phi$, which we propose to determine from subspace training data collected frequently throughout the scan at a small subset of k-space locations. An auxiliary $(k, t_1, t_2, \ldots, t_N)$-space tensor $\mathcal{D}_{tr}$ is recoverable by a low-rank tensor completion problem much less expensive than the one previously seen in Eq. (3):

$$\hat{\mathcal{D}}_{tr} = \underset{\mathcal{D}_{tr}}{\arg\min} \|d_{tr} - \Omega_{tr}(\mathcal{D}_{tr})\|_2^2 + \lambda \sum_{n=1}^{N+1} \|D_{tr(n)}\|_* + R(\mathcal{D}_{tr}), \quad (5)$$

where $d_{tr}$ is the subset of measured data used for subspace training and where $\Omega_{tr}(\cdot)$ retains only the training samples. Note that Eq. (5) requires no Fourier transforms and involves smaller matrices than Eq. (3). The required matrix $\Phi$ can then be quickly extracted from $\hat{\mathcal{D}}_{tr}$, for example by truncating the SVD of $\hat{D}_{tr,(1)}$ or the higher-order SVD (HOSVD)[20] of $\hat{\mathcal{D}}_{tr}$. Collection of the subspace training data $d_{tr}$ is similar to the collection of self-gating lines, and as such can additionally be used for cardiac and respiratory phase identification; alternatively, data collected using this strategy can be preliminarily reconstructed as real-time images (e.g., using explicit-subspace low-rank matrix imaging with only one time dimension representing elapsed time[21]) for image-based cardiac and respiratory phase identification.

Depending on the application, the temporal basis functions for some time dimensions can be pre-determined even before any data is collected. Consider the example where $T_1$ relaxation corresponds to the Nth time dimension, $t_N$. Because $T_1$ relaxation is physically governed by the well-known Bloch equations, a dictionary of physically feasible signal curves can be readily generated ahead of time. The SVD of this dictionary yields the factor matrix $U_{t_N}$, the component of $\Phi$ that contains relaxation basis functions. In this scenario, Eq. (5) can be adapted to be partially constrained by the Bloch equations via the available $U_{t_N}$:

$$\hat{\mathcal{D}}_{tr} = \underset{\mathcal{D}_{tr} \in \Psi}{\arg\min} \|d_{tr} - \Omega_{tr}(\mathcal{D}_{tr})\|_2^2 + \lambda \sum_{n=1}^{N} \|D_{tr(n)}\|_* + R(\mathcal{D}_{tr}), \quad (6)$$

where $\Psi$ is a tensor subspace defined from the columns of $U_{t_N}$.

In various embodiments also include a magnetic resonance imaging (MRI) system configured for performing the methods described herein. The MRI system can includes (1) a magnet operable to provide a magnetic field; (2) a transmitter operable to transmit to a region within the magnetic field; (3) a receiver operable to receive a magnetic resonance signal from the region; (4) a processor operable to control the transmitter and the receiver; and (5) a non-transitory computer-readable medium. In some embodiments, the processor is configured to direct the transmitter and receiver to execute a sequence encoded on the non-transitory computer-readable medium that includes the steps of (a) utilizing the MRI scanner to apply readout pulses to acquire imaging data from the ROI continuously, and (c) obtaining raw data from the scanner. In some embodiments, the readout pulses are any of the readout pulses described above and in the "Examples" section. In some embodiments, the system further includes a computing device suitable to reconstruct the image from the raw data according to the methods described herein. In some embodiments, the computing device is an offline workstation. In some embodiments, the ROI includes an entire heart of a subject, along with multiple coronary blood vessels associated therewith. In some embodiments, the blood vessels include one or more coronary arteries (e.g., as described herein). In some embodiments, the offline workstation is utilized in conjunction with a workstation directly associated with the MRI scanner in order to accomplish parallel processing. In some embodiments, multiple offline workstations are employed in order to further accelerate parallel processing. In some embodiments, the subject is a human. In certain embodiments, the MRI system is a 1.5 T system, a 3.0 T system, a 7.0 T system, but one of skill in the art would readily appreciate that an MRI system of any appropriate strength could be used.

The various embodiments also include a non-transitory machine-readable medium having machine executable instructions for causing one or more processors of a magnetic resonance imaging (MRI) machine/scanner, and/or a subsystem configured to function therewith, to execute an imaging method, said method including: performing the methods described herein for imaging within a region of interest (ROI) that includes all or a portion of a subject's heart. In some embodiments, the ROI can also include blood vessels, such as coronary arteries. In certain embodiments, the imaging parameters are within the range of imaging parameters described herein. In some embodiments, the subject is a human.

One of skill in the art would also readily appreciate that several different types of imaging systems could be used to perform the inventive methods described herein. Merely by way of example, the imaging systems described in the examples could be used. FIG. 40 depicts a view of a system 100 that can be used to accomplish the inventive methods. System 100 includes hardware 106 and computer 107. Hardware 106 includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103 can represent a radio frequency transmitter, a power amplifier, and an antenna (or coil). Receiver 104, as denoted in the figure, can represent a receiver antenna (or coil) and an amplifier. In the example shown, transmitter 103 and receiver 104 are separately represented, however, in one example, transmitter 103 and receiver 104 can share a common coil. Hardware 106 includes gradient 105. Gradient 105 can represent one or more coils used to apply a gradient for localization.

Processor 101, in communication with various elements of hardware 106, includes one or more processors configured to implement a set of instructions corresponding to any of the methods disclosed herein. Processor 101 can be configured to implement a set of instructions (stored in memory of hardware 106 or sub-system 108) to provide RF excitation and gradients and receive magnetic resonance data from a region of interest. Sub-system 108 can include hardware and software capable of facilitating the processing of data generated by hardware 106, in conjunction with, or as a substitute for, the processing associated with image reconstruction that is normally handled by processor 101 in an MRI machine. One of skill in the art would readily appreciate that certain components of the imaging systems described herein, including the processor 101 and/or sub-system 108, are used to execute instructions embedded on a computer readable medium to implement the inventive data acquisition and image reconstruction methods described herein.

In some embodiments, computer 107 is operably coupled to hardware 106 and sub-system 108. Computer 107 can include one or more of a desktop computer, a workstation, a server, or a laptop computer. In one example, computer 107 is user-operable and includes a display, a printer, a network interface or other hardware to enable an operator to control operation of the system 100.

EXAMPLES

The examples shown here are not intended to limit the various embodiments. Rather they are presented solely for illustrative purposes.

Example 1: $T_1$ Mapping Experiments

Quantification of the spin-lattice relaxation time constant $T_1$ can characterize myocardial tissue, detecting and measuring fibrosis, protein deposition, fat infiltration, and extracellular volume fraction (when used in conjunction with a gadolinium-based contrast agent), among other biologically and clinically relevant processes and measurements. $T_1$ mapping is performed by collecting multiple images with different $T_1$ contrast weightings from which a spatial map of $T_1$ values are then calculated. Current myocardial $T_1$ mapping techniques rely on ECG synchronization and breath holding as a means of isolating the effects of $T_1$ relaxation. CMR multitasking eliminates the need for ECG and respiratory control, measuring a heart-rate-independent set of contrasts, and enables $T_1$ cine maps (i.e., cardiac-resolved $T_1$ maps).

Figure 2:
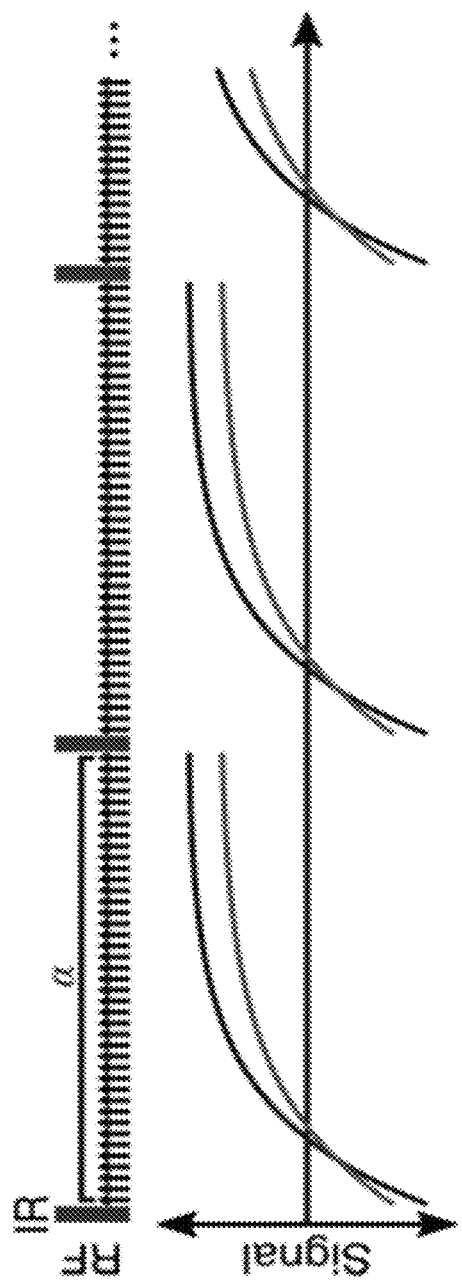
FIG. 2 shows a diagram of continuous-acquisition IR-FLASH acquisition. Illustrative signal curves are shown for two tissues with different $T_1$ values.

For native myocardial $T_1$ mapping, the multitasking sequence generated $T_1$ contrast by applying an IR magnetization preparation pulse every 2.5 s followed by 5° FLASH readouts ($T_R$=3.6 ms, $T_E$=1.6 ms) throughout the entire recovery period (See FIG. 2), with odd-numbered readouts following a golden-angle radial sampling schedule and even-numbered readouts collecting training data from the 0° radial spoke. A total of 24 IR pulses were applied for a total scan time of 60 s. The scan was free-running (i.e., continual-acquisition) with no ECG synchronization. Three time dimensions were used, representing cardiac motion (15 cardiac phases), respiratory motion (5 respiratory phases), and $T_1$ recovery (344 inversion times). The 344 inversion times represent half of the 688 total inversion times, corresponding to the golden-angle radial readout times. The use of this high number of inversion times (as opposed to a more typical number such as eight[22]) avoids the temporal blurring which would result from grouping neighboring radial acquisitions with different $T_1$-weightings. A dictionary of 31,815 IR-FLASH signal curves was generated from the Bloch equations according to $$A \frac{1 - e^{-T_R/T_1}}{1 - e^{-T_R/T_1} \cos\alpha}[1 + (B-1)(e^{-T_R/T_1}\cos\alpha)^n]\sin\alpha, \quad (7)$$

where the amplitude A absorbs proton density, $T_2^*$ weighting, and receive coil sensitivity, where n is the readout index, $\alpha$ is the FLASH flip angle, and B=$\cos \alpha_{prep}$, where is $\alpha_{prep}$ is the preparation pulse flip angle (ideally 180° for inversion recovery). The dictionary was generated for 101 $T_1$ values logarithmically spaced from 100 ms and 3 s, 15 $\alpha$ values in half-degree increments from 0.5° to 7.5° (addressing $B_1$ transmit inhomogeneity for the FLASH pulses), and 21 B values linearly spaced from −1 to −0.5 (addressing $B_1$ transmit inhomogeneity for the preparation pulse as well as a potentially incomplete approach to steady-state); five $T_1$ relaxation basis functions were defined from the SVD of this dictionary. The training data $\mathcal{D}_{tr}$ were then completed per Eq. (6) using a temporal total variation regularization (TV) functional along the cardiac and respiratory dimensions[23] for R(·), Φ was defined from the SVD of $\hat{D}_{tr,(1)}$ using $L_0$=32, and $\hat{U}_x$ was calculated per Eq. (4) using a spatial TV regularization functional for R(·). After image reconstruction, voxel-wise $T_1$, A, $\alpha$, and B were fit from Eq. (7).

To evaluate the accuracy and repeatability of native myocardial $T_1$ mapping using CMR multitasking, n=10 healthy human volunteers were recruited. Three scans each were collected of: diastolic $T_1$ maps from ECG-triggered, breath-held SSFP MOLLI 5(3)3; and cardiac- and respiratory-resolved $T_1$ maps from the proposed non-ECG, free-breathing multitasking method. One mid-ventricular short-axis slice with 1.7 mm in-plane spatial resolution and 8 mm slice thickness was imaged using each method; mean septal $T_1$ values were compared at end-diastole and end-expiration. Repeatability of each method was assessed by the coefficient of variation (CoV), calculated as the root-mean-square (RMS) within-subject standard deviation (WSSD) divided by the population mean.

Figure 3A:
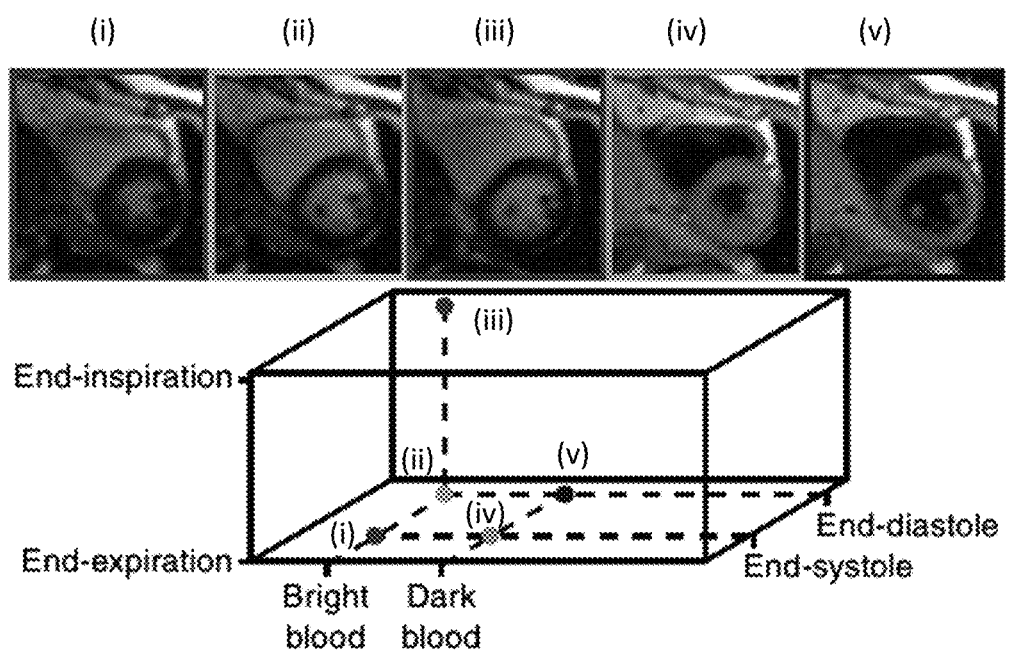
Figures 3B, 3C:
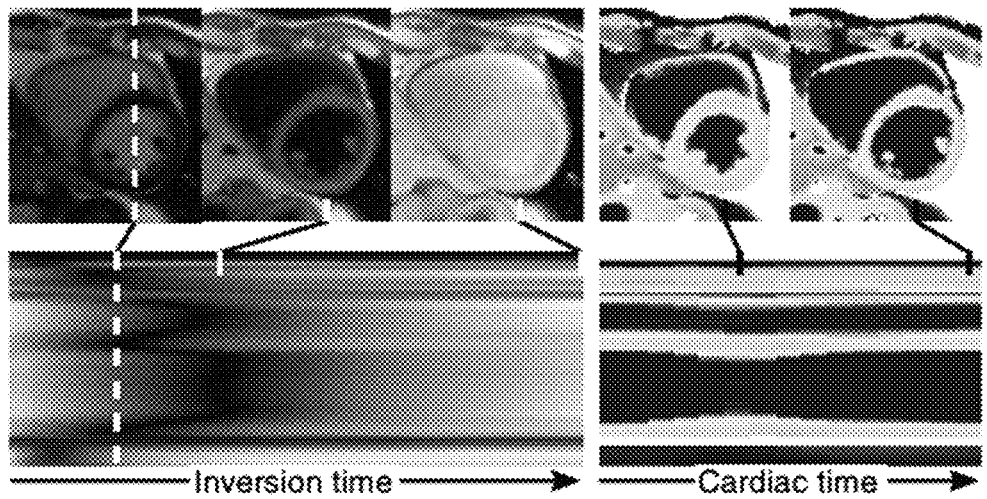

FIGS. 3a-3f show results for CMR multitasking for non-ECG, free-breathing native myocardial $T_1$ mapping. FIG. 3a shows locations of different images in a space with three time dimensions. Different $T_1$ weightings lie along the inversion time axis (horizontal), different cardiac phases lie along the cardiac time axis (depth), and different respiratory phases lie along the respiratory time axis (vertical). FIG. 3a shows CMR multitasking yields finely resolved contrast variation along the inversion time dimension, and produces (as shown in FIG. 3c) cardiac-resolved $T_1$ maps. FIG. 3d shows how MOLLI 5(3)3 relies on ECG-triggering and breath-holding to image eight heart-rate dependent inversion times, and produces (as shown in FIG. 3e) a static $T_1$ map. FIG. 3f shows a Bland-Altman plot of diastolic myocardial $T_1$ values from CMR multitasking and MOLLI in healthy subjects.

MOLLI imaged eight heart-rate-dependent inversion times at the end-diastole cardiac phase and end-expiration respiratory phase; the resulting eight images were used to produce a $T_1$ map (FIGS. 3d-e). The CMR multitasking method applied an inversion recovery (IR)-prepared fast low-angle shot (FLASH) sequence and imaged three time dimensions, measuring 344 heart-rate-independent inversion times up to 2.5 s (avoiding view sharing of data from different inversion times) for 15 cardiac phases and five respiratory phases (FIGS. 3a-c). This resulted in a total of 344*15*5=25,800 images from one minute of data acquisition. $T_1$ maps were then calculated for the end-diastolic cardiac phase and end-expiration respiratory phase to match the MOLLI motion states.

Diastolic myocardial $T_1$ values measured using MOLLI (1259±46) and CMR multitasking (1247±25) are not significantly different (p=0.53, two-sided t-test) and are within the published normal range at 3 T[24]. Both methods demonstrate low coefficients of variation (CoV), indicating good repeatability (MOLLI: 1.2%, CMR multitasking: 2.5%).

Example 2: $T_1$-$T_2$ Mapping Experiments

Quantification of the spin-spin relaxation time constant T2 detects and characterizes myocardial edema, ischemia, and inflammation, and more. T2 mapping provides complementary information to T1 mapping, making joint T1-T2 mapping very promising for comprehensive myocardial tissue characterization. Currently, $T_1$-$T_2$ mapping can be performed via ECG-triggered, breath hold techniques, either mapping $T_2$ separately[25] from $T_1$ (resulting in unaligned maps), or jointly[26-30]. Joint $T_1$-$T_2$ mapping CMR multitasking requires no ECG and respiratory control, providing aligned $T_1$ and $T_2$ maps at multiple cardiac phases.

Figure 4:
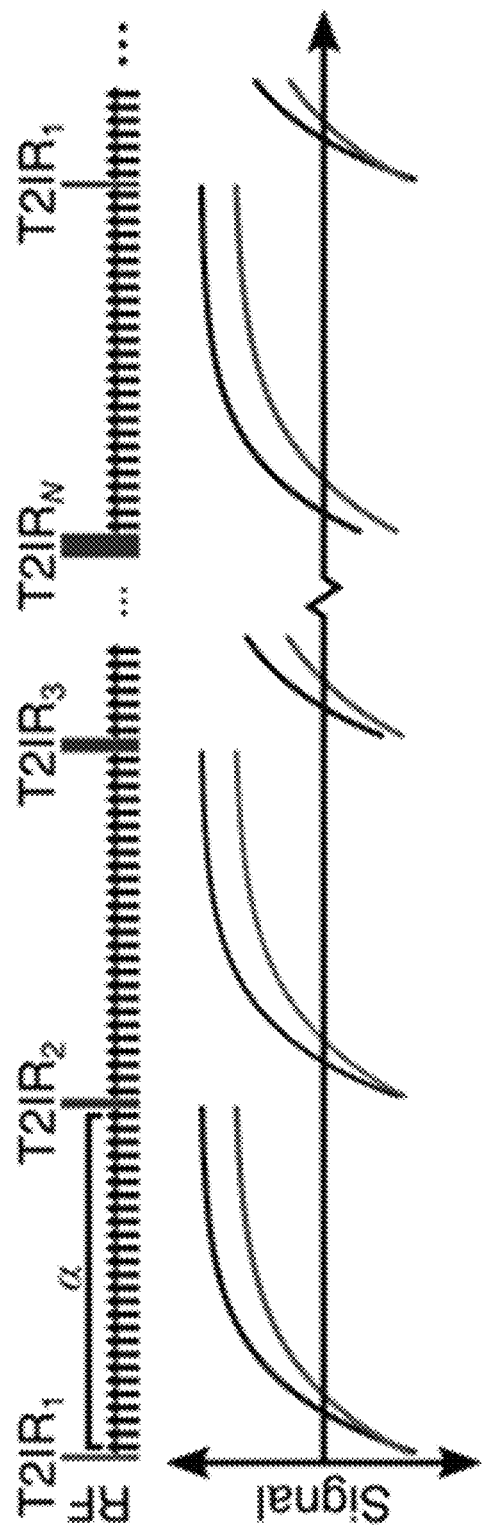
FIG. 4 shows a diagram of continuous-acquisition T2IR-FLASH acquisition.

For native myocardial $T_1$-$T_2$ mapping, $T_1$-$T_2$ contrasts were generated by cycling through a series of five hybrid T2IR preparation pulses with durations $T_{E,prep}$=12, 20, 30, 40, 50 ms. each followed by 5° FLASH readouts ($T_R$=3.6 ms, $T_E$=1.6 ms) throughout the entire 2.5 s recovery period. The T2IR pulse consists of an adiabatic $T_2$-preparation with BIR-4 refocusing, modified to apply a 90° tip-down pulse instead of a 90° tip-up pulse after refocusing (thereby achieving the effect of a 90° tip-up followed by 180° inversion). See FIG. 4. Sampling was performed according to the previously-described golden-angle sampling scheme modified to collect training data every other readout. A total of 35 T2IR pulses were applied for a total scan time of 88 s. Four time dimensions represented cardiac motion (15 cardiac phases), respiratory motion (5 respiratory phases), $T_1$ recovery (344 inversion times), and $T_2$prep duration (5 durations). As in native $T_1$ mapping, five $T_1$ relaxation basis functions were defined from the SVD of a Bloch signal dictionary, but with an expanded range of inversion pulse flip angles (i.e., the 21 B values were linearly spaced from −1 to 0) in order to address multiple signal starting points due to $T_2$ decay during T2IR preparation. $T_2$ relaxation basis functions were not pre-defined due to the complexity of simulating $B_0$ inhomogeneity. Reconstruction was performed per Eqs. (6) and (4) using $L_0$=42 and the same regularization schemes as for native $T_1$ mapping. Voxel-wise $T_1$, $T_2$, A, α, and B were fit from $$A\frac{1-e^{-T_R/T_1}}{1-e^{-T_R/T_1}\cos\alpha}[1+(Be^{-T_{E,prep}/T_2}-1)(e^{-T_R/T_1}\cos\alpha)^n]\sin\alpha. \quad (8)$$

To evaluate the accuracy and repeatability of native myocardial $T_1$-$T_2$ mapping using CMR multitasking, n=10 healthy human volunteers were recruited for imaging. Three scans each were collected of: diastolic $T_1$ maps from ECG-triggered, breath-held SSFP MOLLI 5(3)3; diastolic $T_2$ maps from ECG-triggered, breath-held $T_2$ prep-SSFP mapping; and cardiac- and respiratory-resolved $T_1$-$T_2$ maps from the proposed non-ECG, free-breathing multitasking method. One mid-ventricular short-axis slice with 1.7 mm in-plane spatial resolution and 8 mm slice thickness was imaged using each method; mean $T_1$ and $T_2$ values were compared at end-diastole and end-expiration, and the repeatability of each method was assessed by the CoV.

The feasibility of high-resolution $T_1$-$T_2$ mapping in the carotids was demonstrated according to the same basic strategy as myocardial $T_1$-$T_2$ mapping, using $T_{E,prep}$=20, 30, 40, 50, 60, 70 ms, 8° FLASH readouts ($T_R$=11.1 ms, $T_E$=6.8 ms), a 2.3 s recovery period, a 3D Cartesian Gaussian-density random sampling scheme collecting training data at the central phase encoding location every 8th readout, and a total of 216 T2IR pulses for a total scan time of 8.5 min. Images were acquired in coronal orientation at 0.7 mm isotropic spatial resolution (matrix size 208×208×36). Two time dimensions represented $T_1$ recovery (208 inversion times), and $T_2$prep duration (6 durations). Four $T_1$ relaxation basis functions were defined as previously described, and reconstruction was performed per Eq. (6) (with no regularization functional) and Eq. (4) (using a spatial TV regularization functional). A low model order $L_0$=8 was used due to reduced motion in the carotids. Voxel-wise $T_1$, $T_2$, A, α, and B were fit from Eq. (8).

Figure 5A:
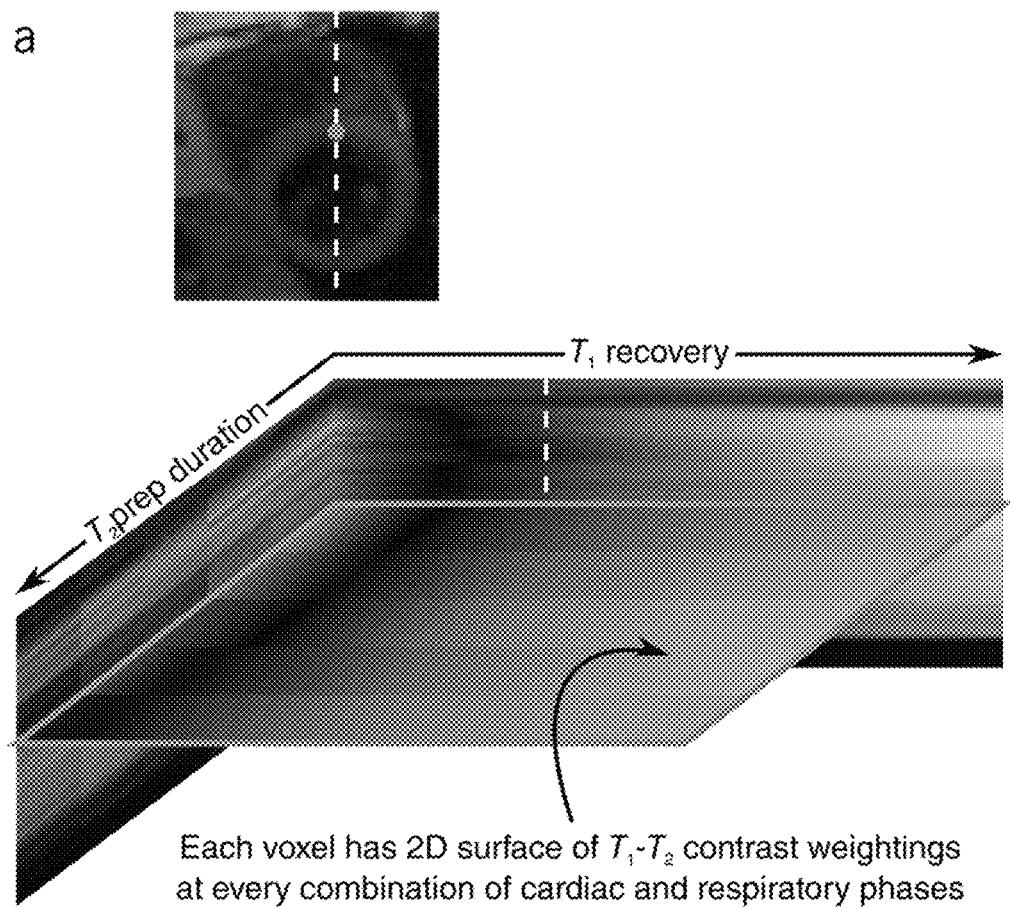
Figure 5F:
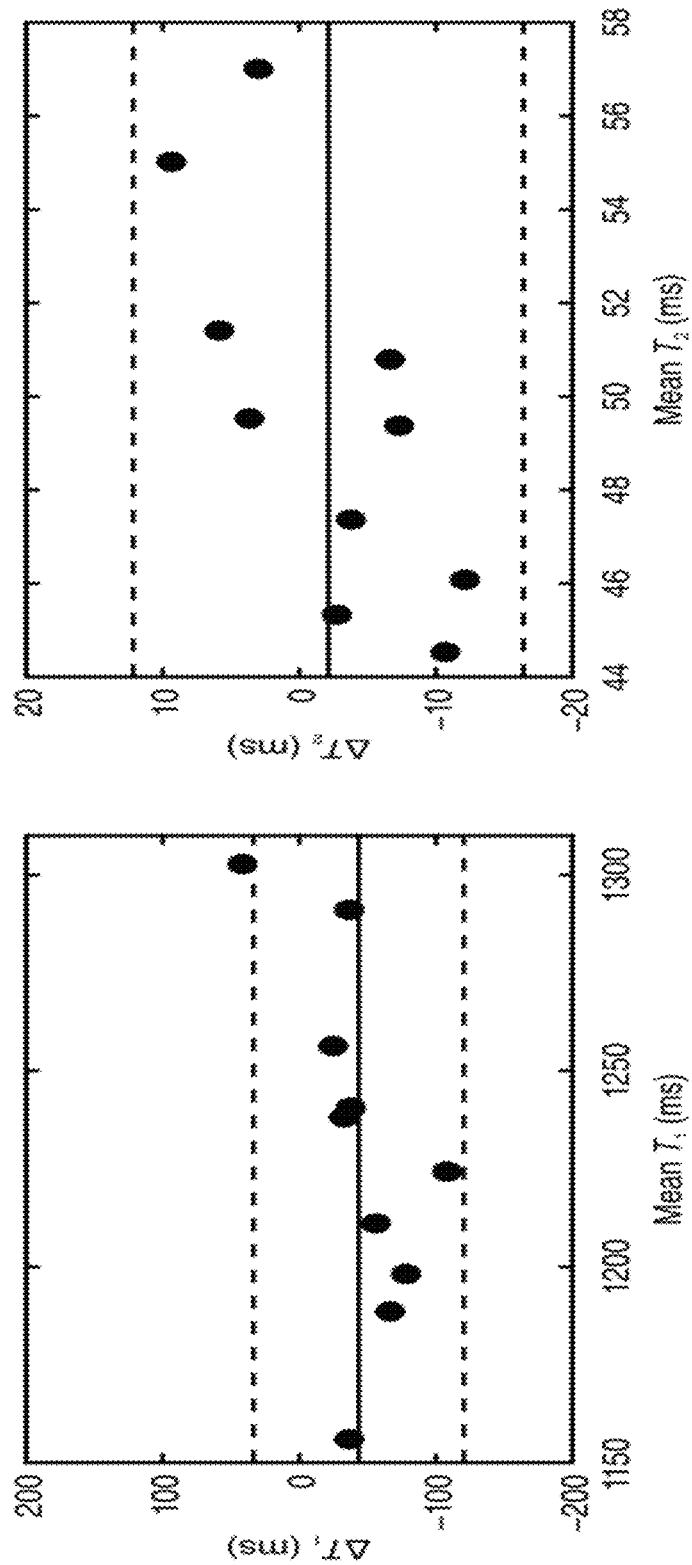

FIGS. 5a-f show CMR multitasking for non-ECG, free-breathing joint $T_1$-$T_2$ mapping in the myocardium. FIG. 5a shows CMR multitasking yields contrast variation along $T_1$ recovery and $T_2$prep duration dimensions, producing cardiac-resolved (see FIG. 5b) $T_1$ and (see FIG. 5c) $T_2$ maps. MOLLI 5(3)3 (FIG. 4d) and $T_2$prep SSFP mapping (FIG. 4e) rely on ECG-triggering and breath-holding to produce separate static parameter maps. FIG. 5f shows Bland-Altman plots comparing diastolic myocardial $T_1$ and $T_2$ values from CMR multitasking and the corresponding reference methods in healthy human subjects This section demonstrates $T_1$-$T_2$ mapping using CMR multitasking (FIG. 4a-c), measuring repeatability and accuracy in a mid-ventricular short-axis slice against $T_1$ values from MOLLI 5(3)3 (FIG. 5d) and $T_2$ values from a $T_2$-prepared steady-state free precession ($T_2$prep-SSFP) mapping method[25] (FIG. 5e). Three scans each of MOLLI, $T_2$prep-SSFP, and the proposed CMR multitasking method were performed in n=10 healthy volunteers. All three methods were performed at 1.7 mm in-plane spatial resolution. MOLLI imaged eight inversion times and $T_2$prep-SSFP imaged three $T_2$prep durations, both using ECG triggering to image at the end-diastole cardiac phase and using breath holds to image at the end-expiration respiratory phase. The non-ECG, free-breathing CMR multitasking method applied a hybrid $T_2$prep/IR (T2IR)-prepared FLASH sequence to generate multiple $T_1$-$T_2$ contrasts. Four time dimensions were imaged, measuring 344 inversion times (up to 2.5 s) for each of five $T_2$ prep durations (12 ms, 20 ms, 30 ms, 40 ms, and 50 ms) at 15 cardiac phases and five respiratory phases, for a total of 344*5*15*5=129,000 images from 88 s of data acquisition. $T_1$ and $T_2$ were jointly fit at the end-diastolic cardiac phase and end-expiration respiratory phase to match the motion states of the reference methods.

Example 3: Carotid $T_1$-$T_2$ Mapping

Figures 6A, 6B, 6C, 6D, 6E, 6F, 6G:
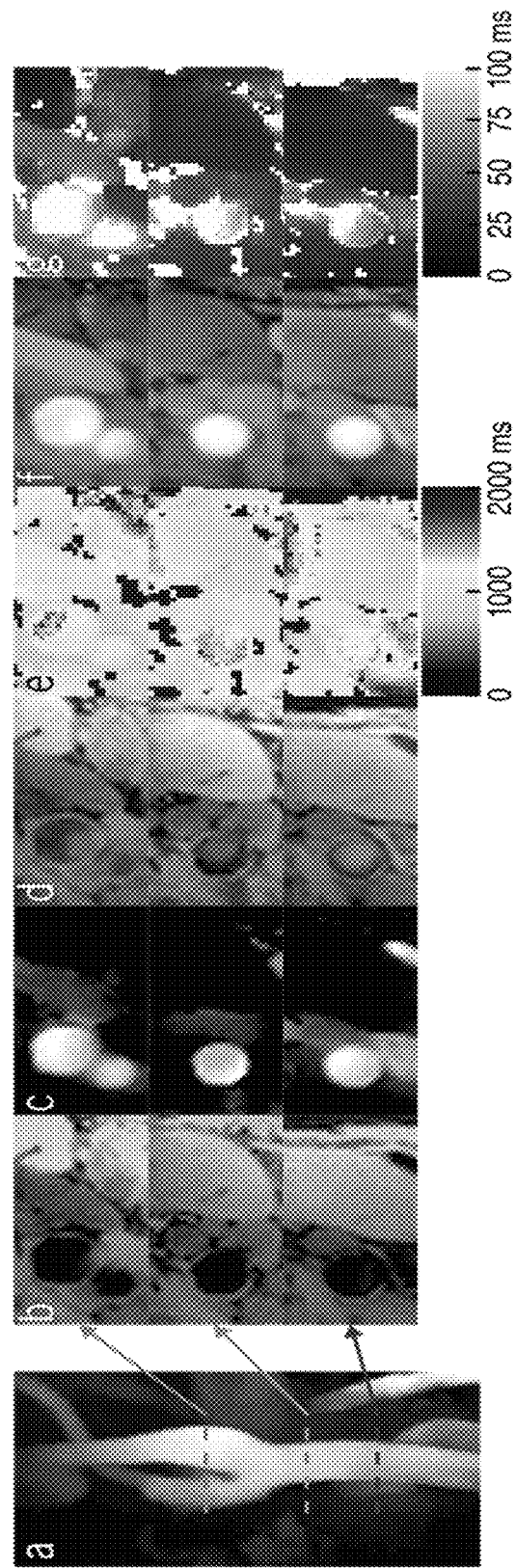
FIGS. 6a, 6b, 6c, 6d, 6e, 6f, 6g, which show CMR multitasking for multicontrast joint $T_1$-$T_2$ mapping in the carotid arteries.

Multicontrast CMR is an established technique for non-invasive evaluation of carotid atherosclerosis, with the capabilities to not only detect luminal stenosis but also characterize plaque compositions in the arterial wall. Compared with conventional qualitative multicontrast CMR, which is subject to the reader's interpretation of relative tissue intensities, $T_1$-$T_2$ mapping can potentially improve the reproducibility of the exam and allow longitudinal comparison of results. $T_1$-$T_2$ mapping has been demonstrated in the carotids, but currently requires long scan times (typically 20 minutes[31], including 5 min for $B_1$ mapping) to achieve sufficient spatial resolution for imaging the carotid arterial walls (e.g., 0.7 mm isotropic resolution). In contrast, CMR multitasking can allow comprehensive evaluation of carotid atherosclerosis at this spatial resolution in a single 8.5 min scan. The feasibility of this was demonstrated by imaging two time dimensions with T2IR-FLASH CMR multitasking. Results are shown in FIGS. 6a-g, which shows CMR multitasking for multicontrast joint $T_1$-$T_2$ mapping in the carotid arteries. FIG. 6a shows the maximum intensity projection of the bright-blood images shows the locations of the three slices depicted in b-g. A single scan yields several different image contrast weightings appropriate for evaluating different aspects of atherosclerosis: FIG. 6b shows dark-blood wall images for assessing plaque burden. FIG. 6c shows bright-blood images for assessing luminal stenosis. FIG. 6d shows $T_1$-weighted images. FIG. 6e shows a $T_1$ map, FIG. 6f shows $T_2$-weighted images. FIG. 6g shows a $T_2$ map for characterizing plaque composition.

The proposed method measured 208 inversion times (up to 2.3 s) for each of six $T_2$ prep durations for a total of 208*6=1,248 3D images from 8.5 min of data acquisition. This produces images with a range of different contrast weightings: bright-blood angiograms to assess luminal stenosis (FIG. 6a,c), dark-blood wall images to assess plaque burden (FIG. 6b), as well as multiple $T_1$-$T_2$ weightings (FIG. 6d,f) which can be used to fit for quantitative $T_1$ (FIG. 6e) and $T_2$ maps (FIG. 6g) to characterize plaque composition.

Example 4: First-Pass Myocardial Perfusion $T_1$ Mapping

First-pass myocardial perfusion imaging is a powerful tool for assessing blood flow in the myocardium, diagnosis of ischemia and coronary artery disease. The relaxation rate $R_1=1/T_1$ increases by an amount proportional to local concentration of a gadolinium (Gd)-based contrast agent, so time-resolved, $T_1$-weighted imaging can be employed to image contrast agent dynamics during the first pass of a bolus of Gd. Most first-pass perfusion imaging scans employ ECG triggering to collect one magnetization-prepared image per cardiac cycle, but recent methods have achieved imaging without ECG triggering, using steady-state pulse sequences rather than magnetization preparation to generate $T_1$ contrast[32,33]. Unfortunately, neither of these approaches allows quantification from a single scan. This is because $T_1$-weighted signal intensity has a nonlinear response to $R_1$-saturating at high Gd concentrations such as those in the blood pool at peak enhancement—violating the conventional assumptions of linearity that are used to quantify MBF. Quantitative myocardial perfusion MRI is therefore commonly performed using two scans with two boluses of contrast: the first bolus contains a small dose of contrast agent, inducing an approximately linear signal response in the blood pool at the expense of poor signal response in the myocardium, and the second bolus contains a large dose of contrast agent, inducing an approximately linear signal response in the myocardium (which is less susceptible to signal saturation) at the expense of nonlinearity in the blood pool. Quantification is then performed by assuming that there are no changes in physiology between boluses. CMR multitasking solves not only ECG issues with myocardial perfusion imaging, but its ability to perform time-resolved $T_1$ mapping allows single-bolus quantification via deconvolution of Gd concentration time curves calculated from measured $R_1$ values[34] rather than saturated $T_1$-weighted signal intensity curves, solving the nonlinearity issue.

First-pass myocardial perfusion $T_1$ mapping using CMR multitasking is demonstrated while assessing intrasession reproducibility in a mid-ventricular short-axis slice at 1.7 mm in-plane spatial resolution. Results are shown in FIGS. 7a-d.

Figure 7D:
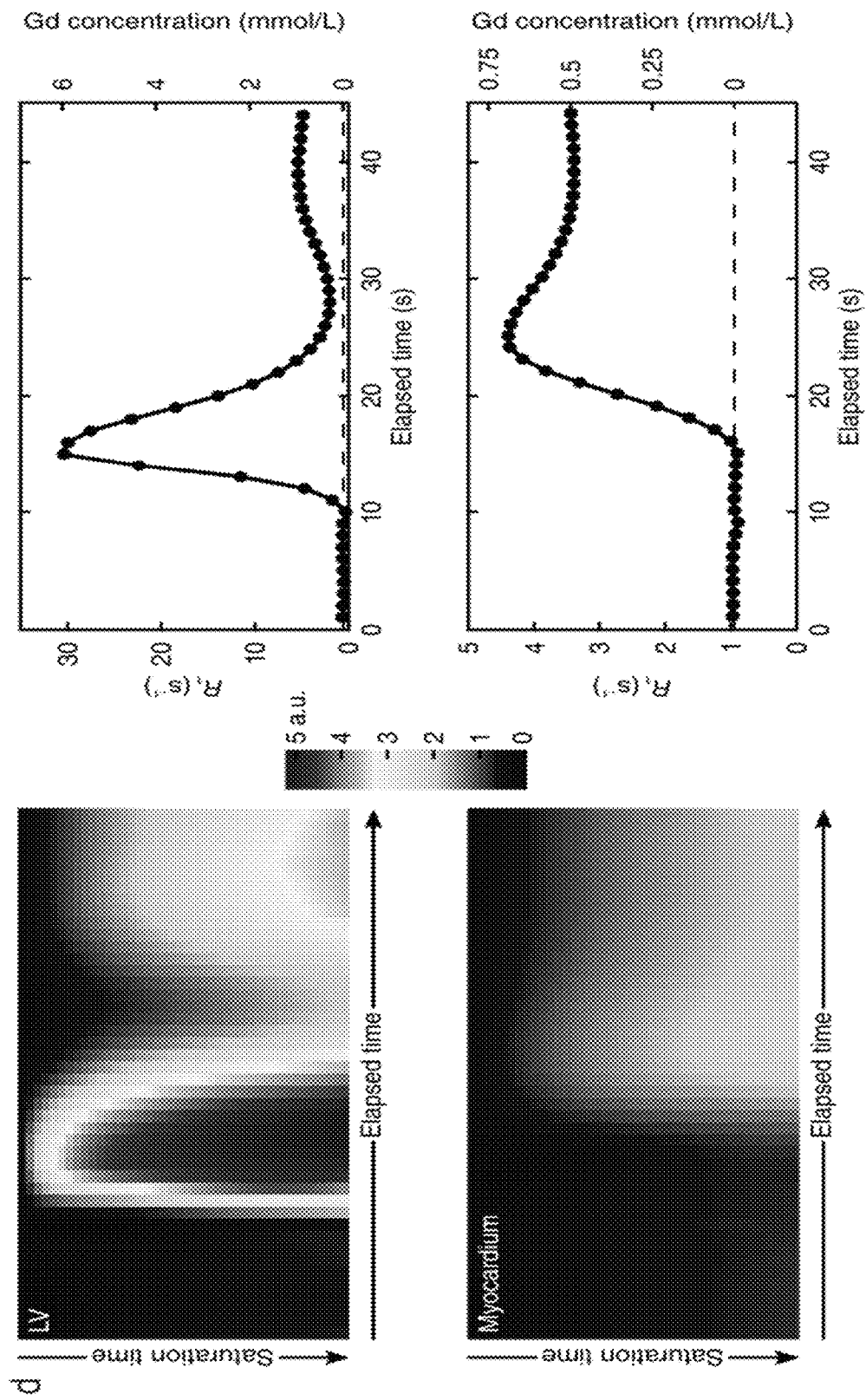

FIGS. 7a-d show CMR multitasking for non-ECG, first-pass myocardial perfusion $T_1$ mapping. FIG. 7a shows contrast agent dynamics are captured for systolic and diastolic cardiac phases, due to (see FIG. 7b) the method's ability to resolve cardiac motion. FIG. 7c shows the combination of the elapsed time dimension (for depicting contrast agent dynamics) and saturation time dimension yield 2D signal intensity surfaces rather than conventional 1D signal intensity curves. As shown in FIG. 7d, these signal intensity surfaces are used to map $R_1(t)$, which accounts for signal saturation and directly yields Gd concentration after a linear transformation.

A total of n=8 healthy volunteers were imaged. Two 0.1 mmol/kg doses of Gadavist were administered 20 to 30 minutes apart, such that the second scan started with a stable but nonzero initial concentration of Gd. CMR multitasking was implemented using a saturation recovery (SR)-prepared FLASH sequence, imaging three time dimensions: 42 saturation times (up to 300 ms) at 15 cardiac phases (FIG. 7a-b) and 47.2±4.8 cardiac cycles (as many cycles as occurred during the total elapsed time of the scan, depending on the subject's heart rate), resulting in a total of 29,767±3,026 images from 45 s of data acquisition. MBF was assessed at end-diastole via Fermi deconvolution of $R_1$-derived contrast agent concentration time curves (FIG. 7c-d).

A two-way ANOVA (see Table 1) indicated a nonsignificant difference (p=0.44) between repetitions and a nonsignificant difference (p=0.47) between the six American Heart Association (AHA)-defined mid-ventricular segments (as expected for healthy subjects). MBF values from both boluses (First bolus: 1.18±0.35; Second bolus: 1.23±0.32) were within the normal range reported in previous literature[35]. The within-segment standard deviation was 0.30 g/mL/min.

TABLE 1

Two-way ANOVA table indicating nonsignificant differences between repetitions and segments, as expected for healthy subjects.

| Source | Sum of Squares | Degrees of Freedom | Mean Squares | F | p |
| --- | --- | --- | --- | --- | --- |
| Segments | 0.527 | 5 | 0.105 | 0.92 | 0.47 |
| Repetition | 0.065 | 1 | 0.065 | 0.57 | 0.44 |
| Error | 10.229 | 89 | 0.115 | | |
| Total | 10.821 | 95 | | | |

Example 5: DCE T1 Mapping Experiments

Figure 8:
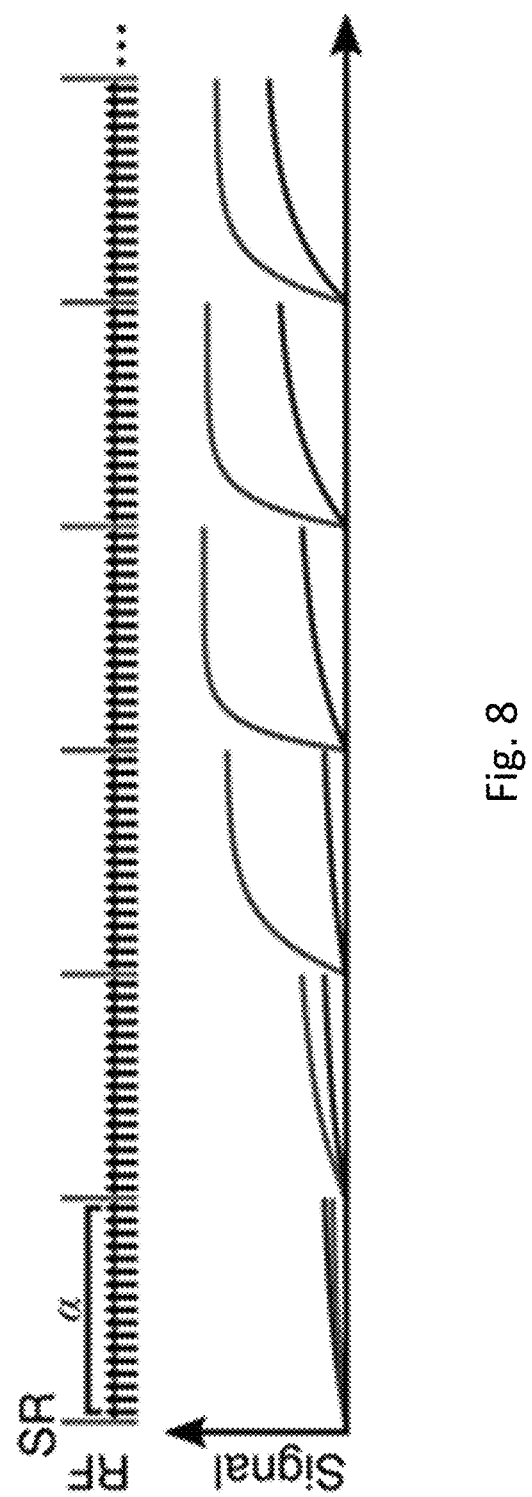
FIG. 8 shows a diagram of continuous-acquisition SR-FLASH acquisition. Illustrative signal curves are shown for two tissues with different starting $T_1$ values and contrast agent uptakes.

For first-pass myocardial perfusion $T_1$ mapping, $T_1$ contrasts were generated using SR magnetization preparation followed by 10° FLASH readouts ($T_R$=3.6 ms, $T_E$=1.6 ms) throughout a 300 ms recovery period (see FIG. 8). The short recovery period and SR preparation scheme were chosen to reduce blood inflow effects, as accurate blood signal quantification is vital to accurate quantification of MBF. Golden-angle sampling with training data collected every other readout was performed. A total of 150 SR periods were acquired for a total scan time of 45 s. Four time dimensions represented cardiac motion (15 cardiac phases), respiratory motion (5 respiratory phases), $T_1$ recovery (42 saturation times), and elapsed time depicting contrast agent dynamics (one bin per cardiac cycle). Five $T_1$ relaxation basis functions were defined according to the same process as for native $T_1$ mapping, but with 30 a values in half-degree increments from 0.5° to 15° and 21 B values linearly spaced from −0.25 to 0.25. Reconstruction was performed per Eq. (6) using temporal TV regularization along the cardiac, respiratory, and elapsed time (DCE) dimensions and Eq. (4) using $L_0$=36 and spatial TV regularization.

The intrasession reproducibility of MBF quantification using myocardial perfusion $T_1$ mapping was assessed in n=8 healthy human volunteers by administering two 0.1 mmol/kg doses of Gadavist (4 mL/s injection rate, followed by 20 mL saline flush) 20 to 30 minutes apart (i.e., long enough for the first bolus to reach a steady-state). Subjects were instructed to hold their breath for as much of the scan as possible, followed by shallow breathing. One mid-ventricular short-axis slice with 1.7 mm in-plane spatial resolution and 8 mm slice thickness was imaged each time. To quantify MBF, $T_1(t)$, A, α, and B were fit according to $$A \frac{1 - e^{-T_R/T_1(t)}}{1 - e^{-T_R/T_1(t)} \cos\alpha} [1 + (B-1)(e^{-T_R/T_1(t)} \cos\alpha)^n] \sin\alpha, \quad (9)$$

from the left ventricular (LV) blood pool and six myocardial segments at end-diastole. Contrast agent concentration Gd(t) was calculated as $$Gd(t) = \Delta R_1(t)/\gamma = \left(\frac{1}{T_1(t)} - \frac{1}{T_{1,pre}}\right)/\gamma, \quad (10)$$

where γ is the $T_1$ relaxivity of the contrast agent (5 mM$^{-1}$·s$^{-1}$) and $T_{1,pre}$ is the baseline $T_1$ (i.e., the mean pre-contrast $T_1$). Fermi deconvolution of each myocardial Gd(t) by the left ventricular blood pool Gd (t) yielded the MBF for each myocardial segment. A two-way ANOVA was performed to assess differences in MBF between segments and repetitions; repeatability of each method was quantified by the CoV.

The feasibility of $T_1$ mapping during DCE in the carotids was demonstrated according to the same basic strategy as first-pass myocardial perfusion $T_1$ mapping, using 8° FLASH readouts ($T_R$=11.1 ms, $T_E$=6.8 ms), a 600 ms recovery period, a 3D Cartesian Gaussian-density random sampling scheme collecting training data at the central phase encoding location every 8$^{th}$ readout, and a total of 1300 SR periods for a scan time of 13 min. Images were acquired in coronal orientation at 0.7 mm isotropic spatial resolution (matrix size 208×208×36). Imaging was performed during injection of a 0.1 mmol/kg dose of Gadavist followed by 20 mL saline flush, injected at 1.0 mL/s. Two time dimensions represented $T_1$ recovery (52 saturation times), and elapsed time (depicting DCE in 250 bins, each with a 2.4 s temporal footprint). Four $T_1$ relaxation basis functions were defined as in myocardial perfusion $T_1$ mapping, and reconstruction was performed per Eq. (6) (penalizing temporal TV along the elapsed time dimension) and Eq. (4) (using a spatial TV regularization functional). A low model order $L_0$=6 was used due to reduced motion in the carotids. Voxel-wise $T_1(t)$, amplitude, FLASH flip angle, and the saturation pulse flip angle were fit according to Eq. (9).

Figure 9A:
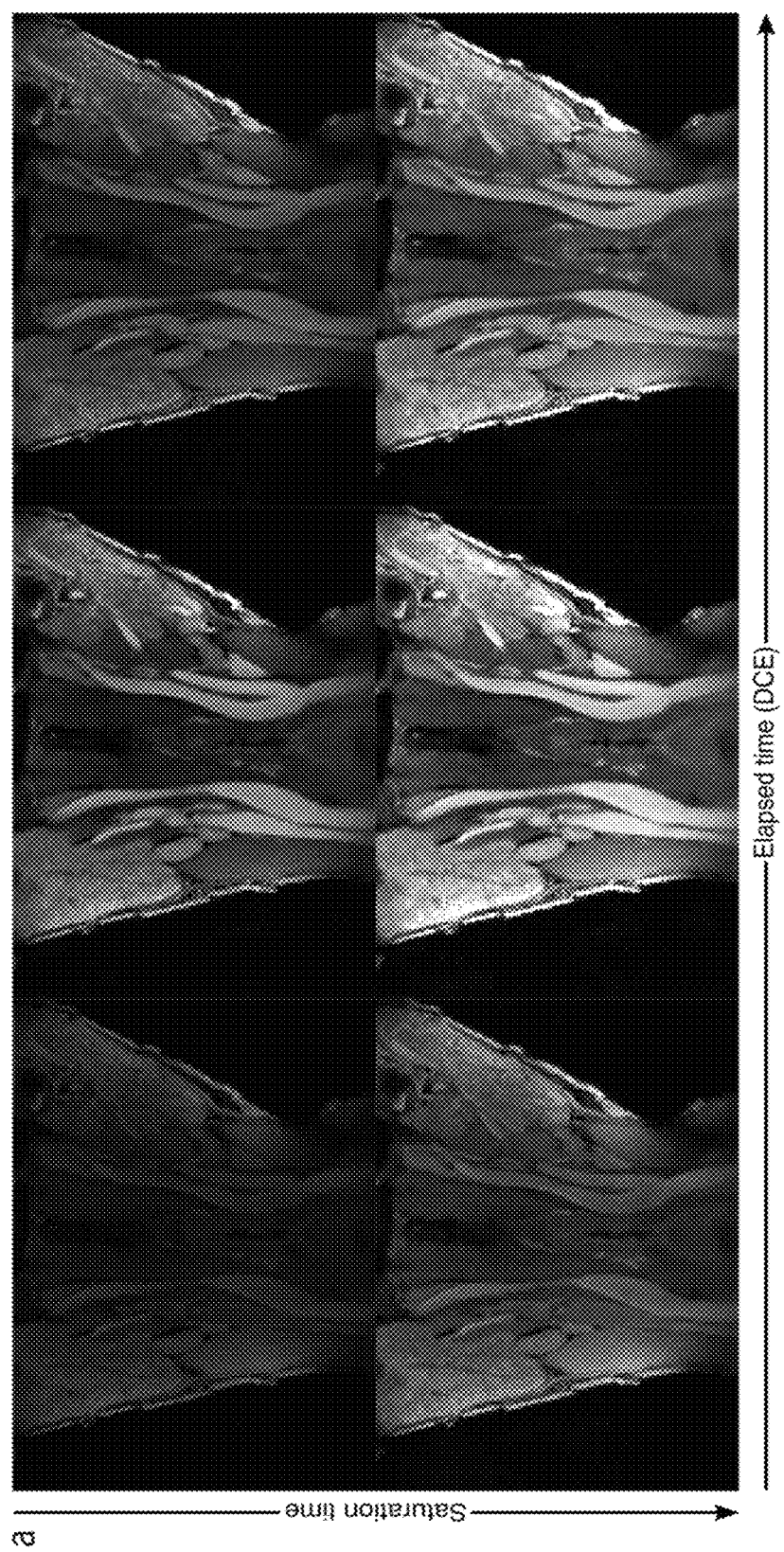
FIGS. 9a, 9b, and 9c show the results of CMR multitasking for DCE $T_1$ mapping in the carotid arteries.
Figure 9B:
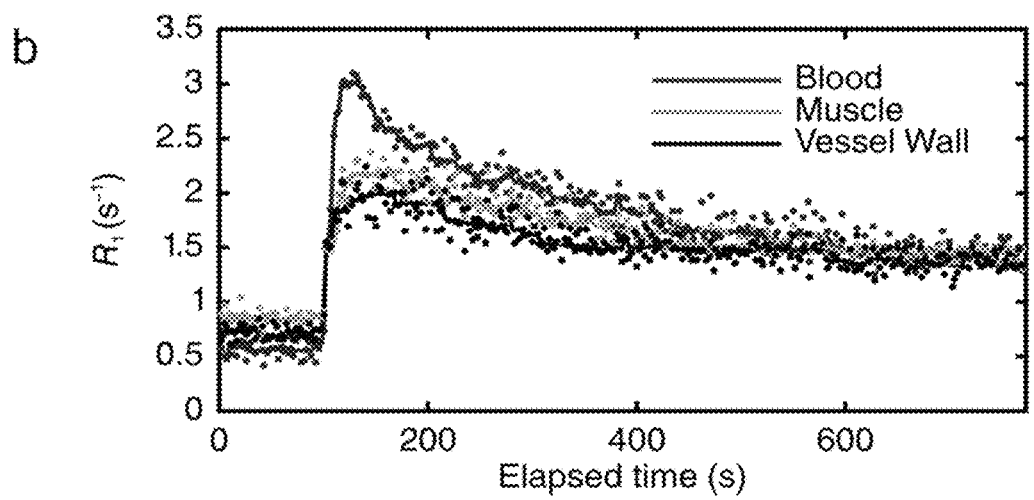
Figure 9C:
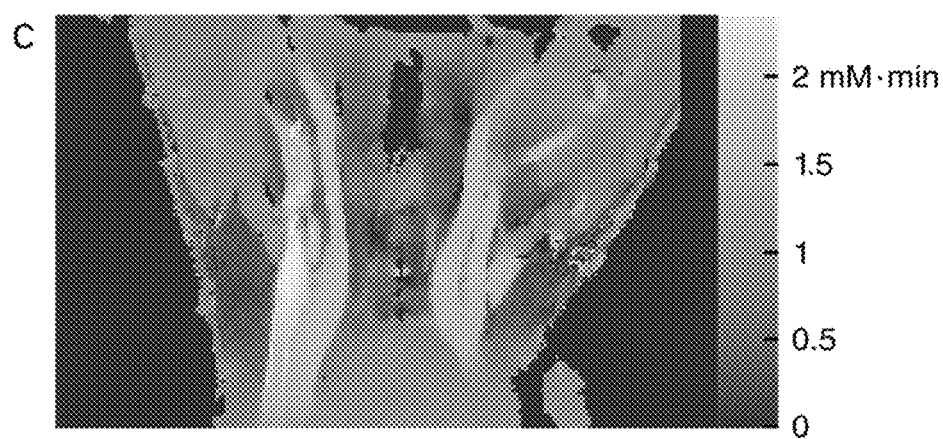

FIGS. 9a-c show the results of CMR multitasking for DCE $T_1$ mapping in the carotid arteries. FIG. 9a shows issue signal dynamics are captured at multiple saturation times throughout the dynamic contrast enhancement process, yielding (see FIG. 9b) voxel-wise $R_1(t)$ curves. The solid lines shown in b are median filtered with a width of 20 s for display purposes, but the unfiltered values (denoted by dots) were used for (see FIG. 9c) voxel-wise AUC analysis.

Example 6: Time-Resolved T1 Mapping

High-dimensional imaging has great potential to improve many cardiac applications, but is difficult to perform due to prohibitive data acquisition requirements. For example, first-pass myocardial perfusion quantification may be improved by $T_1$ mapping (requiring a relaxometry/recovery dimension) and may additionally benefit from analysis at multiple cardiac phases. As discussed above, the present disclosure contemplates a general framework for high-dimensional cardiac imaging, employing low-rank tensor modeling and extending motion-sorted joint reconstruction to additional dimensions. A variant of the framework, was examined, using explicit subspaces (estimated from navigator data and a dictionary of solutions to the Bloch equations, similar to MR fingerprinting) to perform free-breathing, ECG-less $T_1$ mapping of native myocardium at multiple cardiac phases, as well as ECG-less, cardiac- and time-resolved $T_1$ mapping during first-pass perfusion.

All data were acquired on a 3 T Siemens Verio scanner using a modified golden-angle radial sequence with parameters in FIG. 10. The 0° radial line was acquired every other a-pulse for $y_{nav}$. Only 1 minute of data were used for each reconstruction. The full recovery curve was sampled by continually applying alpha pulses in between preparation pulses. The full set of inversion times experienced by the golden angle readouts (345 for IR-FLASH, 71 for SR-FLASH) was reconstructed in order to avoid grouping lines from different recovery times, as frequent collection of center k-space in radial trajectories temporally blurs image contrast. $T_1$, amplitude, a, and preparation pulse efficiency were calculated pixel-by-pixel from the reconstructed images.

Figure 11:
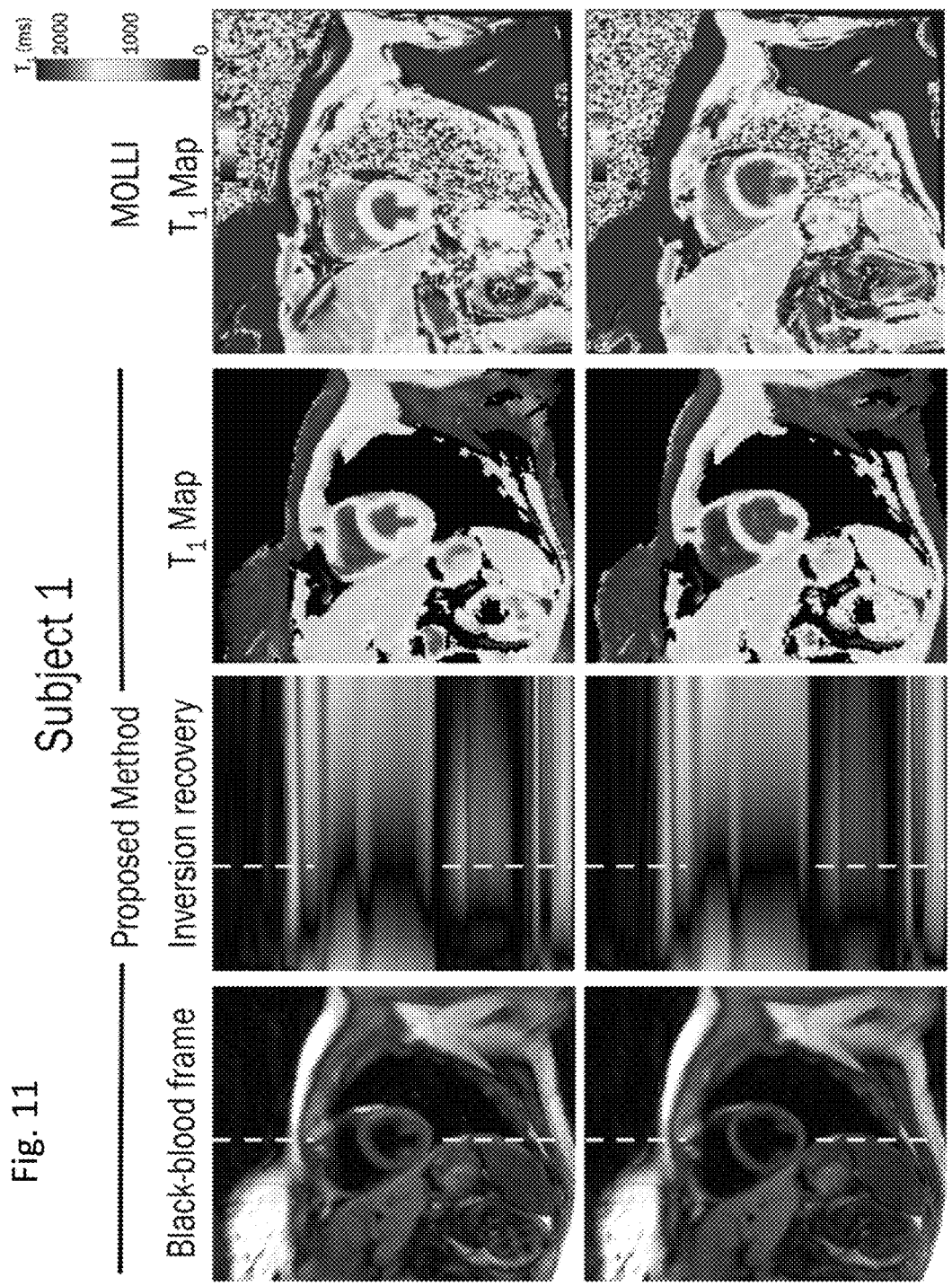
FIG. 11 shows free-breathing native T mapping results for Subject 1.
Figure 12:
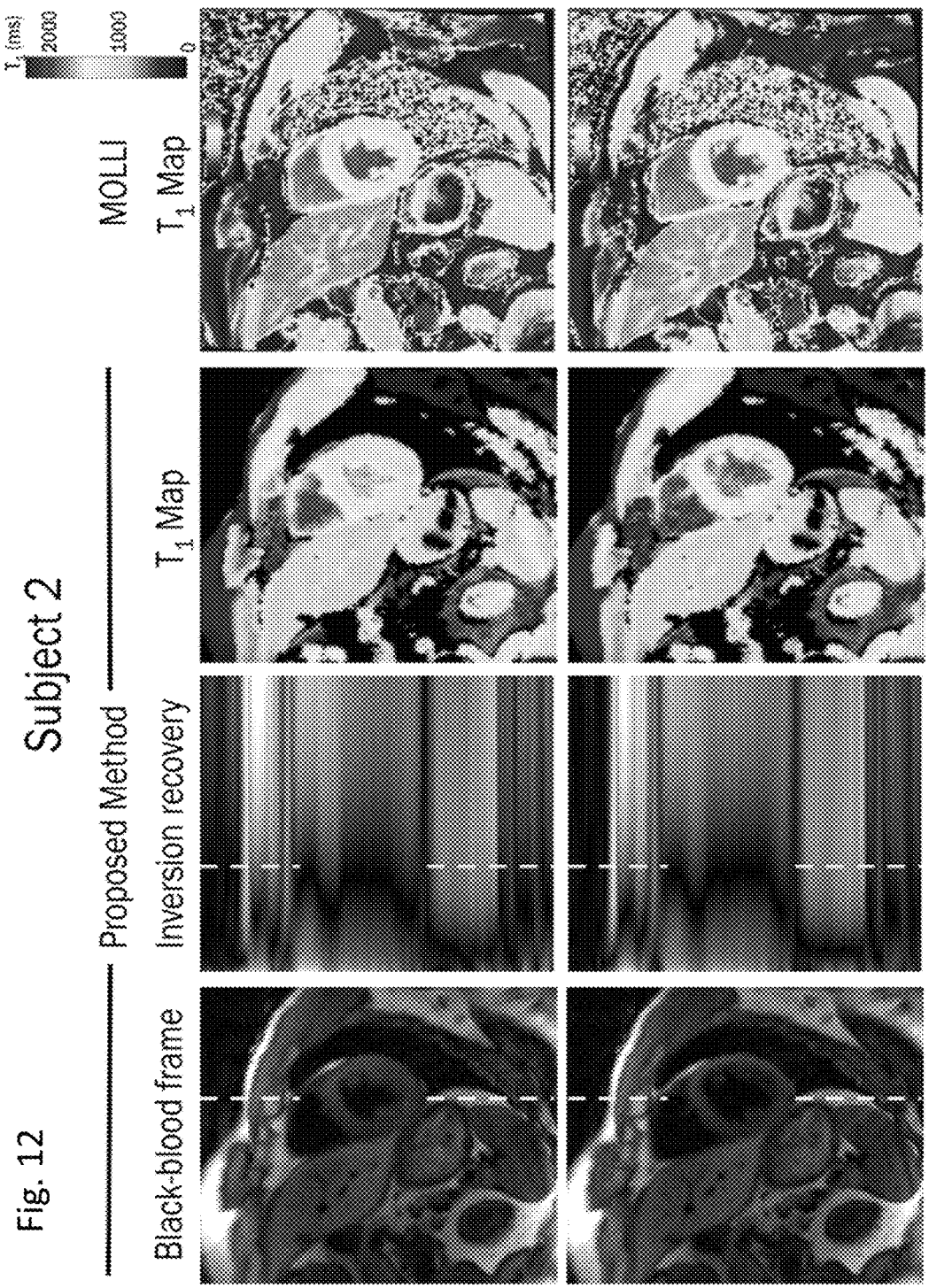
FIG. 12 shows free-breathing native T mapping results for Subject 2.
Figure 22:
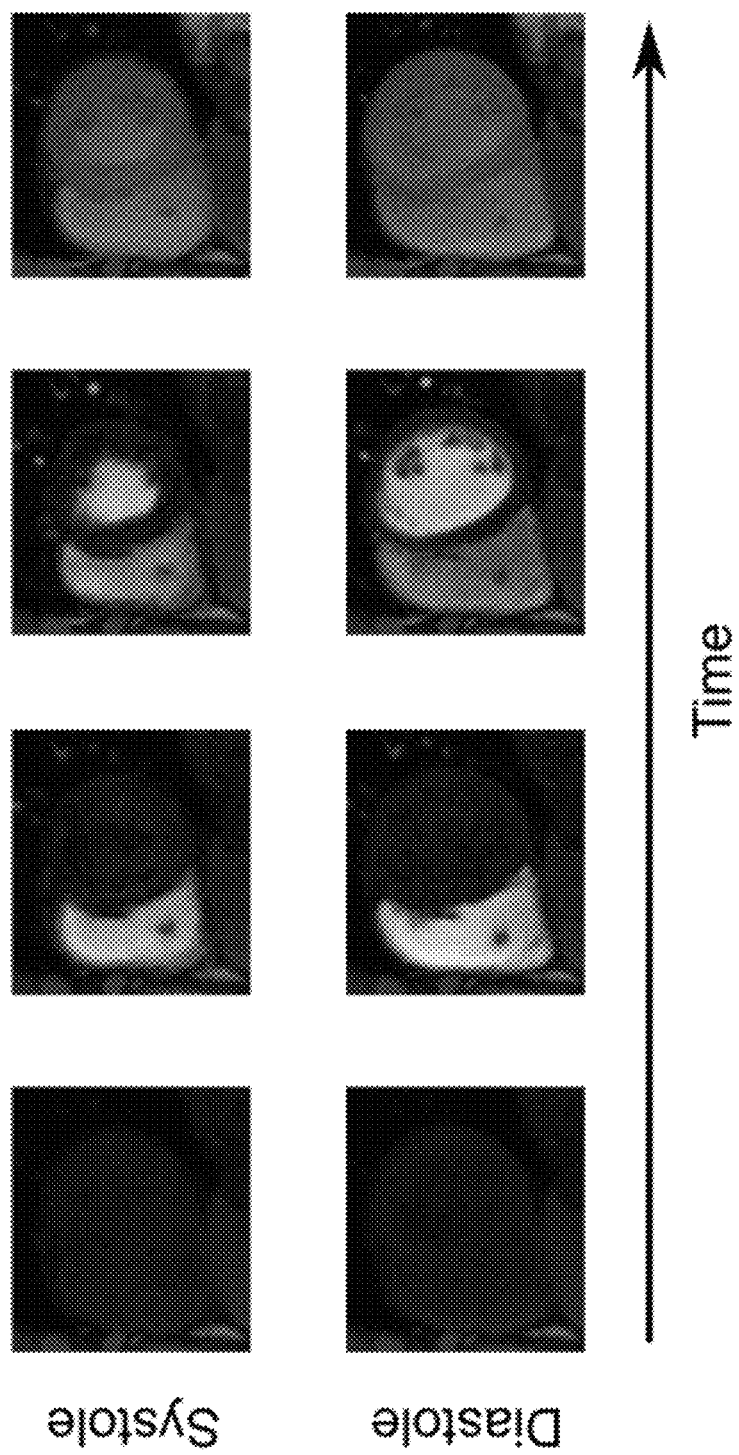
FIG. 22 shows example images showing contrast agent dynamics for both systole and diastole.

Results. FIG. 22 depicts end-systole and end-diastole images and inversion recovery profiles for Subject 1, as well as native $T_1$ maps and MOLLI reference $T_1$ maps. In particular, FIG. 11 shows free-breathing native T mapping results for Subject 1. From left to right in FIG. 6: 1) black-blood images (at the null inversion time of blood), and 2) spatiotemporal slices depicting inversion recovery evolution over a line through the ventricles. These images are available for both end-systole and end-diastole, demonstrating different ways to slice the reconstructed tensor. 3) T maps for both endsystole and end-diastole. 4) Reference T maps using MOLLI, showing reasonable agreement. FIG. 12 shows the results for Subject 2.

Figure 13:
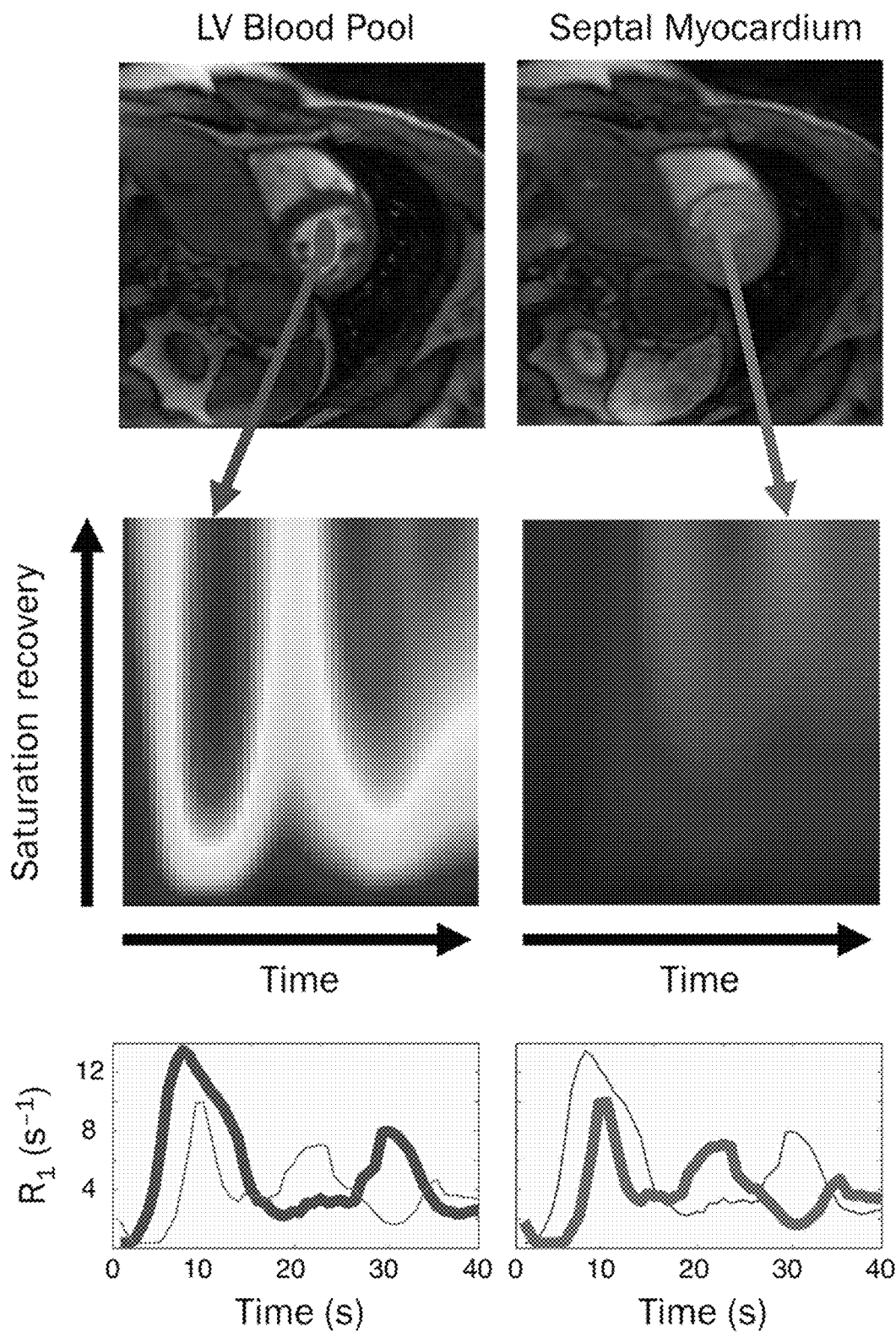
FIG. 13 shows time-resolved $T_1$ mapping during the first pass of contrast agent.

FIG. 13 shows first-pass perfusion images, saturation recovery curves as a function of wall-clock time, and $R_1$ quantitative curves for the LV blood pool (at end-diastole for maximum LV volume) and septal myocardial segments (at end-systole for maximum myocardial thickness). In particular, FIG. 13 shows time-resolved $T_1$ mapping during the first pass of contrast agent. The top row shows reconstructed images with the locations of the regions of interest. The middle row depicts the change in saturation recovery behavior (vertical) from heartbeat to heartbeat (horizontal). Finally, the bottom row shows the calculated R as a function of time for blood (highlighted in left) and myocardium (highlighted in right), allowing quantification of contrast agent concentration.

As shown in the previous figures, native $T_1$ measurements with the proposed framework show good agreement with MOLLI—the absolute difference in mean myocardial $T_1$s ranged from 25 ms (Subject 2 diastole) to 80 ms (Subject 1 diastole; all other differences were <40 ms)—and did so without breathhold- or ECG-reliance. There is no standard method to compare first-pass $T_1$ maps against, but the measured blood pool and myocardial signal curves obeyed typical patterns regarding contrast agent dynamics.

Discussion and Conclusion. The framework exploiting the low-rank tensor structure of high-dimensional cardiac images has been examined, demonstrating its use for two challenging applications. The framework enhances the practical utility of native $T_1$ mapping—using efficient, continual acquisition and advanced reconstruction techniques to overcome the practical limitations of ECG and breathholds; and 2) demonstrating time-resolved $T_1$ mapping during first-pass perfusion, which may allow direct quantification of tissue contrast agent concentration.

Example 7: Ungated, Free-Breathing Native $T_1$ Mapping in Multiple Cardiac Phases in Under One Minute As discussed above, current cardiac $T_1$ mapping techniques in use clinically are generally limited to single-shot 2D images acquired in a breath hold with ECG gating which implies the need for a regular heart rhythm and reliable breath-holding; both of which are potential causes for reduced accuracy and reproducibility of the $T_1$ maps in clinical practice. Heart rate variability or poor ECG triggering has been identified as a major source of error and cause for reduced reproducibility of myocardial $T_1$ maps in the widely used MOLLI $T_1$ mapping technique. The resolution of other inversion recovery and saturation recovery 2D single-shot techniques is limited by the acquisition window, especially for subjects with relatively high heart rates; higher resolution requires segmentation with multiple breath holds and potential image mis-registration. To mitigate the dependence of $T_1$ mapping on heart rate and breath-holds, an ungated, free-breathing, continuous inversion recovery approach using low-rank tensors modeling the image as partially separable in space, cardiac phase, respiratory phase, and inversion time in order to reduce sampling requirements was examined.

Methods. All imaging was performed on a 3T Siemens Verio scanner. The proposed sequence uses an ungated, freebreathing, 2D continuous modified golden angle radial acquisition scheme (odd readouts were incremented by the golden angle, even readouts were a 0° navigator readout used for cardiac/respiratory binning and subspace estimation) with 180° inversion pulses every 2.5 seconds, 5° flip angle, echo spacing 3.6 ms, resolution 1.7×1.7×8 mm³ in a mid-ventricular slice with acquisition time: 58 seconds. The data was reconstructed using an explicit tensor subspace constraint estimated from the navigator data and from a dictionary of signal curves generated from the Bloch equations to obtain 345 inversion time (TI) images for 15 cardiac phases and 5 respiratory phases. Pixel-wise $T_1$ maps were computed by nonlinear least-squares regression of the resulting TI images from cardiac bins for systole and diastole from a respiratory bin representing end-expiration. Additionally, a MOLLI 5(3)3 $T_1$ map was acquired with the same resolution in diastole and systole in an end-expiration breath hold in a single mid-ventricular slice. $T_1$ was measured by drawing a region-of-interest (ROI) in the septal region on the $T_1$ maps. For the MOLLI 5(3)3 the blood pool $T_1$ was measured from the $T_1$* map which experiences no Look-Locker correction.

Figure 14:
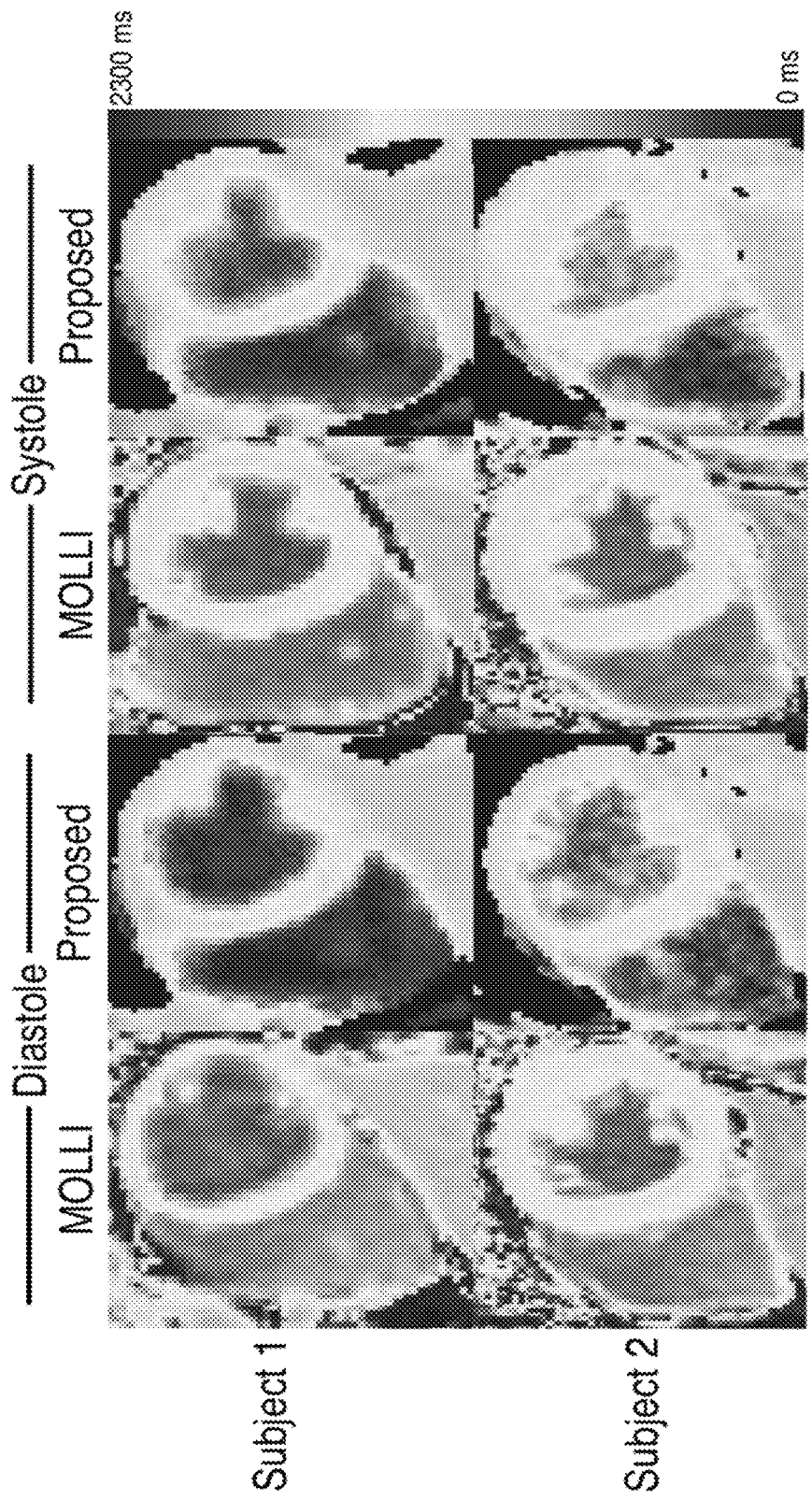
FIG. 14 shows $T_1$ maps from an ungated, free-breathing method according to an embodiment and MOLLI 5(3)3 from two healthy subjects.

Results and Discussion. The scan time for the proposed ungated, free-breathing method was exactly 58 seconds while the MOLLI method required two separate breath hold scans for systole and diastole with a wait time between breath holds. $T_1$ maps from the proposed ungated, free-breathing method and MOLLI 5(3)3 from two healthy subjects (1 female, age 26; 1 male, age 53) are shown in FIG. 14. The $T_1$ values for the septal myocardium from the proposed method and MOLLI 5(3)3 for both subjects are shown in the table in FIG. 15. Diastolic native $T_1$ values are higher than systolic values consistent with published data. Sequence differences (FLASH vs SSFP) may potentially explain differences in myocardial $T_1$ values. Blood pool $T_1$ values for the proposed method are higher due to blood in inflow effects with a slice selective readout.

Conclusion. Continuous IR $T_1$ mapping technique is shown, from which T1 maps can be obtained in different cardiac and respiratory phases without ECG gating or breath holds. The proposed method shows promise as a fast T1 mapping technique with no dependence on heart rate or breath holds.

Example 8: Low-Rank Tensor Imaging for Non-ECG Multidimensional Cardiovascular MRI As discussed above, cardiovascular MRI suffers from the curse of dimensionality in its many applications, from angiography to myocardial perfusion to T1 mapping. This results in dependence on inefficient "freezing" mechanisms to isolate different sources of image dynamics: ECG gating to freeze cardiac motion, breath-holding to freeze respiratory motion, steady-state imaging or limited acquisition windows to freeze image contrast, etc. Here we present a new framework for cardiovascular MRI—low-rank tensor imaging—that expands spatiotemporal low-rank imaging to handle multiple time dimensions (i.e., multiple sources of image dynamics), yielding high-quality images from very sparsely sampled data. The method has many different capabilities, e.g. non-ECG, free-breathing, multi-contrast imaging. This framework was demonstrated on non-ECG $T_1$-mapped quantitative myocardial perfusion and non-ECG, free-breathing myocardial $T_1$ mapping.

Figure 16:
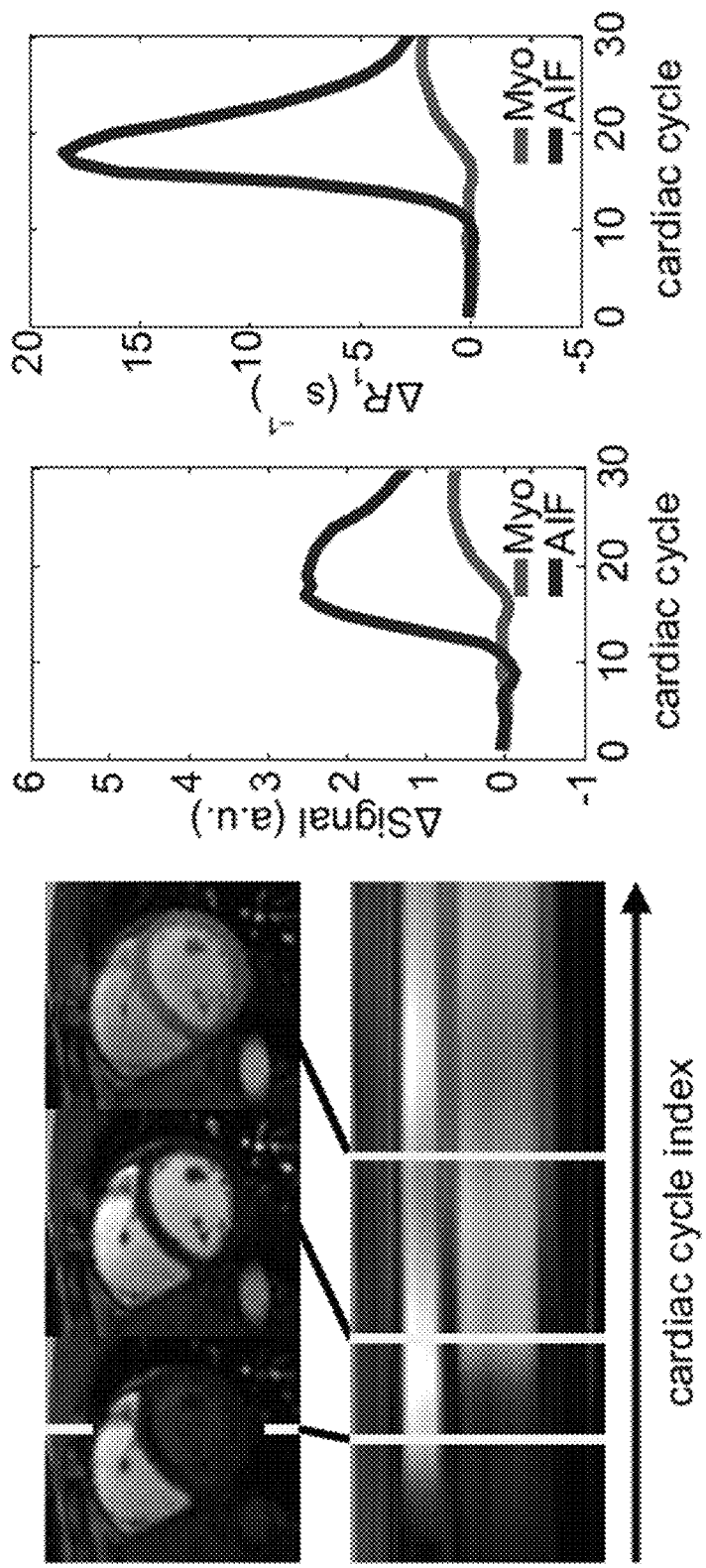
FIG. 16 shows first-pass perfusion images as well as baseline-corrected signal intensity curves and R1 curves for the LV blood pool and septal myocardial segment at end-diastole for the IR-FLASH method performed according to an embodiment.
Figure 17:
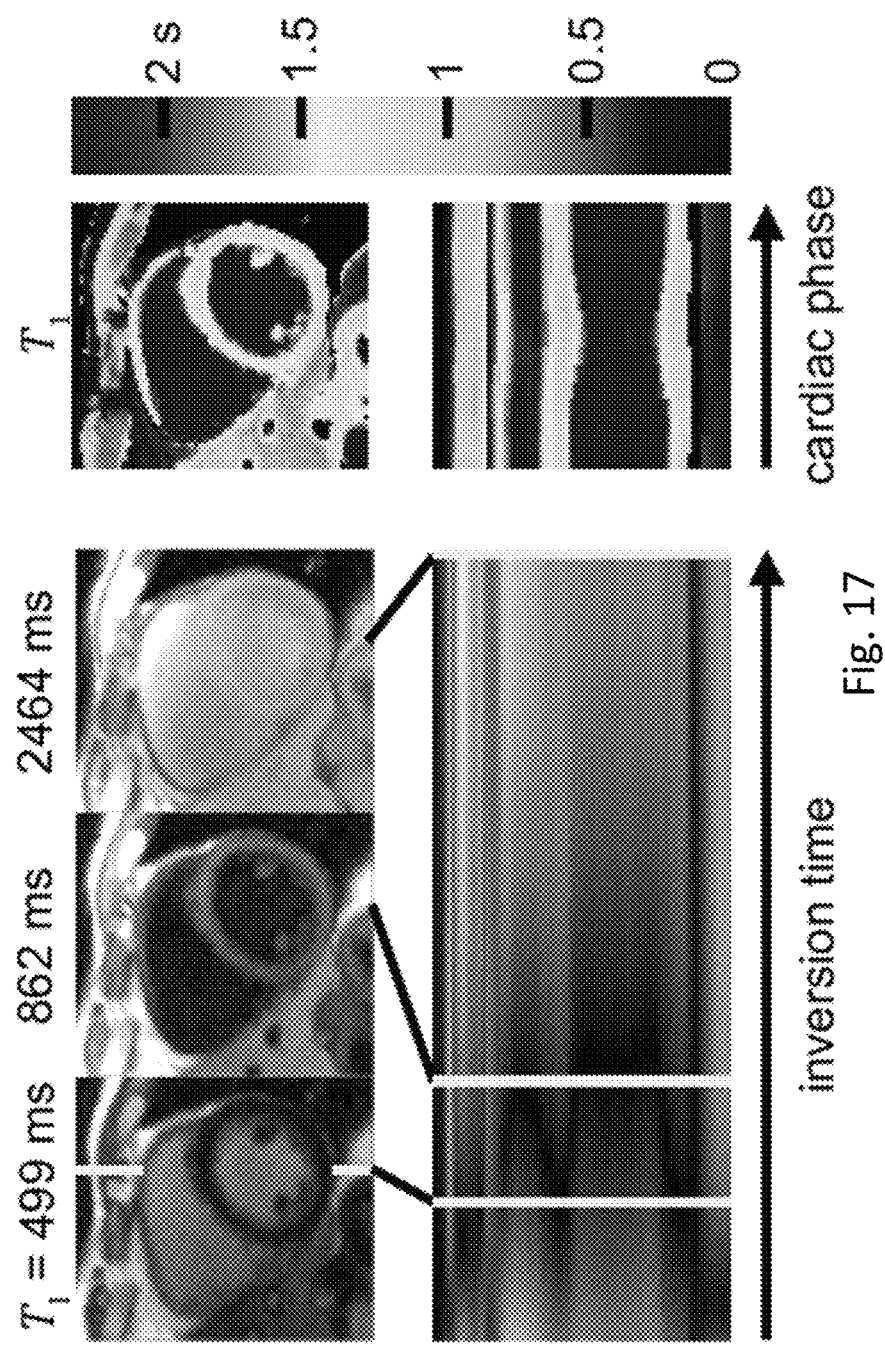
FIG. 17 depicts three of the 345 IR-FLASH contrasts, a $T_1$ relaxation profile, and a $T_1$ map (all displayed for end-diastole), as well as a $T_1$ profile over the full cardiac cycle, for the IR-FLASH method performed according to an embodiment.
Figure 18:
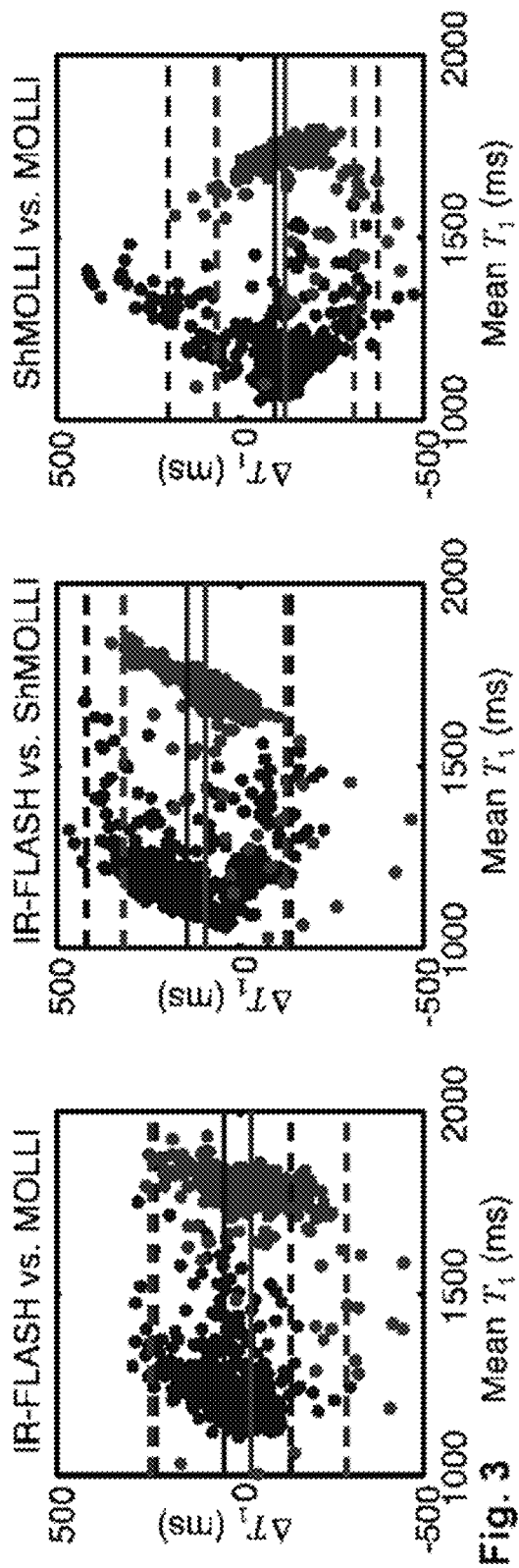
FIG. 18 depicts voxelwise Bland-Altman plots of myocardial $T_1$ and LV blood pool $T_1$* (less sensitive to inflow), comparing the IR-FLASH-based method, MOLLI, and ShMOLLI.

Results: FIG. 16 shows first-pass perfusion images as well as baseline-corrected signal intensity curves and R1 curves for the LV blood pool and septal myocardial segment at end-diastole. Signal intensity at a saturation time of 280 ms under-estimates the arterial input function (AIF) due to a nonlinear response to contrast agent concentration; however, the R1 curve has a linear response. For the myocardial $T_1$ mapping application, FIG. 17 depicts three of the 345 IR-FLASH contrasts, a $T_1$ relaxation profile, and a $T_1$ map (all displayed for end-diastole), as well as a $T_1$ profile over the full cardiac cycle. This demonstrates the ability to retroactively choose the inversion time and to map $T_1$ at any cardiac phase. FIG. 18 depicts voxelwise Bland-Altman plots of myocardial $T_1$ and LV blood pool $T_1$* (less sensitive to inflow), comparing the proposed IR-FLASH-based method, MOLLI, and ShMOLLI. Of the three pairings, the proposed method vs. MOLLI shows the smallest mean difference and closest myocardial limits of agreement; ShMOLLI vs. MOLLI shows the closest blood pool limits of agreement. Only the proposed method was performed without using breath holding or ECG.

Conclusion: A framework for exploiting the low-rank tensor structure of multidimensional cardiac images was examined. The framework enhances the practical utility of $T_1$ map-ping—using efficient, continual acquisition and advanced reconstruction techniques to overcome the practical limitations of ECG and breath-holds—and demonstrates time-resolved mapping during first-pass perfusion, which may allow direct quantification of tissue contrast agent concentration with a single bolus.

Example 9: Non-ECG, Free-Breathing Joint Myocardial T1-T2 Mapping Using CMR Multitasking As discussed above, T1 and T2 maps are typically acquired using ECG-triggering and breath-holding, which lead to heart-rate sensitivity and patient discomfort (or when unsuccessful, mis-triggering and/or respiratory motion artifacts). Here, a methodology is examined for achieving non-ECG, free-breathing joint T1-T2 mapping using the cardiovascular low-rank tensor (LRT) imaging framework for CMR multitasking (simultaneous imaging of multiple dynamics such as cardiac/respiratory motion, T1 recovery, T2 decay, etc.).

Methods. The proposed method employed hybrid T2prep/IR magnetization preparation and a continuous-acquisition single-slice 2D radial sequence with a golden-angle ordering scheme modified to collect LRT subspace training data. T1-T2 contrast was achieved using a T2prep/IR preparation pulse.

Figure 19:
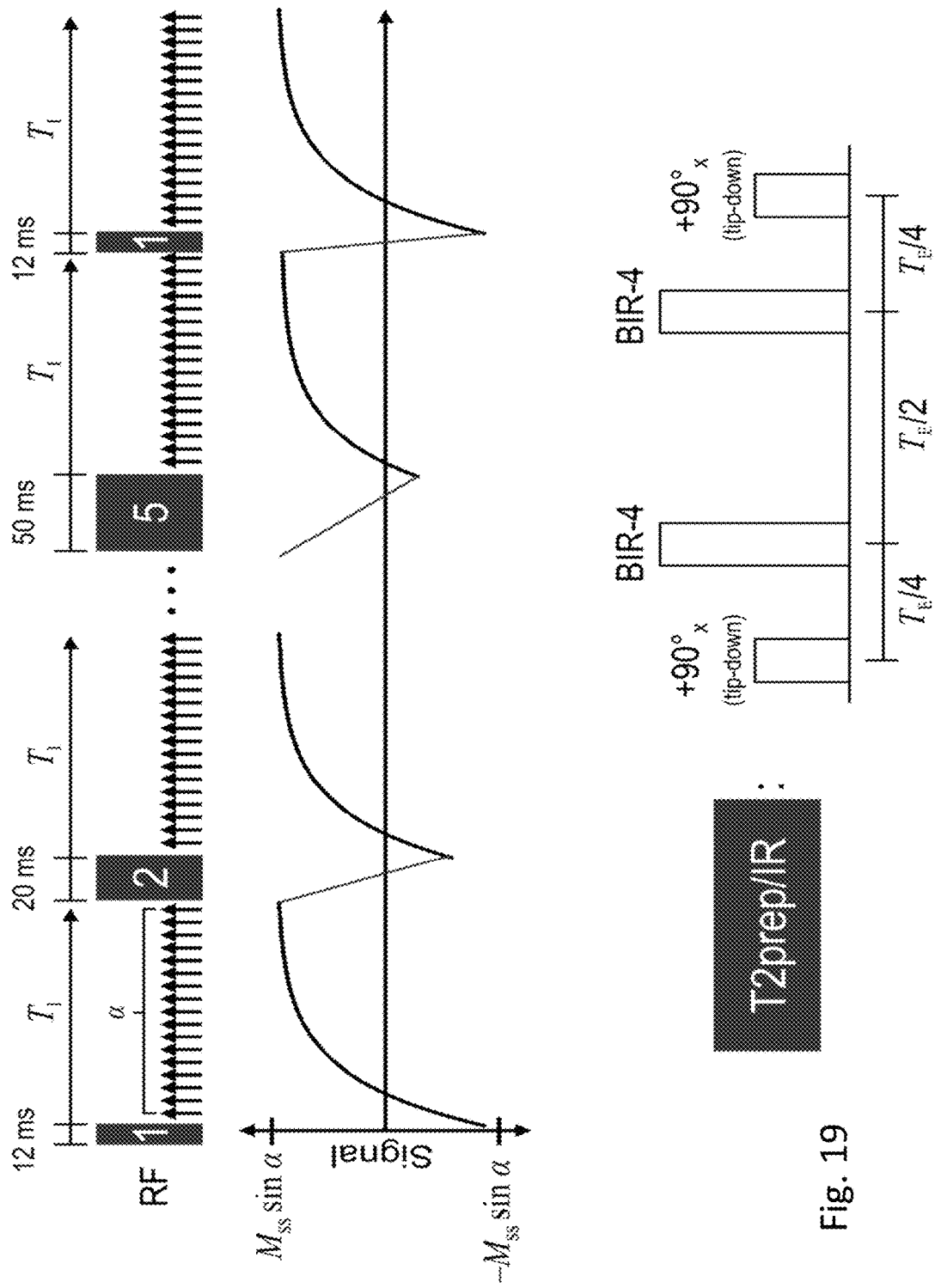
FIG. 19 shows a sequence diagram for T1-T2 mapping according to an embodiment.

FIG. 19 shows a sequence diagram for T1-T2 mapping. A continuous FLASH sequence was used to sample T1 recovery after different T2prep/IR pulses, which were cycled through choices of five different durations. The T2prep/IR pulse itself is a modified T2prep pulse with a 90° tip-down pulse at the end to achieve the effect of a 90° tip-up followed by 180° inversion.

Each prep pulse was followed by 5° FLASH readouts every 3.6 ms for 2.45 s; the prep pulse duration was cycled through 12, 20, 30, 40, and 50 ms. The process was repeated for a total duration of 85 s. Real-time low-rank matrix images were reconstructed first for image-based cardiac/respiratory binning. LRT image reconstruction was then performed with 15 cardiac bins, five respiratory bins, five T2prep durations, and 344 inversion times (3.6, 10.7, 17.8, . . . , 2446 ms).

Data were collected on a 3T Siemens Verio from n=5 healthy volunteers. To assess T1-T2 accuracy and repeatability, three scans each were collected of: diastolic T1 maps from ECG-triggered, breath-held SSFP MOLLI 5(3)3; diastolic T2 maps from ECG-triggered, breath-held T2prep-SSFP mapping; and multiphase T1-T2 maps from the proposed non-ECG, free-breathing method, all at 1.7 mm in-plane spatial resolution.

Figure 20:
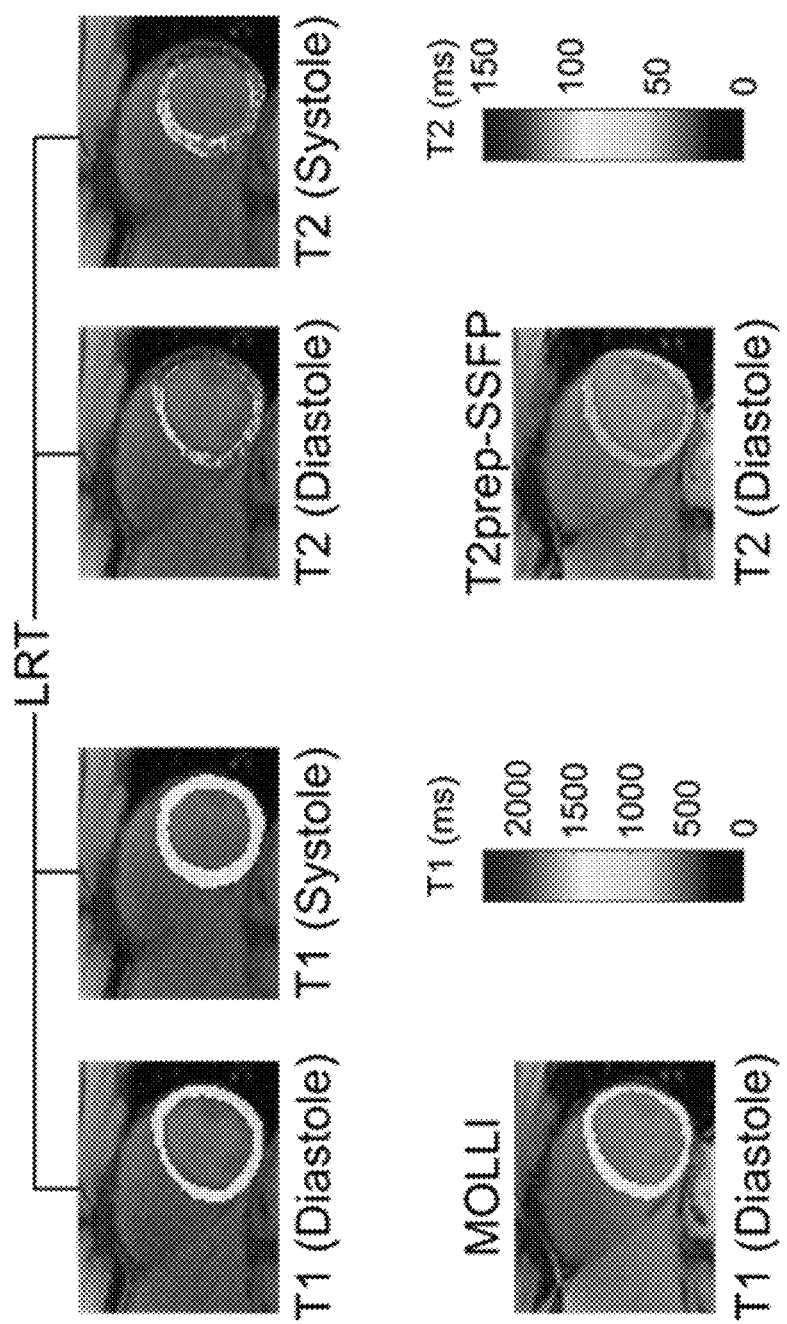
FIG. 20 shows diastolic and systolic T1-T2 maps from LRT, a diastolic T1 map from MOLLI, and a T2 map from T2prep-SSFP, all for the subject with median repeatability.

Results. FIG. 20 shows diastolic and systolic T1-T2 maps from LRT, a diastolic T1 map from MOLLI, and a T2 map from T2prep-SSFP, all for the subject with median repeatability. FIG. 21 shows a table that summarizes statistical findings from the three methods. The proposed method underestimated diastolic T1 compared to MOLLI with reduced precision (coefficient of variation: 5.4% vs. 0.6%), but yielded values within the range previously reported in the literature. This apparent bias may be an effect of the preparation scheme differences (T2prep/IR vs. IR) or from sequence differences (FLASH vs. SSFP). The proposed method yielded similar T2 measurements to T2prep-SSFP.

Conclusions. A method for non-ECG, free-breathing joint T1-T2 mapping using LRT imaging is presented, allowing T1 and T2 measurement at multiple cardiac and respiratory phases. Measurements were within the range reported in the literature, and were repeatable to 5.4% for T1 and 6.9% for T2. These results show the viability of non-ECG, free-breathing multiparameter mapping.

Example 10: Non-ECG First-Pass Myocardial Perfusion T1 Mapping Using CMR Multitasking As discussed above, quantitative myocardial perfusion MRI is confounded by ECG-triggering misfires and the nonlinear response of signal intensity to contrast agent concentration. Non-ECG, time-resolved T1 mapping could correct for these factors but has previously been too slow to perform myocardial T1 mapping. Here we propose a method for non-ECG, first-pass myocardial perfusion T1 mapping with single-bolus quantification, using the cardiovascular low-rank tensor (LRT) imaging framework for CMR multitasking (simultaneous imaging of multiple dynamics such as cardiac motion, T1 recovery, and contrast agent wash-in/out).

Methods. The proposed method used a continuous-acquisition SR-prepared single-slice 2D radial FLASH sequence with a golden-angle ordering scheme modified to collect LRT subspace training data. Each saturation pulse was followed by 10° FLASH readouts every 3.6 ms throughout the entire 300 ms recovery period. In-plane spatial-resolution was 1.7 mm; scan length was 45 s. Real-time low-rank matrix images were reconstructed first for image-based cardiac binning. LRT image reconstruction was then performed with three time dimensions indexing each heartbeat, 15 cardiac phases, and 42 saturation times (3.6, 10.7, 17.8, . . . , 295 ms).

Data were collected from n=8 healthy volunteers on a 3T Siemens Verio. To assess repeatability of absolute myocardial blood flow (AMBF) measurements at rest, two 0.1 mmol/kg doses of Gadovist were administered 20 to 30 minutes apart. Subjects were instructed to hold their breath until no longer comfortable, followed by shallow breathing. AMBF was calculated by fitting T1 at the LV blood pool and six myocardial segments, converting to $\Delta R1$, and performing Fermi deconvolution.

Figure 23:
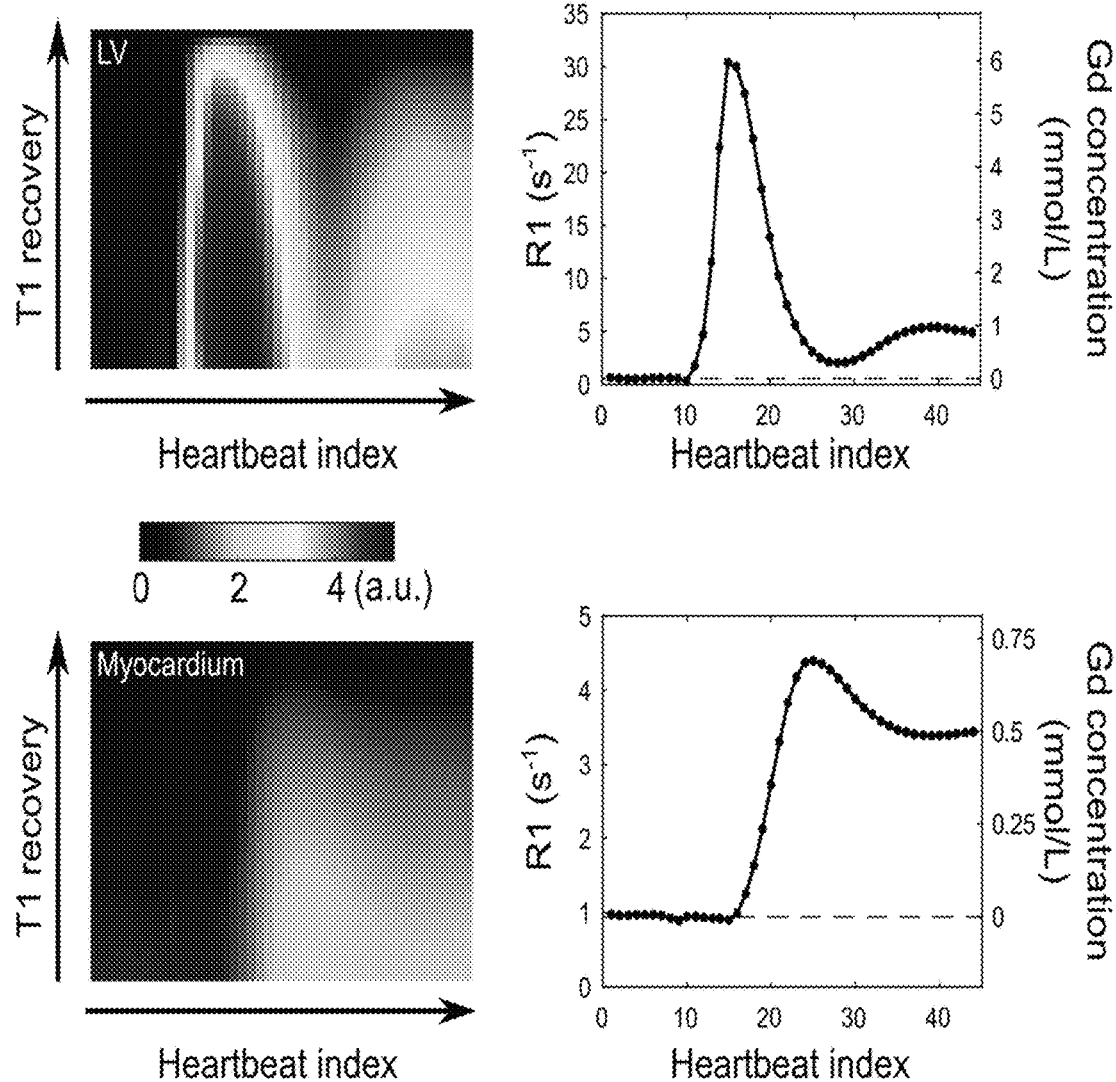
FIG. 23 shows LV and myocardial signal take the form of 2D surfaces when including saturation recovery.

Results. FIG. 22 demonstrates imaging of multiple cardiac phases as well as the passage of contrast agent. In particular, FIG. 22 shows example images showing contrast agent dynamics for both systole and diastole. Images shown are for saturation time=295 ms. FIG. 23 demonstrates the calculation of contrast agent concentration from signal intensity surfaces: the large number of saturation times and joint fitting across heartbeats allows measurement of a wide range of blood and myocardial T1's. In particular, FIG. 23 shows LV and myocardial signal take the form of 2D surfaces when including saturation recovery. Imaging saturation recovery permits T1 mapping followed by calculation of Gd concentration as $\Delta R1/\gamma$ where $\gamma$ is the relaxivity of the contrast agent.

The table in FIG. 24 lists measurement statistics aggregated over segments. There was a nonsignificant difference (p=0.40) between the first and second AMBF measurements, and flows were within the normal range from previous literature. The within-segment standard deviation of 0.30 g/mL/min compares favorably with other non-ECG methods.

Conclusions. The initial results of non-ECG first-pass myocardial perfusion T1 mapping are promising for single-bolus quantification of myocardial blood flow. AMBF measurements are robust to initial contrast agent concentration, with a nonsignificant difference between first and second boluses.

Example 11: Non-ECG First-Pass Myocardial Perfusion T1 Mapping with Low-Rank Tensor Cardiovascular MR Quantitative first-pass myocardial perfusion imaging is a potentially powerful tool for diagnosing coronary artery disease. However, as discussed above, quantification is complicated by ECG misfires and the nonlinear response of signal intensity to contrast agent concentration. Examined here is a method overcoming the curse of dimensionality to simultaneously image cardiac motion, contrast dynamics, and T1 relaxation in 2D and 3D, using a low-rank tensor imaging framework for cardiovascular MR multitasking. This non-ECG, first-pass myocardial perfusion T1 mapping method accounts for the signal intensity nonlinearity, allowing direct quantification of contrast agent concentration at any cardiac phase in any cardiac cycle First-pass myocardial perfusion imaging is a potentially powerful tool for diagnosing coronary artery disease. However, conventional ECG-triggered methods can misfire, skipping beats and confounding quantification, leading to interest in non-ECG methods. Quantification is further complicated by the nonlinear response of signal intensity to contrast agent concentration, which violates linear shift-invariant flow models. Time-resolved T1 maps could correct for this nonlinearity, but the curse of dimensionality presents a major barrier for simultaneous imaging of cardiac motion, contrast dynamics, and T1 relaxation. Here a method is examined for overcoming this barrier, enabling non-ECG, first-pass myocardial perfusion T1 mapping using a low-rank tensor (LRT) imaging framework for cardiovascular MR multitasking.

The method employed an ECG-free continuous-acquisition SR-FLASH prototype pulse sequence with readouts collected throughout the entire SR period. For 2D, radial acquisition was performed using a golden-angle ordering scheme, interleaved with 0° radial spoke acquisition every other readout as subspace training data. For 3D, stack-of-stars acquisition was performed with golden-angle ordering for the polar coordinates and variable-density Gaussian random sampling for $k_z$, interleaved with 0° spoke acquisition at k=0 every other readout.

Explicit-subspace low-rank matrix imaging was first used to obtain an image I(x,t') with a single "real-time" dimension t'. I(x,t') depicts the overlapping effects of cardiac motion, T1 recovery, and contrast agent dynamics, allowing image-based cardiac phase identification. The matrix Φ was estimated after LRT completion of the subspace training data. $\hat{U}_x$ was reconstructed according to Eq. 3, using spatial total variation as the regularization functional R(·).

To assess repeatability of resting myocardial blood flow (MBF) measurements, n=8 healthy volunteers were imaged on a 3 T Siemens Verio. Pulse sequence parameters were FA=10°, TR/TE=3.6/1.6 ms, FOV=270×270 mm, matrix size=160×160, spatial resolution=1.7×1.7 mm, and slice thickness=8 mm. Image reconstruction was performed for 15 cardiac bins and 42 saturation times. Two 0.1 mmol/kg doses of Gadovist were administered 20 to 30 minutes apart. Subjects were instructed to hold their breath for as much of the 45 s scan duration as possible, followed by shallow breathing. To demonstrate the feasibility of 3D imaging, the same process was performed for a healthy volunteer using FA=10°, TR/TE=5.9/2.7 ms, FOV=256×256×96 mm³, matrix size=128×128×12, spatial resolution=2.0×2.0×8.0 mm.

For quantification, $T_1(t)$ was calculated for the left ventricular (LV) blood pool and six myocardial segments in the 2D images at end-diastole. Contrast agent concentration was calculated as $$Gd(t) = \Delta R_1(t)/\gamma = \left(\frac{1}{T_1(t)} - \frac{1}{T_1(0)}\right)\Big/\gamma, \tag{19}$$

where γ is the T1 relaxivity of the contrast agent. Fermi deconvolution of each myocardial Gd(t) by the LV Gd(t) yielded MBF for each myocardial segment.

Figure 25:
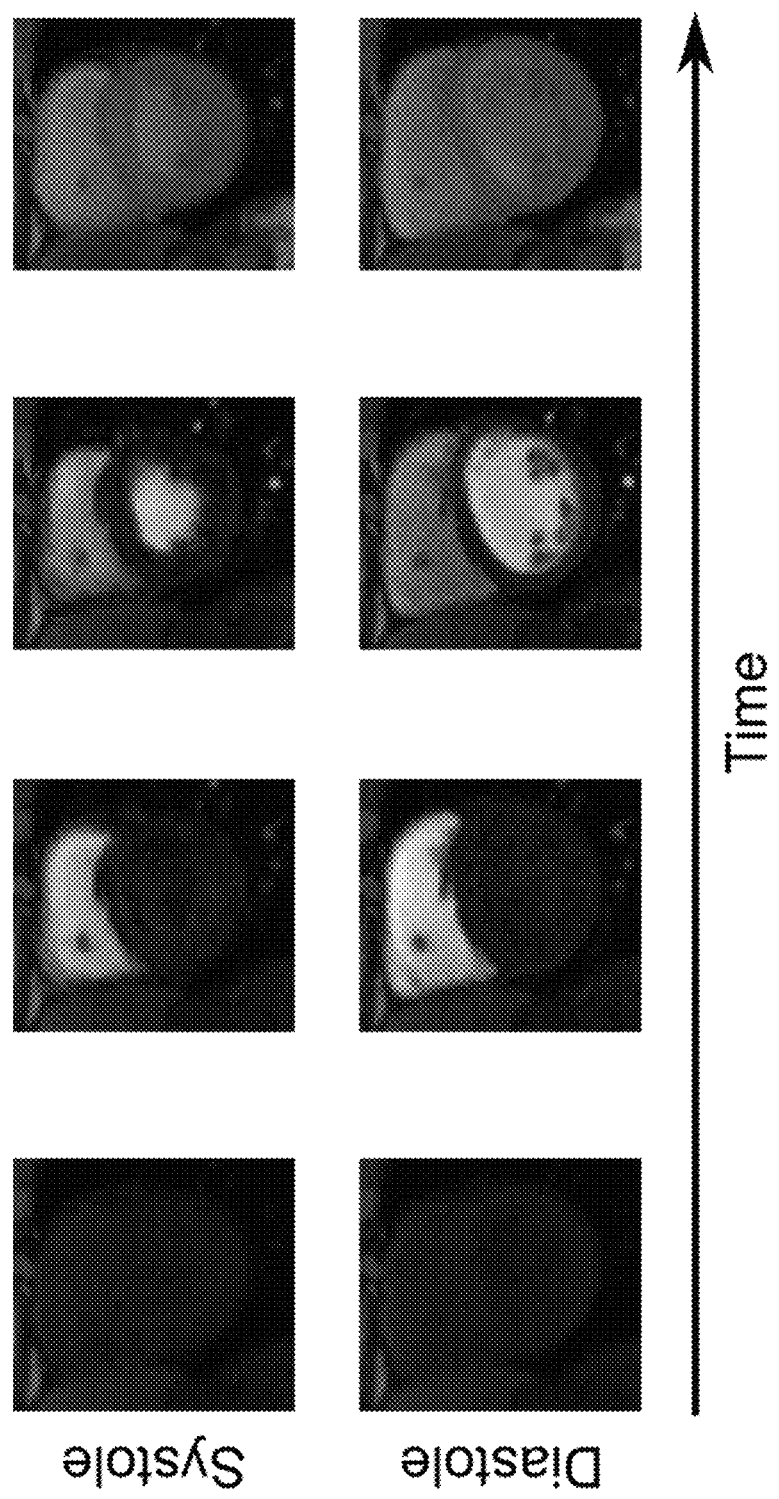
FIG. 25 shows example results showing contrast agent dynamics for both systole and diastole, pictured at one saturation recovery time.

Results. FIG. 25 demonstrates the ability of the proposed method to image multiple cardiac phases as well as the passage of contrast agent. In particular, FIG. 20 shows example results showing contrast agent dynamics for both systole and diastole, pictured at one saturation recovery time.

Figure 26:
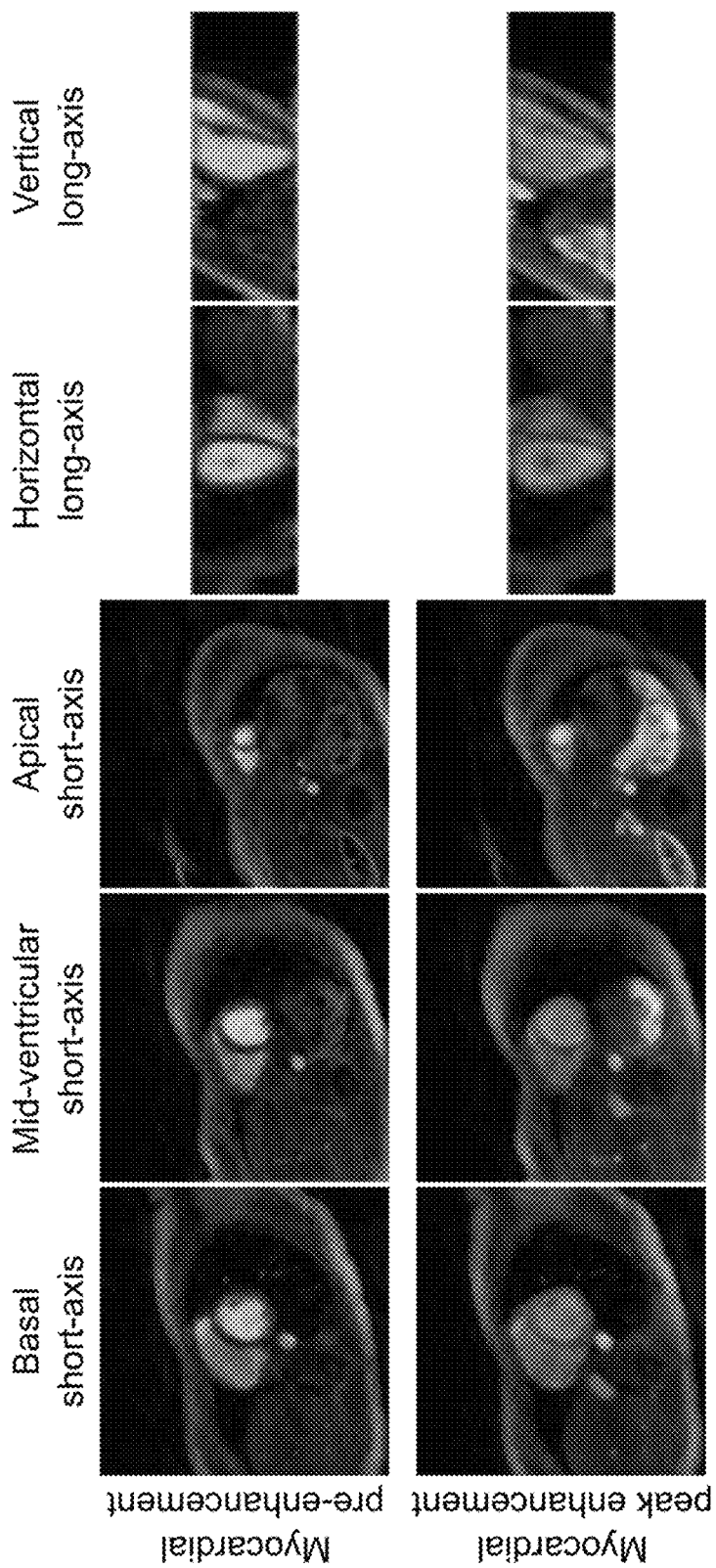
FIG. 26 shows example 3D results pre-myocardial enhancement and at peak myocardial enhancement, pictured at diastole for one saturation recovery time.

FIG. 26 depicts 3D results demonstrating the ability of the method to scale to whole-heart coverage. In particular, FIG. 26 shows example 3D results pre-myocardial enhancement and at peak myocardial enhancement, pictured at diastole for one saturation recovery time. This demonstrates the ability to scale to whole-heart imaging.

Figure 27:
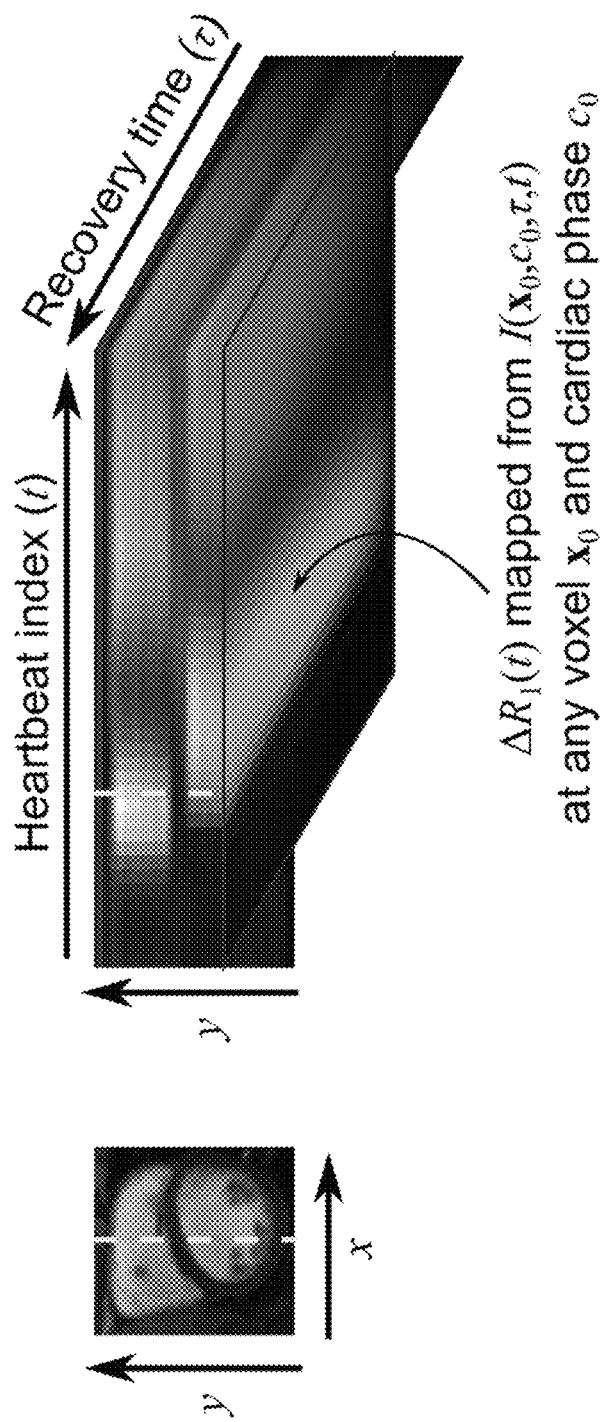
FIG. 27 shows signal intensity curves take the form of 2D surfaces when including saturation recovery.

FIG. 27 illustrates how with multiple saturation times, signal intensity curves become surfaces. In particular, FIG. 27 shows signal intensity curves take the form of 2D surfaces when including saturation recovery. $\Delta R_1(t)$ can be mapped from these surfaces.

Figure 28:
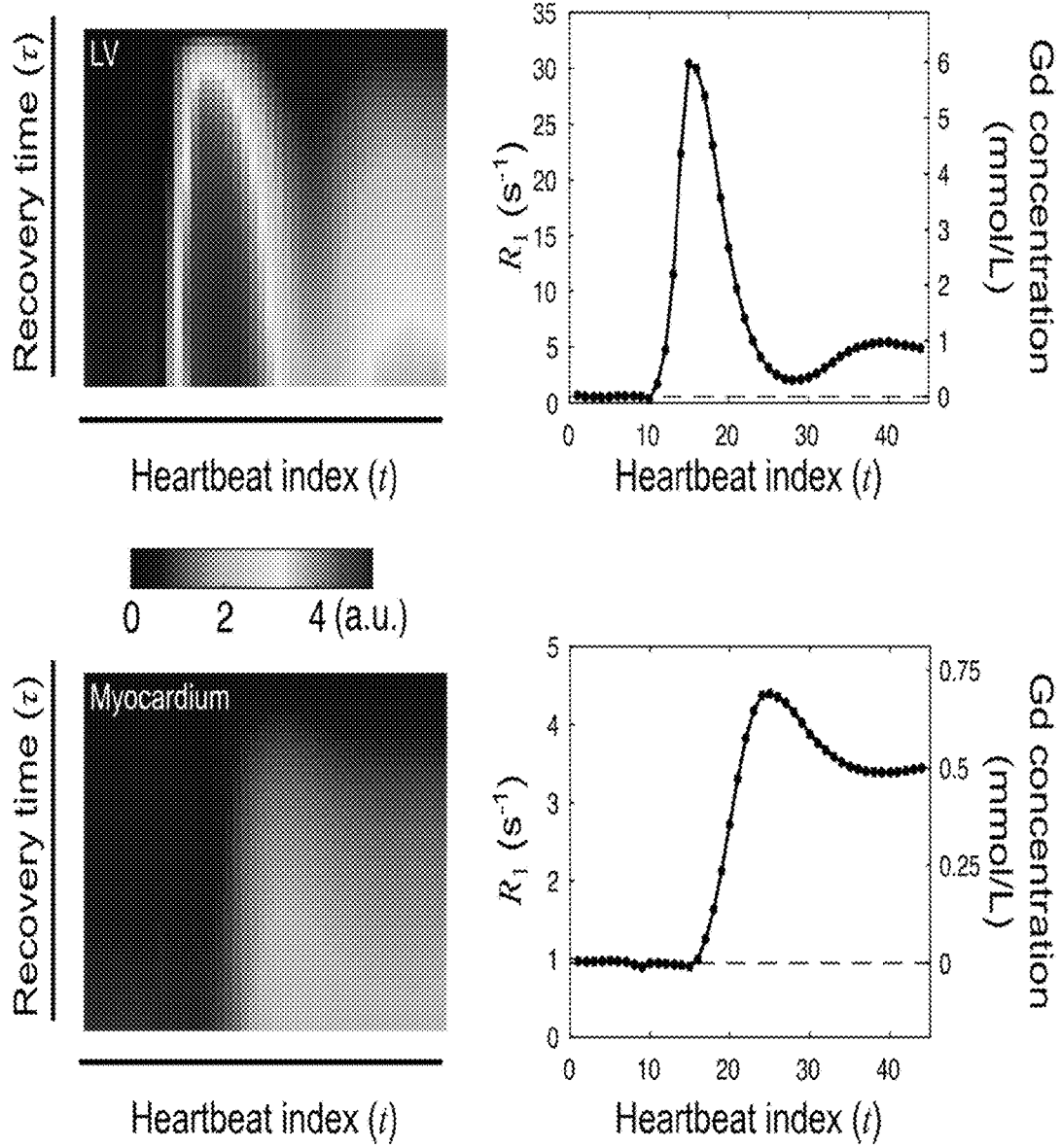
FIG. 28 shows time-resolved T1 mapping allows direct calculation of Gd concentration as $\Delta R_1/\gamma$, where $\gamma$ is the relaxivity of the contrast agent.

FIG. 28 demonstrates how joint fitting of T1 values at different time points from these surfaces yields Gd(t). In particular, FIG. 28 shows time-resolved T1 mapping allows direct calculation of Gd concentration as $\Delta R_1/\gamma$, where γ is the relaxivity of the contrast agent.

FIG. 29*a* shows the two-way ANOVA table indicating a nonsignificant difference (p=0.44) between repetitions as well as a nonsignificant difference (p=0.47) between segments, as expected for healthy volunteers. FIG. 29*b* lists repeatability statistics aggregated over segments. MBF was within the normal range from previous literature, and the within-segment standard deviation of 0.30 g/mL/min compares favorably with other non-ECG methods.

Conclusions. The proposed method for non-ECG first-pass myocardial perfusion T1 mapping is promising for quantitative myocardial perfusion. The repeatability study shows that 2D MBF measurements are robust to initial contrast agent concentration, demonstrating nonsignificant difference in MBF between first and second boluses.

Example 12: Quantitative 3D Dynamic Contrast Enhanced (DCE) Imaging of Carotid Vessel Wall by Fast T1 Mapping Dynamic contrast enhanced (DCE) MRI is a promising technique to quantitatively evaluate the inflammatory status of atherosclerosis noninvasively. However, its demanding sampling requirement leads to sacrifices in slide resolution, coverage, and/or temporal resolution in the applications to vessel wall imaging. In this work we designed accelerated dynamic T1-mapping technique using Low Rank Tensor (LRT) framework to achieve 3D high-resolution quantitative DCE of the carotid arteries.

Dynamic Contrast Enhanced (DCE) MRI enables quantitative assessment of microvasculature and endothelial permeability in the adventitial vaso vasorum. The application of DCE in carotid vessel wall imaging faces demanding sampling challenges: 1) submillimeter spatial resolution is required for visualizing vessel wall without significant partial volume effects; 2) high temporal resolution is required to accurately capture the contrast kinetics; 3) adequate anatomical coverage is needed to cover the entire vasculature. Therefore, compromises often have to be made, for example, as poor slide resolution in conventional 2D acquisition, or reduced temporal resolution in 3D acquisition. Signal intensity in DCE does not scale linearly with contrast agent concentration, thus introducing errors in kinetic modeling such as saturated arterial input function (AIF). In this study, we attempted to mitigate these limitations to achieve high-resolution (0.7 mm isotropic) 3D DCE imaging with dynamic T1 mapping.

Methods. A dynamic T1 mapping method was designed based on the Low-Rank Tensor (LRT) framework to exploit the high correlation between images with different saturation recovery times and different contrast enhancement phases to allow vastly accelerated imaging.

Sequence Design: A saturation recovery-prepared low angle shot readout (SR-FLASH) was employed (FIG. 1). Cartesian acquisition with randomized reordering in ky and kz directions was implemented according to a variable-density Gaussian distribution. A k-space center line was collected every 8 lines as training data for the LRT subspace.

Imaging Protocol: All data were acquired on a 3T Siemens Verio scanner. Accuracy of T1 mapping was tested in T1 phantoms and compared with a standard inversion-prepared spin echo method. Normal subjects without known carotid atherosclerosis (N=6) were scanned using the following parameters: coronal orientation, spatial resolution=0.7 mm isotropic, FOV=150×150×26 mm$^3$, α=8°, TR=600 ms, scan time=12 mins, DCE temporal_footprint=2.08s. Gd contrast media was administered at the rate of 1.0 ml/sec with 20 ml saline flush (Gadovist, 0.1 mmol/kg).

Motion Correction: An automatic algorithm was developed to exclude and interpolate the motion-corrupted data in the tensor based on spike detection in the principal temporal basis function of the LRT subspace.

Result

Figure 30A:
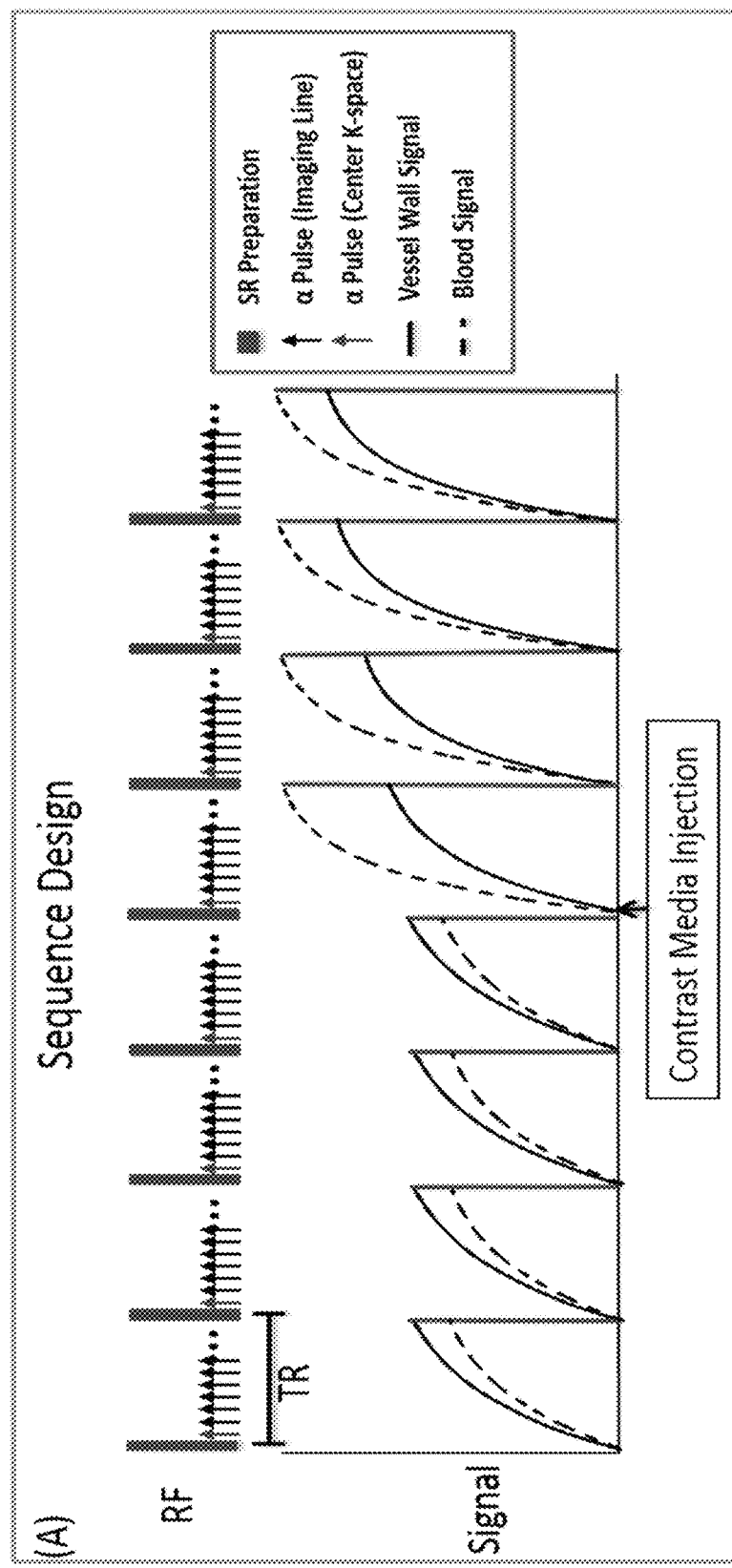
FIG. 30a shows a pulse sequence diagram for accelerated 3D DCE and corresponding simulated signal evolution for vessel wall and blood.
Figure 30B:
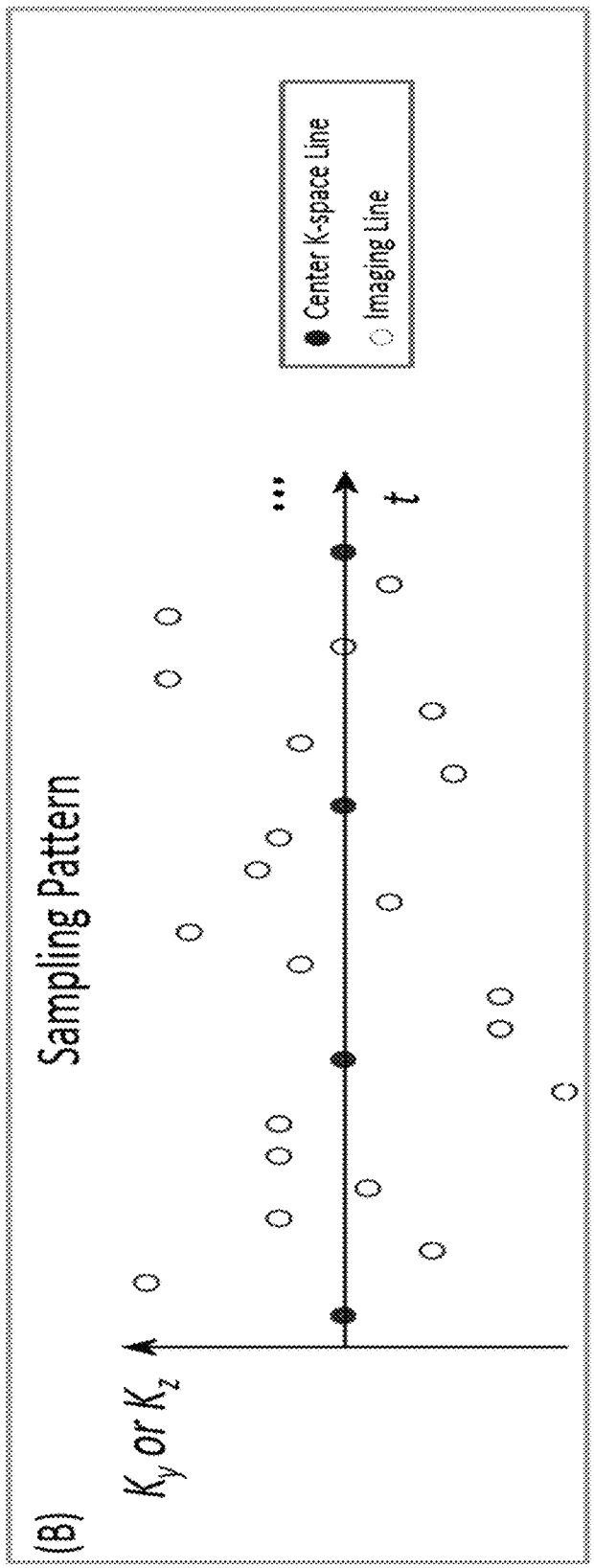
FIG. 30b shows a simplified illustration of k-space sampling strategy.

FIG. 30$a$ shows a pulse sequence diagram for accelerated 3D DCE and corresponding simulated signal evolution for vessel wall and blood. Saturation recovery preparation is applied every TR followed by a series of alpha pulses. The entire k-space is traversed for 10 times with 52 lines acquired during each TR. FIG. 30$b$ shows a simplified illustration of k-space sampling strategy. Cartesian acquisition with randomized reordering in ky and kz directions is implemented according to a variable-density Gaussian distribution. A center k-space line is acquired every 8 lines as the training data for LRT subspace.

Figure 31:
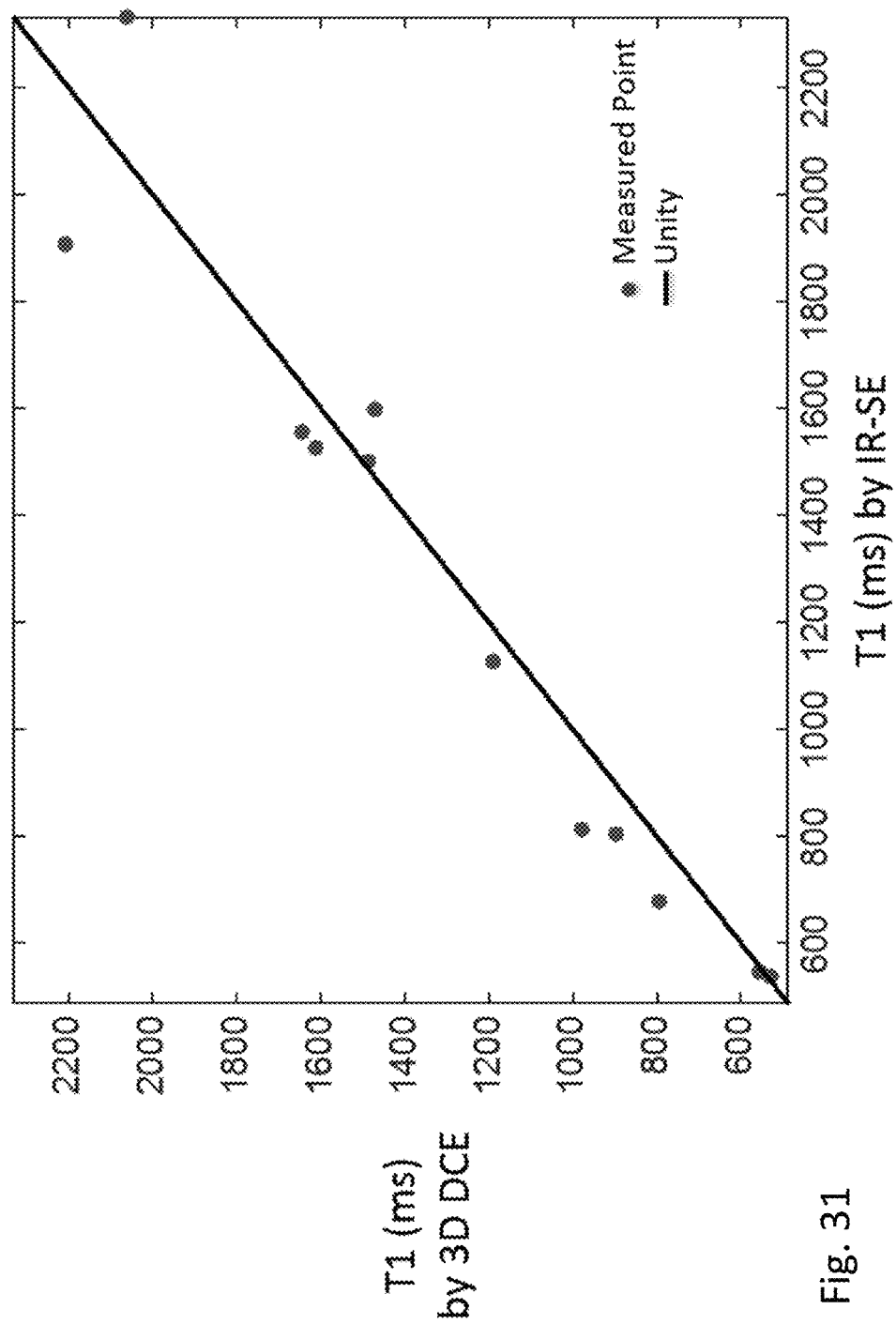
FIG. 31. Comparison of T1 quantification using the proposed DCE method versus a standard reference method (IR-spin echo) in the phantom study, showing high agreement (r=0.97, p<0.001). The solid line represents y=x.

FIG. 31. Comparison of T1 quantification using the proposed DCE method versus a standard reference method (IR-spin echo) in the phantom study, showing high agreement (r=0.97, p<0.001). The solid line represents y=x.

Figure 32:
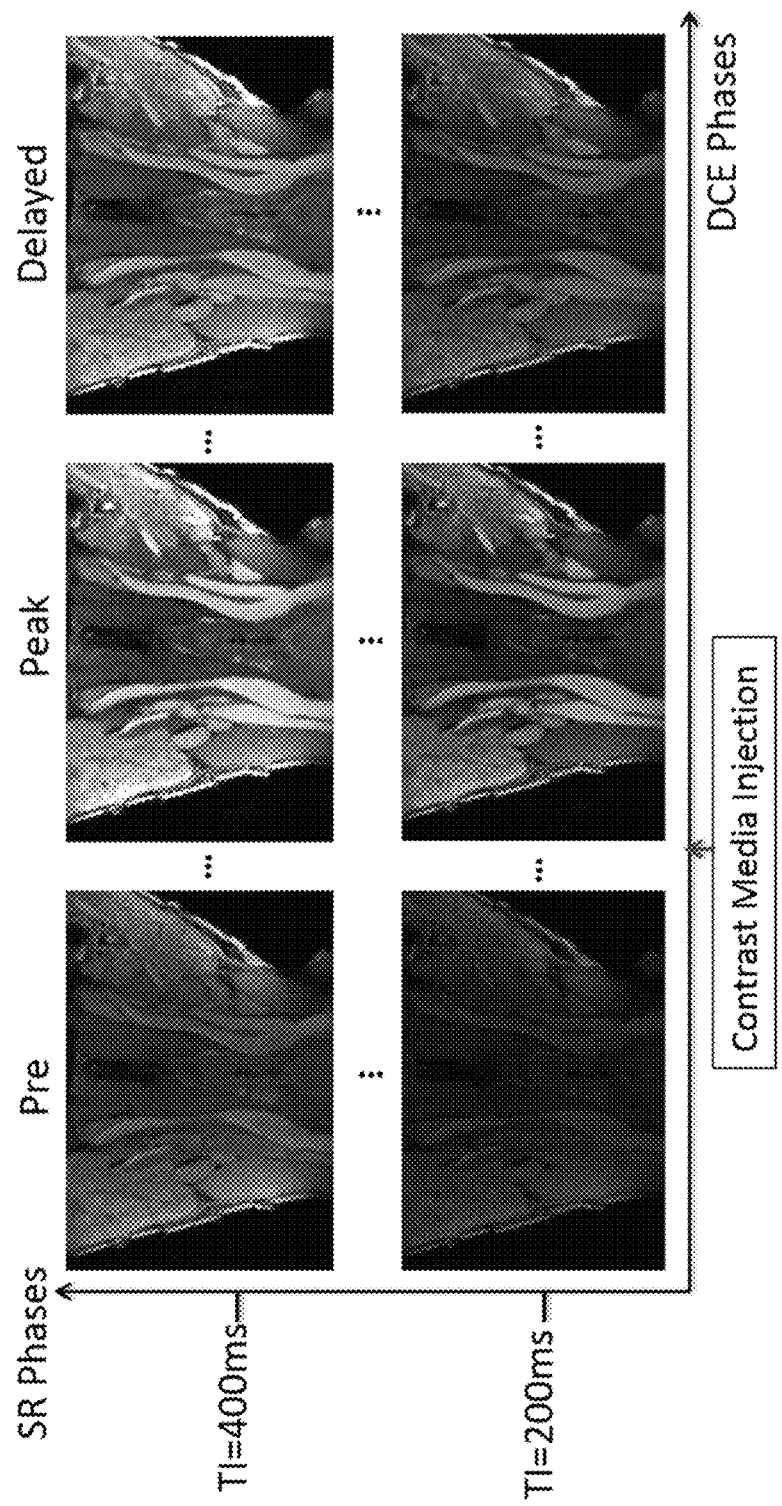
FIG. 32 is a representative image set from a 3D DCE study of a normal subject using the proposed technique.

FIG. 32 is a representative image set from a 3D DCE study of a normal subject using the proposed technique. Multi-phase images are reconstructed with the LRT framework in the contrast dimension (images at different SR TI times) and dynamic enhancement dimension (images at different time after injection). Multiple SR phases allows T1 quantification and direct estimation of contrast concentration. Three key DCE phases are shown along horizontal axis, including pre-injection, peak enhancement, and washing out. DCE temporal footprint is 2.08 seconds.

Figure 33:
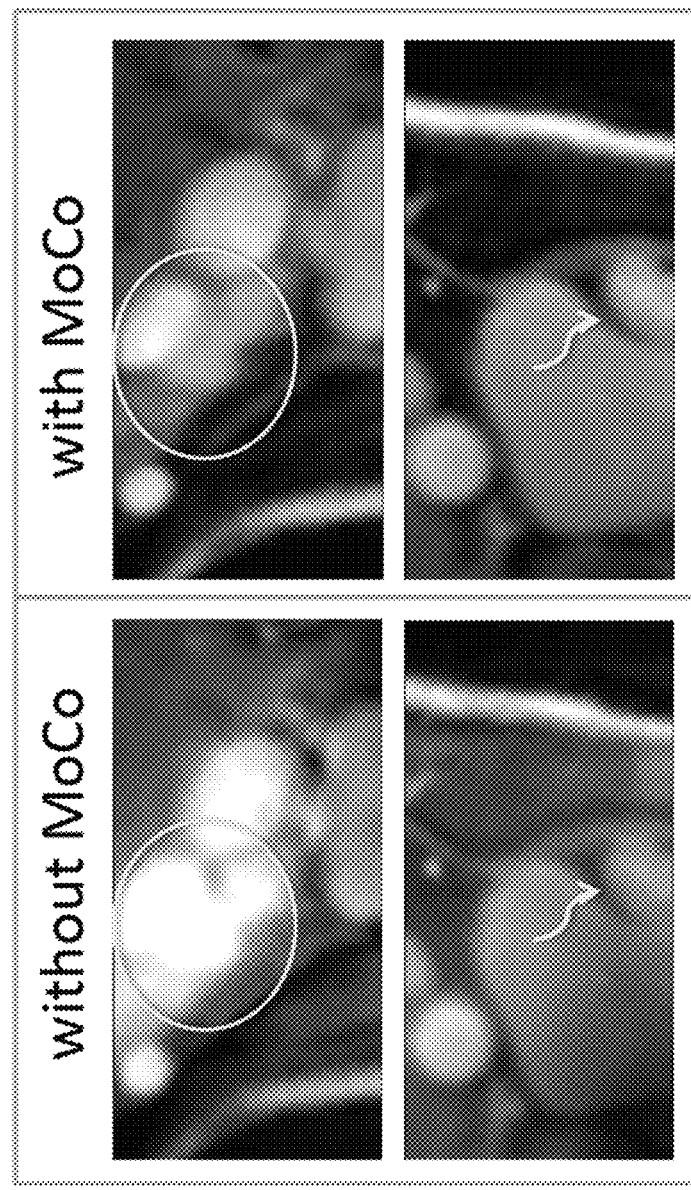
FIG. 33 shows the effects of motion correction in the proposed 3D DCE technique.

FIG. 33 shows the effects of motion correction in the proposed 3D DCE technique. Long scan in DCE studies (>12 mins) often lead to motion artifacts which blur images and introduce artifacts. Reconstructed images with motion correction showed sharper and superior delineation of different tissue types.

Figure 34A:
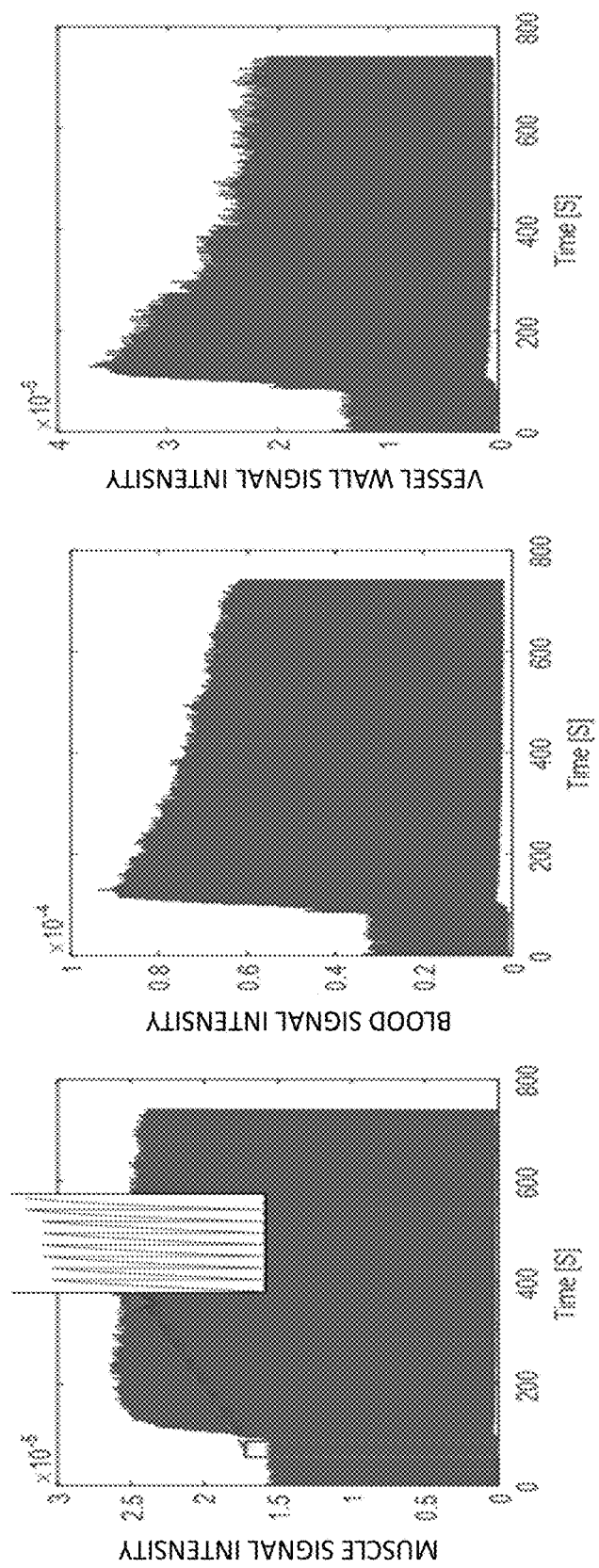
FIG. 34a shows real-time signal evolution of different tissue types in a normal subject measured from the multiphase DCE images. Zoom-in area shows the SR recovery curves at the beginning of the contrast injection.
Figure 34B:
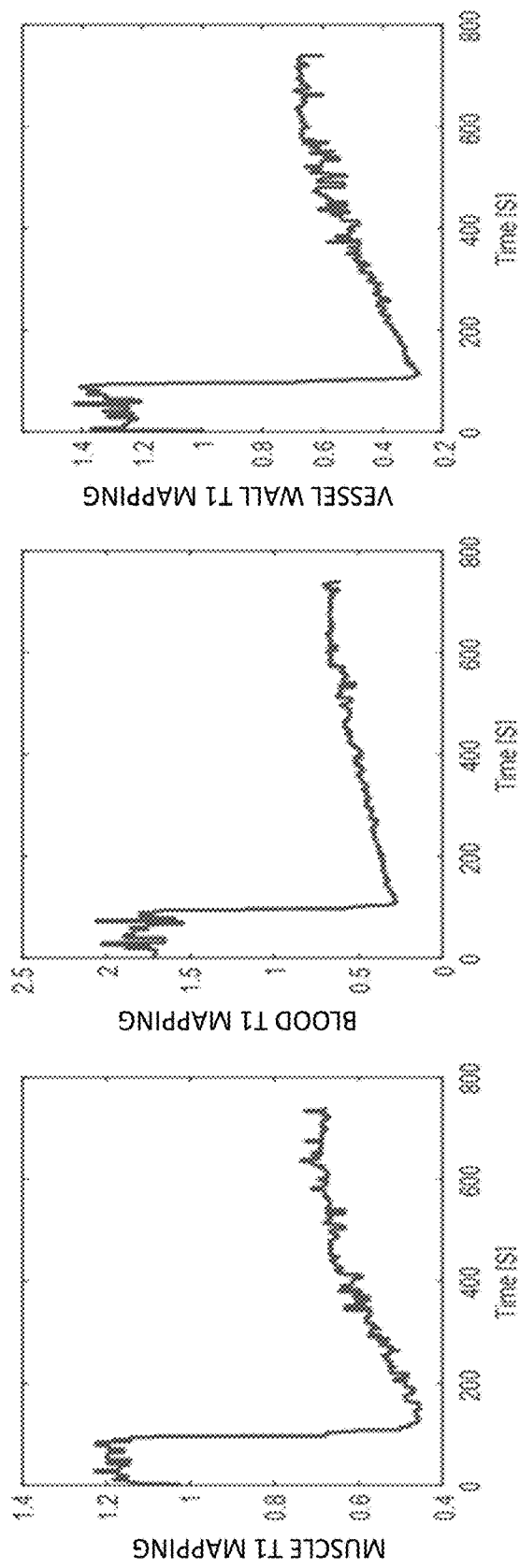
FIG. 34b shows dynamic T1 mapping of different tissue types.
Figure 34C:
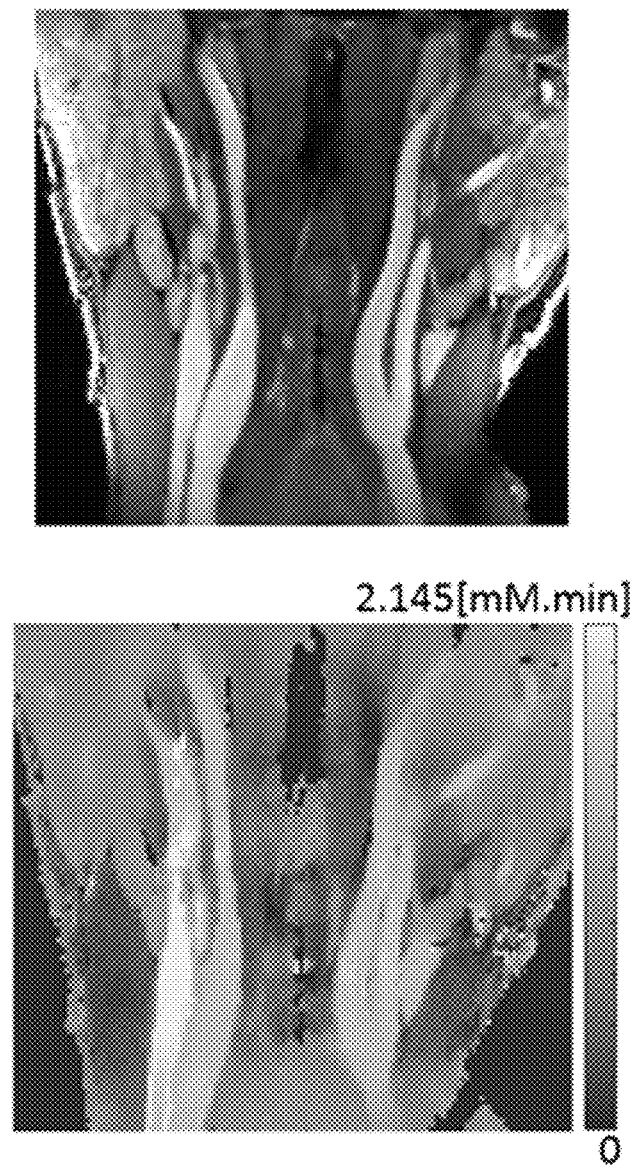
FIG. 34c shows mapping of the AUC (area under the curve), a measure for contrast media extravasation.

FIGS. 34$a$-$c$ show the real-time signal evolution, dynamic T1 mapping, and AUC mapping. Vessel wall vp and Ktrans was 0.276 and 0.121±0.02 min$^{-1}$, respectively. In particular, FIG. 34$a$ shows real-time signal evolution of different tissue types in a normal subject measured from the multi-phase DCE images. Zoom-in area shows the SR recovery curves at the beginning of the contrast injection. FIG. 34$b$ shows dynamic T1 mapping of different tissue types. FIG. 34 $c$ shows mapping of the AUC (area under the curve), a measure for contrast media extravasation.

Discussion Kinetic modeling was feasible based on the in vivo DCE data. Motion correction alleviated the bulk motion issues which were frequent during DCE scans. The vessel wall in normal subjects is thin which added difficulty in accurate segmentation. For in vivo study, automated image processing is needed to quantify the multi-phase images.

Conclusion. We have demonstrated the feasibility of high resolution (0.7 mm) 3D DCE imaging of carotid arteries based on dynamic T1 mapping. Studies on phantom and human subjects showed excellent image quality, accurate T1 quantification, and robustness to motion. Patient study is warranted to investigate the potential benefits of the proposed technique.

Example 13: Quantitative Multi-Contrast Atherosclerosis Characterization (qMATCH): Comprehensive Quantitative Evaluation of Atherosclerosis in a Single-Scan Although MRI is an attractive imaging modality for the evaluation of carotid atherosclerosis thanks to its versatility and noninvasiveness, its current clinical usage is still limited. Major drawbacks of conventional protocols include long scan time and observer variability due to the qualitative nature of the images. In this work we proposed a fast, 3D, quantitative, multi-contrast MRI technique, qMATCH, for a comprehensive evaluation of carotid atherosclerosis in less than 8 minutes. Preliminary results from phantom and in vivo studies demonstrated excellent image quality and reliable quantification of tissue relaxation times.

Purpose

MRI is a preferred imaging modality for the evaluation of carotid atherosclerosis, with the capability to provide multi-faceted diagnostic information on both luminal stenosis as well as plaque composition through various image contrasts. Recently, we developed the MATCH technique as a single-scan solution for multi-contrast carotid imaging, offering much shortened exams and co-registered images. Because of their qualitative nature, however, multi-contrast images from MATCH still suffer from the same intra/inter-observer variability as conventional protocols. Quantitative mapping of the carotid vessel wall potentially offers high reproducibility and portability of the results. In this study, we extended the concept of MATCH to develop an accelerated MR technique for comprehensive evaluation of carotid atherosclerosis (including bright-blood MRA, dark-blood wall images, multiple T1/T2 weightings and quantitative mapping) in a single scan under 8 minutes.

Methods. The qMATCH technique was designed based on low-rank tensor (LRT) framework which exploits the partial separability of space and contrast dimensions in the multi-contrast images to achieve vast acceleration.

Figure 35:
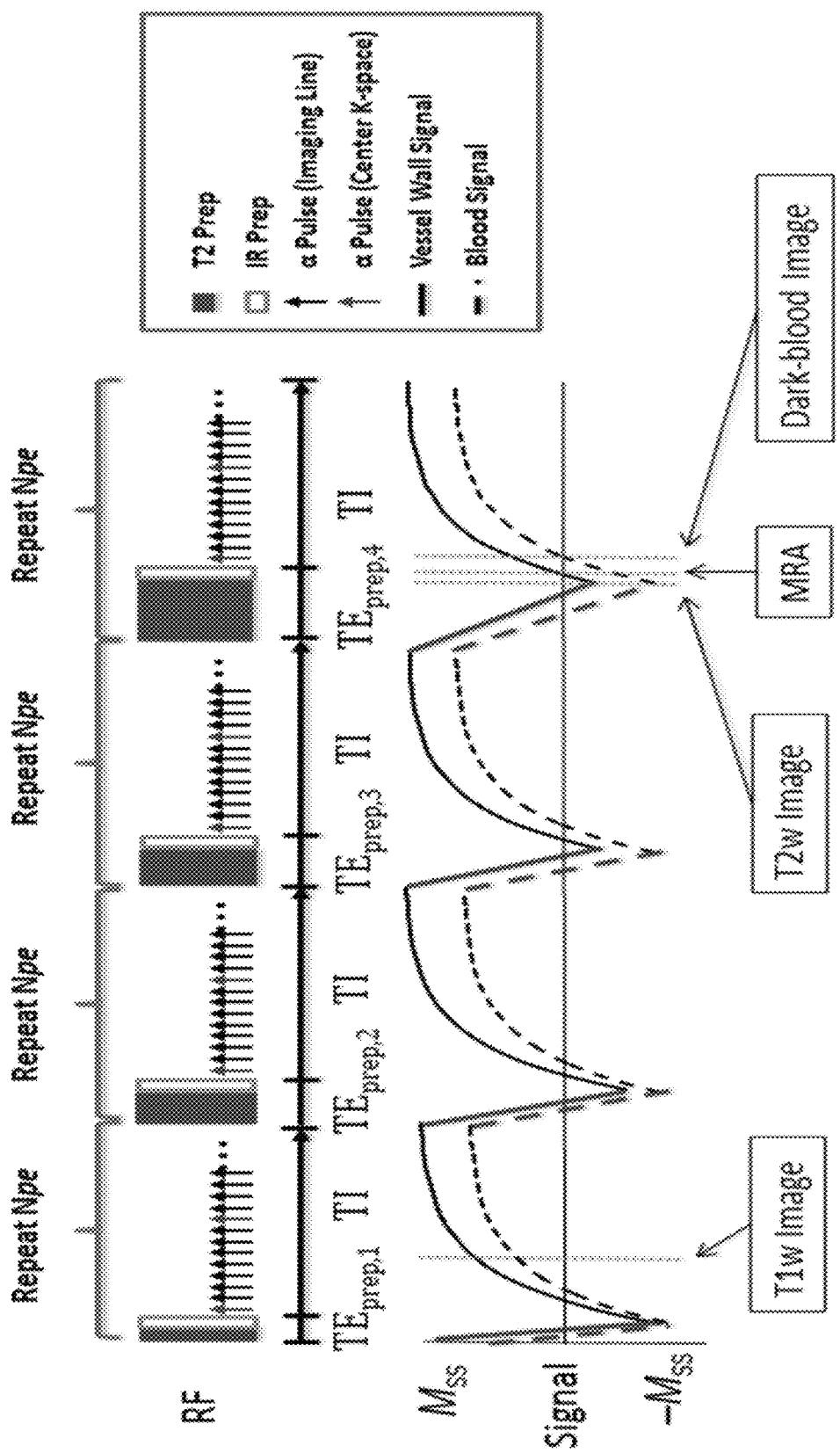
FIG. 35 shows a pulse sequence diagram for qMATCH and corresponding simulated signal evolution.
Figure 36:
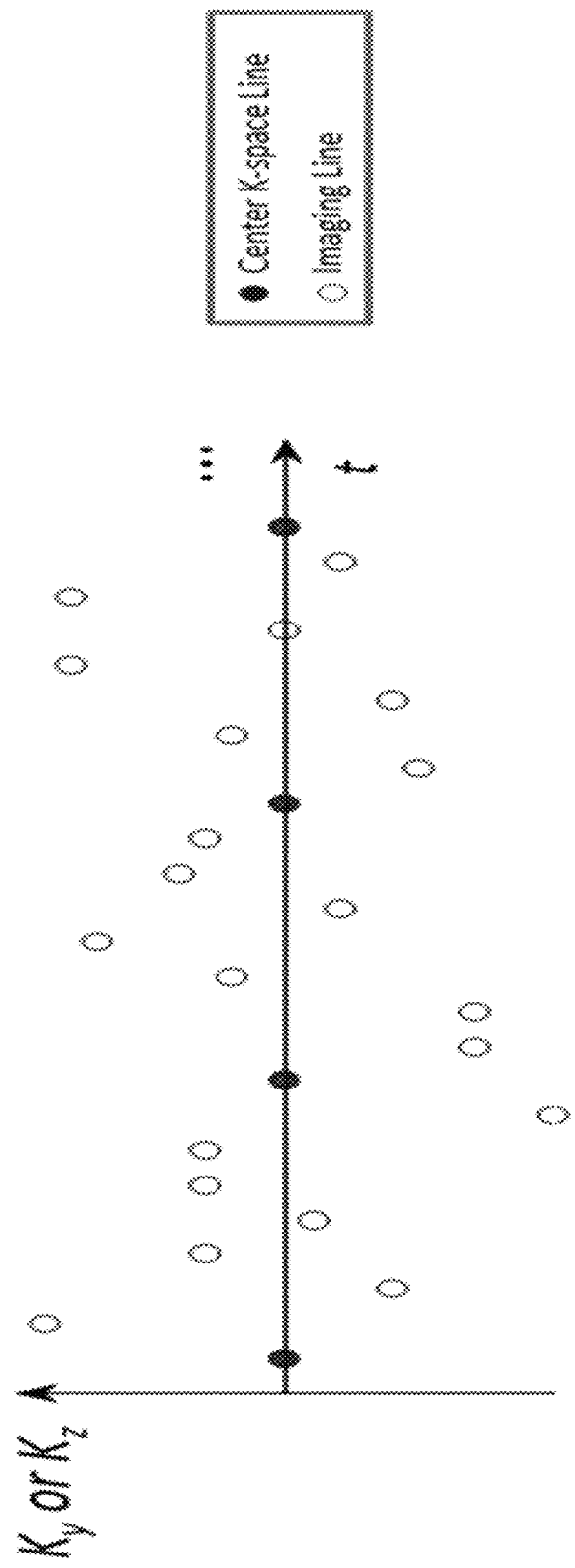
FIG. 36 shows an illustration of k-space sampling pattern for qMATCH.

Sequence implementation: qMATCH employed 3D flow-compensated spoiled gradient echo readout with variable-duration T2-IR preparations to generate T1 and T2 contrast (FIG. 35). Cartesian acquisition with randomized reordering in ky and kz directions was implemented according to a variable-density Gaussian distribution (FIG. 36). The center k-space line was collected every eighth readout to serve as LRT training data.

Imaging protocol: All data were acquired on a 3T Siemens Verio scanner with the following parameters: coronal orientation, spatial resolution=0.7 mm isotropic, FOV=150× 150×26 mm$^3$, α=8°, TR=2.08s, TEs=20/30/40/50/60/70 ms, scan time=7.5 mins. qMATCH was tested in relaxometry phantoms made of nickel chloride (for T1) and agarose (for T2). In vivo imaging was performed in 7 normal subjects without known carotid atherosclerosis. Standard IR spin echo was used as the reference in the phantom studies. MOLLI and T2prep SSFP was used as the reference in vivo Results FIG. 35 shows a pulse sequence diagram for qMATCH and corresponding simulated signal evolution. The four sequence blocks shown in this diagram each has different duration of T2 preparation and is repeated Npe times (Npe=partition encoding steps). MRA, dark-blood vessel wall, T1-weighted and T2-weighted images are collected at the null point of vessel wall, null point of blood, half-inversion period of the shortest T2IR prep and right after the longest T2IR prep, respectively.

FIG. 36 shows an illustration of k-space sampling pattern for qMATCH. A 3D Cartesian trajectory is used with random reordering in the phase/partition encoding directions (ky and kz). A variable-density sampling scheme following the Gaussian distribution allows higher sampling density in the central part of k-space. A center k-space line (ky=kz=0) was acquired every eight readout lines for LRT training data.

Figure 37:
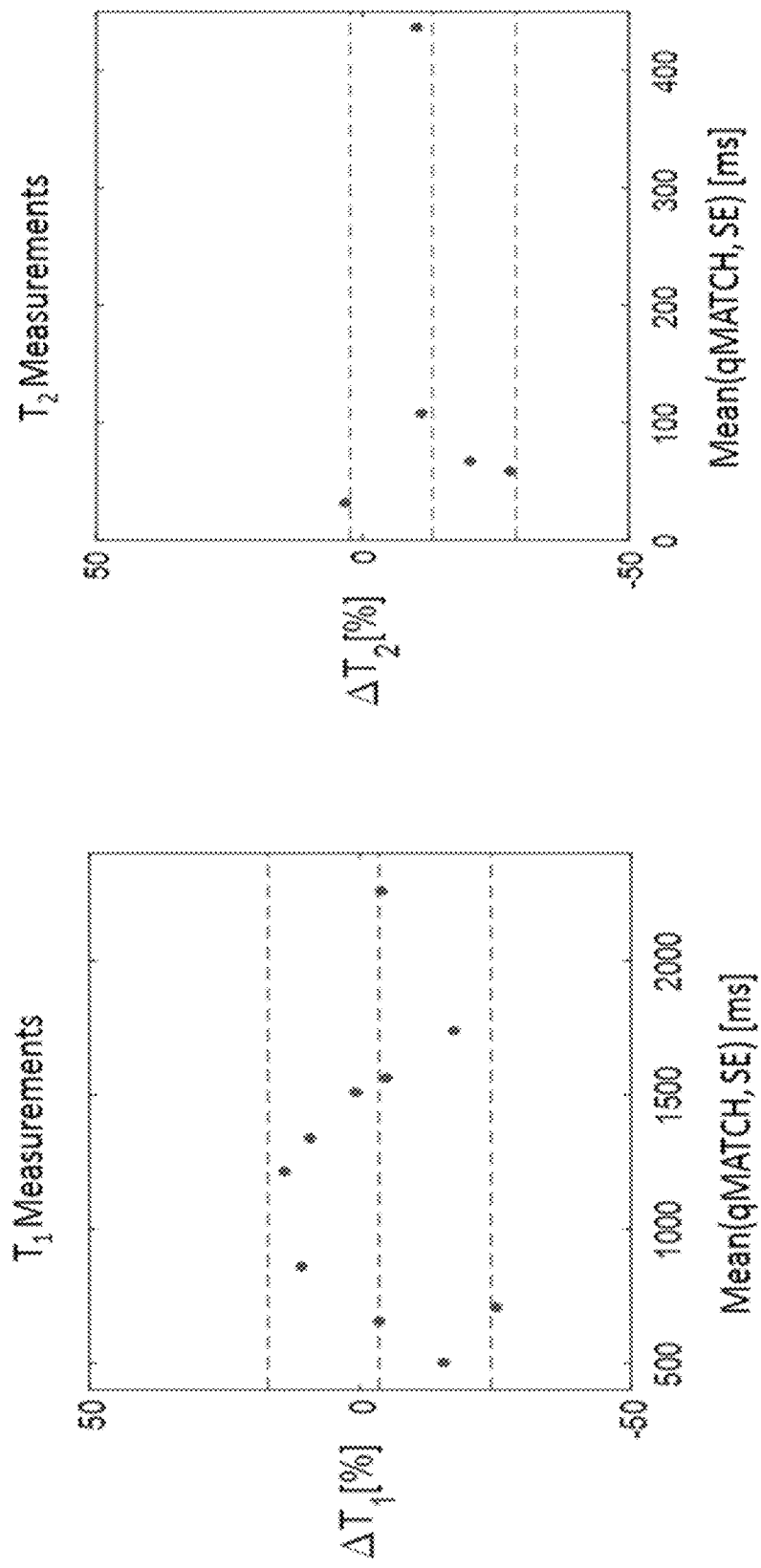
FIG. 37 shows T1 and T2 quantification comparison between qMATCH and reference method (2D standard spin echo) in the phantom study.

FIG. 37 shows T1 and T2 quantification comparison between qMATCH and reference method (2D standard spin echo) in the phantom study. Bland-Altman plot shows the mean value and relative difference between the two methods. Dashed lines indicate the mean and 95% confidence intervals for ΔT1 and ΔT2.

Figure 38:
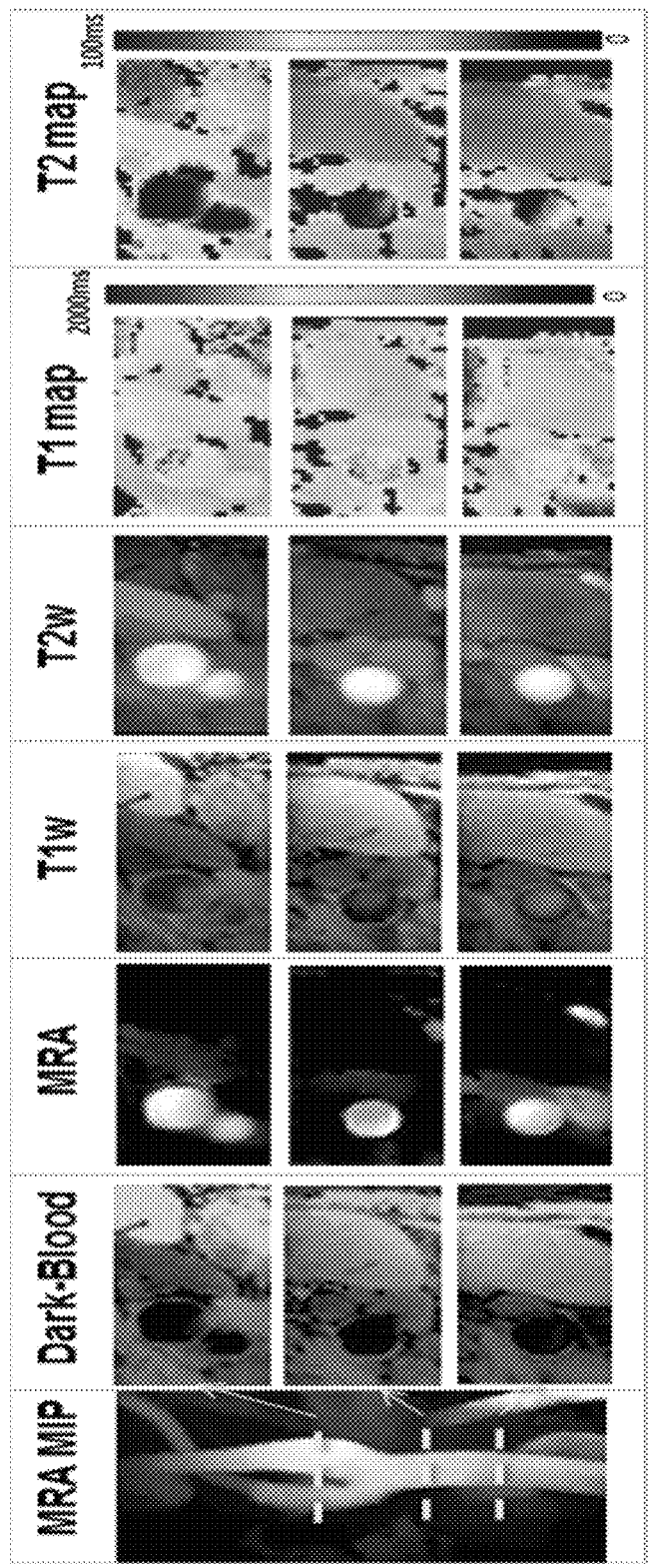
FIG. 38 shows a representative qMATCH image set from a normal subject. MRA MIP: coronal MIP of qMATCH MRA images.

FIG. 38 shows a representative qMATCH image set from a normal subject. MRA MIP: coronal MIP of qMATCH MRA images. Three transversal slices are shown to represent the multi-contrast images offered by qMATCH: Dark-Blood for visualizing vessel wall; MRA for visualizing lumen; T1-weighted and T2-weighted images for qualitative plaque characterization; and T1 and T2 mapping for quantitative plaque characterization.

FIG. 39 shows a table for comparison between the in vivo T1 and T2 mapping results from qMATCH and 2D reference methods (MOLLI and T2prep SSFP). Mean and standard deviation of muscle, blood and vessel wall are presented. All values are presented in milliseconds.

Discussion Preliminary results from phantoms and normal subjects demonstrated excellent multi-contrast image quality and reliable T1 and T2 quantification by qMATCH. High-resolution 3D coronal acquisition allowed large coverage and flexible viewing. All qMATCH images in a set are inherently co-registered which may simplify their usage in a clinical setting. Some luminal blood signal inhomogeneity and T1 errors were likely due to inflow effects.

Conclusion. The proposed qMATCH technique is a promising method for comprehensive evaluation of carotid atherosclerosis in a single scan. It has the potential to provide integrated assessment of multiple lesion characteristics including luminal stenosis (by bright-blood MRA), plaque burden (by dark-blood wall images), and plaque composition (by multiple T1/T2 weightings and quantitative mapping).

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

The following documents are provided to explain various aspects of the present invention. Their contents are incorporated herein by reference in their entirety.

1. Kolda T G, Bader B W. Tensor decompositions and applications. SIAM Rev. 2009; 51(3):455-500.
2. Liu J, Spincemaille P, Codella N C, Nguyen T D, Prince M R, Wang Y. Respiratory and cardiac self-gated free-breathing cardiac CINE imaging with multiecho 3D hybrid radial SSFP acquisition. Magnetic resonance in medicine. 2010; 63(5):1230-7.
3. Pang J, Sharif B, Fan Z, Bi X, Arsanjani R, Berman D S, Li D. ECG and navigator-free four-dimensional whole-heart coronary MRA for simultaneous visualization of cardiac anatomy and function. Magn Reson Med. 2014; 72(5):1208-17.
4. Adluru G, McGann C, Speier P, Kholmovski E G, Shaaban A, DiBella E V. Acquisition and reconstruction of undersampled radial data for myocardial perfusion magnetic resonance imaging. Journal of Magnetic Resonance Imaging. 2009; 29(2):466-73.
5. Feng L, Axel L, Chandarana H, Block K T, Sodickson D K, Otazo R. XD-GRASP: Golden-angle radial MRI with reconstruction of extra motion-state dimensions using compressed sensing. Magn Reson Med. 2016; 75(2):775-88.
6. Liang Z-P, Spatiotemporal imaging with partially separable functions. Proc IEEE Int Symp Biomed Imaging; 2007 12-15 Apr. 2007; Arlington, Va. 2007.
7. Pedersen H, Kozerke S, Ringgaard S, Nehrke K, Kim W Y. k-t PCA: Temporally constrained k-t BLAST reconstruction using principal component analysis. Magn Reson Med. 2009; 62(3):706-16.
8. Huang C, Graff C G, Clarkson E W, Bilgin A, Altbach M I. T2 mapping from highly undersampled data by reconstruction of principal component coefficient maps using compressed sensing. Magn Reson Med. 2012; 67(5): 1355-66.
9. Lam F, Liang Z P. A subspace approach to high-resolution spectroscopic imaging. Magn Reson Med. 2014; 71(4): 1349-57.
10. Fu M, Zhao B, Carignan C, Shosted R K, Perry J L, Kuehn D P, Liang Z P, Sutton B P. High-resolution dynamic speech imaging with joint low-rank and sparsity constraints. Magn Reson Med. 2015; 73(5):1820-32.
11. Tamir J I, Uecker M, Chen W, Lai P, Alley M T, Vasanawala S S, Lustig M. T2 shuffling: Sharp, multicontrast, volumetric fast spin-echo imaging. Magn Reson Med. 2016.
12. Trzasko J D, Manduca A, A unified tensor regression framework for calibrationless dynamic, multi-channel MRI reconstruction. Proc Int Soc Magn Reson Med; 2013; Salt Lake City, Utah
13. Yu Y, Jin J, Liu F, Crozier S. Multidimensional compressed sensing MRI using tensor decomposition-based sparsifying transform. PloS one. 2014; 9(6):e98441.
14. Christodoulou A G, Liang Z-P, 3D dynamic T1 mapping of the myocardium using a time-varying subspace. Proc Int Soc Magn Reson Med; 2015; Toronto.
15. Christodoulou A G, Redler G, Clifford B, Liang Z-P, Halpern H J, Epel B. Fast dynamic electron paramagnetic resonance (EPR) oxygen imaging using low-rank tensors. Journal of Magnetic Resonance. 2016; 270:176-82.
16. He J, Liu Q, Christodoulou A G, Ma C, Lam F, Liang Z-P. Accelerated high-dimensional MR imaging with sparse sampling using low-rank tensors. IEEE Trans Med Imaging. in press.
17. Ma C, Lam F, Ning Q, Clifford B A, Liu Q, Johnson C L, Liang Z-P, High-resolution dynamic 31P-MRSI using high-order partially separable functions. Proc Int Soc Magn Reson Med; 2016; Singapore.
18. Tucker L R. Some mathematical notes on three-mode factor analysis. Psychometrika. 1966; 31(3):279-311.
19. Liu J, Musialski P, Wonka P, Ye J. Tensor completion for estimating missing values in visual data. IEEE Trans Pattern Anal Mach Intell. 2013; 35(1):208-20.
20. De Lathauwer L, De Moor B, Vandewalle J. A multilinear singular value decomposition. SIAM J Matrix Anal Appl. 2000; 21(4):1253-78.
21. Christodoulou A G, Zhang H, Zhao B, Hitchens T K, Ho C, Liang Z-P. High-resolution cardiovascular MRI by integrating parallel imaging with low-rank and sparse modeling. IEEE Trans Biomed Eng. 2013; 60(11):3083-92.
22. Xue H, Greiser A, Zuehlsdorff S, Jolly M-P, Guehring J, Arai A E, Kellman P. Phase-sensitive inversion recovery for myocardial T1 mapping with motion correction and parametric fitting. Magn Reson Med. 2013; 69(5):1408-20.
23. Feng L, Axel L, Chandarana H, Block K T, Sodickson D K, Otazo R. XD-GRASP: Golden-angle radial MRI with reconstruction of extra motion-state dimensions using compressed sensing. Magn Reson Med. 2016; 75(2):775-88.
24. von Knobelsdorff-Brenkenhoff F, Prothmann M, Dieringer M A, Wassmuth R, Greiser A, Schwenke C, Niendorf T, Schulz-Menger J. Myocardial T 1 and T 2 mapping at 3 T: reference values, influencing factors and implications. J Cardiovasc Magn Reson. 2013; 15(1):53.
25. Giri S, Chung Y-C, Merchant A, Mihai G, Rajagopalan S, Raman S V, Simonetti O P. T2 quantification for improved detection of myocardial edema. J Cardiovasc Magn Reson. 2009; 11(1):56.
26. Kellman P, Chung Y-C, Simonetti O P, McVeigh E R, Arai A E. Multicontrast delayed enhancement provides improved contrast between myocardial infarction and blood pool. J Magn Reson Imaging. 2005; 22(5):605-13.
27. Blume U, Lockie T, Stehning C, Sinclair S, Uribe S, Razavi R, Schaeffter T. Interleaved T1 and T2 relaxation time mapping for cardiac applications. J Magn Reson Imaging. 2009; 29(2):480-7.
28. Kvernby S, Warntjes M J B, Haraldsson H, Carlhäll C-J, Engvall J, Ebbers T. Simultaneous three-dimensional myocardial T1 and T2 mapping in one breath hold with 3D-QALAS. J Cardiovasc Magn Reson. 2014; 16(1):102.
29. Akçakaya M, Weingartner S, Basha T A, Roujol S, Bellm S, Nezafat R. Joint myocardial T1 and T2 mapping using a combination of saturation recovery and T2-preparation. Magn Reson Med. 2016; 76(3):888-96.
30. Hamilton J I, Jiang Y, Chen Y, Ma D, Lo W-C, Griswold M, Seiberlich N. MR fingerprinting for rapid quantification of myocardial T1, T2, and proton spin density. Magn Reson Med. 2016.
31. Coolen B F, Poot D H, Liem M I, Smits L P, Gao S, Kotek G, Klein S, Nederveen A J. Three-dimensional quantitative T1 and T2 mapping of the carotid artery: Sequence design and in vivo feasibility. Magn Reson Med. 2016; 75(3):1008-17.
32. DiBella E V, Chen L, Schabel M C, Adluru G, McGann C J. Myocardial perfusion acquisition without magnetization preparation or gating. Magn Reson Med. 2012; 67(3):609-13.
33. Sharif B, Dharmakumar R, Arsanjani R, Thomson L, Merz B, Noel C, Berman D S, Li D. Non-ECG-gated myocardial perfusion MRI using continuous magnetization-driven radial sampling. Magn Reson Med. 2014; 72(6):1620-8.
34. Chen D, Sharif B, Dharmakumar R, Thomson L E, Merz B, Noel C, Berman D S, Li D. Quantification of myocardial blood flow using non-ECG-triggered MR imaging. Magn Reson Med. 2015; 74(3):765-71.
35. Muehling O M, Jerosch-Herold M, Panse P, Zenovich A, Wilson B V, Wilson R F, Wilke N. Regional heterogeneity of myocardial perfusion in healthy human myocardium: assessment with magnetic resonance perfusion imaging. J Cardiovasc Magn Reson. 2004; 6(2):499-507.

What is claimed is:

1. A method for performing magnetic resonance imaging (MRI) on a subject, comprising:
acquiring sparsely-sampled and spatially-encoded MRI imaging data for a region of interest in the subject;

obtaining a temporal factor tensor for the region of interest in the subject, the temporal factor tensor including at least one temporal basis function for each of one or more time-varying dimensions of the subject;

estimating a spatial factor matrix for the region of interest based on the sparsely sampled and spatially-encoded MRI imaging data and the temporal factor tensor, the spatial factor matrix including at least one spatial basis function for a spatially-varying dimension of the subject;

reconstructing a complete image for the region of interest by combining the spatial factor matrix and the temporal factor tensor.

2. The method of claim 1, wherein the obtaining comprises:

acquiring training data at a subset of the spatial encodings for the region of interest;

calculating a training tensor representing the training data for the subset of spatial encodings; and extracting the temporal factor tensor from the training tensor.

3. The method of claim 2, wherein the extracting comprises decomposing the training tensor into a partially-encoded spatial factor matrix, a full core tensor, and temporal basis matrices, followed by calculation of the temporal factor tensor as a product of the core tensor and the temporal basis matrices.

4. The method of claim 2, wherein the training data is acquired with only partial spatial encoding.

5. The method of claim 1, wherein the temporal factor tensor comprises a product of a core tensor and one or more temporal basis matrices, each of the temporal basis matrices corresponding to a different time dimension.

6. The method of claim 5, wherein the time dimension comprises one of cardiac phase, respiratory phase, elapsed time, imaging sequence parameters, or timing parameters.

7. The method of claim 1, wherein the k-space locations for the training data correspond to k-space locations for identifying at least one of cardiac phases or respiratory phases for the subject.

8. The method of claim 1, wherein the subject is a mammal.

9. The method of claim 1, wherein the subject is a human.

10. A non-transitory machine-readable medium having machine executable instructions for causing one or more processors of a magnetic resonance imaging (MRI) machine to execute the imaging method of claim 1.

11. The method of claim 1, wherein the estimating comprises fitting the temporal factor tensor to the sparsely-sampled imaging data to obtain the spatial factor matrix.

12. The method of claim 1, wherein the temporal factor tensor includes basis functions for only the one or more time-varying dimensions of the subject.

13. The method of claim 1, wherein the temporal factor tensor and the spatial factor matrix are derived from separate data sets.

14. A magnetic resonance imaging (MRI) system, comprising:

a magnet operable to provide a magnetic field;

a transmitter operable to transmit to a region within the magnetic field;

a receiver operable to receive a magnetic resonance signal from the region; and a processor operable to control the transmitter and the receiver; wherein the processor is configured to direct the transmitter and receiver to execute a sequence, comprising:

acquiring sparsely-sampled and spatially-encoded MRI imaging data for a region of interest in a subject;

obtaining a temporal factor tensor for the region of interest in the subject, the temporal factor tensor including at least one temporal basis function for each of one or more time-varying dimensions of the subject;

estimating a spatial factor matrix for the region of interest based on the sparsely sampled and spatially-encoded MRI imaging data and the temporal factor tensor, the spatial factor matrix including at least one spatial basis function for a spatially-varying dimension of the subject; and reconstructing a complete image for the region of interest by combining the spatial factor matrix and the temporal factor tensor.

15. The MRI system of claim 14, wherein the obtaining comprises:

acquiring training data at a subset of the spatial encodings for the region of interest;

calculating a training tensor representing the training data for the subset of spatial encodings; and extracting the temporal factor tensor from the full training tensor.

16. The MRI system of claim 15, wherein the extracting comprises decomposing the training tensor into a partially-encoded spatial factor matrix, a full core tensor, and full temporal basis matrices, followed by calculation of the temporal factor tensor as a product of the core tensor and temporal basis matrices.

17. The MRI system of claim 15, wherein the training data is acquired with only partial spatial encoding.

18. The MRI system of claim 14, wherein the estimating comprises fitting the temporal factor tensor to the sparsely sampled imaging data to obtain the spatial factor matrix.

19. The MRI system of claim 14, wherein the temporal factor tensor comprises a product of a core tensor and one or more temporal basis matrices, each of the temporal basis matrices corresponding to a different time dimension.

20. The MRI system of claim 19, wherein the time dimension comprises one of cardiac phase, respiratory phase, elapsed time, imaging sequence parameters, or timing parameters.

21. The MRI system of claim 14, wherein the k-space locations for the training data correspond to k-space locations for identifying at least one of cardiac phases or respiratory phases for the subject.

22. The MRI system of claim 14, wherein the subject is a mammal.

23. The MRI system of claim 14, wherein the subject is a human.

24. The MRI system of claim 14, wherein the temporal factor tensor includes basis functions for only the one or more time-varying dimensions of the subject.

25. The MRI system of claim 14, wherein the temporal factor tensor and the spatial factor matrix are derived from separate data sets.

* * * * *